United States Patent
Hirotsune

(10) Patent No.: US 11,844,776 B2
(45) Date of Patent: Dec. 19, 2023

(54) COMPOSITION FOR TREATMENT AND/OR PREVENTION OF PERIPHERAL NERVE DISORDER

(71) Applicants: OSAKA CITY UNIVERSITY, Osaka (JP); SENJU PHARMACEUTICAL CO., LTD., Osaka (JP)

(72) Inventor: Shinji Hirotsune, Osaka (JP)

(73) Assignees: OSAKA CITY UNIVERSITY, Osaka (JP); SENJU PHARMACEUTICAL CO., LTD., Osaka (JP)

( * ) Notice: Subject to any disclaimer, the term of this patent is extended or adjusted under 35 U.S.C. 154(b) by 0 days.

(21) Appl. No.: 16/303,629

(22) PCT Filed: May 22, 2017

(86) PCT No.: PCT/JP2017/019067
§ 371 (c)(1),
(2) Date: Nov. 20, 2018

(87) PCT Pub. No.: WO2017/204166
PCT Pub. Date: Nov. 30, 2017

(65) Prior Publication Data
US 2019/0314320 A1 Oct. 17, 2019

(30) Foreign Application Priority Data
May 23, 2016 (JP) .................. 2016-102878

(51) Int. Cl.
| A61K 31/27 | (2006.01) |
|---|---|
| A61P 25/02 | (2006.01) |
| A61K 9/00 | (2006.01) |
| A61K 31/341 | (2006.01) |
| A61K 31/351 | (2006.01) |
| A61K 31/4402 | (2006.01) |

(52) U.S. Cl.
CPC ............ *A61K 31/27* (2013.01); *A61K 9/0019* (2013.01); *A61K 31/341* (2013.01); *A61K 31/351* (2013.01); *A61K 31/4402* (2013.01); *A61P 25/02* (2018.01)

(58) Field of Classification Search
CPC .... A61K 31/27; A61K 31/341; A61K 31/351; A61K 31/44; A61K 31/4402; A61K 31/77; A61K 9/0019; A61P 25/02
See application file for complete search history.

(56) References Cited

U.S. PATENT DOCUMENTS

| 9,371,359 B2 | 6/2016 | Hirotsune |
| 2007/0004643 A1 | 1/2007 | Shirasaki et al. |
| 2013/0244945 A1 | 9/2013 | Hirotsune |
| 2016/0250276 A1 | 9/2016 | Hirotsune |

FOREIGN PATENT DOCUMENTS

| CN | 103705979 A | * | 4/2014 |
| JP | 2006-76989 A | | 3/2006 |
| WO | WO-2006/122237 | | 11/2006 |
| WO | WO-2012/074120 A1 | | 6/2012 |

OTHER PUBLICATIONS

Trager et al., J Neurochem. Jul. 2014; 130(2): 268-279 (Year: 2014).*
Caetano, Arq Neuropsiquiatr 2003;61(1):48-50. (Year: 2003).*
Oh, Letters to the Editor, Muscle and Nerve Feb. 2002. (Year: 2002).*
Das et al., J Neurochem. Jan. 2013; 124(1): 133-14 (Year: 2013).*
South Carolina Sports Medicine & Orthopedic Center, copyrighted 2013. (Year: 2013).*
Antoniadis, Dtsch Arztebl Int. Nov. 2008; 105(45): 776-781 (Year: 2008).*

(Continued)

*Primary Examiner* — Jean P Cornet
(74) *Attorney, Agent, or Firm* — Foley & Lardner LLP

(57) ABSTRACT

The present invention provides a means for treating and/or preventing peripheral nerve disorder by facilitating regeneration of peripheral nerves. Specifically, the present invention provides a composition for treating and/or preventing peripheral nerve disorder comprising a compound represented by the general formula (I):

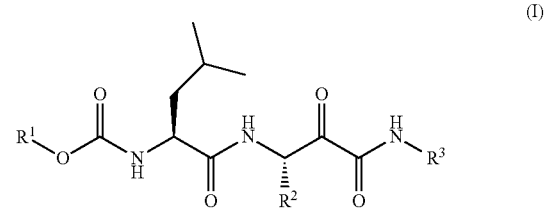

(I)

wherein $R^1$ is lower alkyl substituted with lower alkoxy, lower alkyl substituted with a heterocyclic group, a heterocyclic group, or a group represented by the formula (IIa):

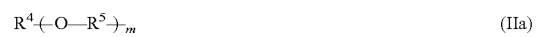

(IIa)

wherein $R^4$ is lower alkyl, $R^5$ is lower alkylene, and m is an integer of 1 to 6;

$R^2$ is lower alkyl optionally substituted with phenyl; and $R^3$ is lower alkyl optionally substituted with halogen, lower alkoxy, or phenyl; condensed polycyclic hydrocarbon; or hydrogen.

8 Claims, 14 Drawing Sheets

Specification includes a Sequence Listing.

(56) References Cited

OTHER PUBLICATIONS

Taba, J Neurochem. Jan. 2013; 124(1): 133-14. (Year: 2013).*
Hirata et al., "Hypoxia Activates Calpains in the Nerve Fiber Layer of Monkey Retinal Explants," Investigative Opthalmology & Visual Science, vol. 56, No. 10, pp. 6049-6057 (Sep. 2015).
Ryu et al., "Critical Role of Calpain in Axonal Damage-Induced Retinal Ganglion Cell Death," Journal of Neuroscience Research, vol. 90, No. 4, pp. 802-815 (Apr. 2012).
Extended European Search Report dated Dec. 4, 2019 in European Application No. 17802758.7.
Shimazawa et al., "A novel calpain inhibitor, SNJ-1945, reduces retinal cell death in vitro and in vivo," Journal of Pharmacological Sciences, (2009), vol. 109, Supplement 1, p. 89.
Badalamente et al., "Neuromuscular recovery using calcium protease inhibition after median nerve repair in primates," Proc. Natl. Acad. Sci. USA, (1989), vol. 86, pp. 5983-5987.
Badalamente et al., "Neuromuscular Recovery After Peripheral Nerve Repair: Effects of an Orally-Administered Peptide in a Primate Model," Journal of Reconstructive Microsurgery, (1995), vol. 11, No. 6, pp. 429-437.
Wu et al., "Calpain 3 Expression Pattern During Gastrocnemius Muscle Atrophy and Regeneration Following Sciatic Nerve Injury in Rats," International Journal of Molecular Science, (2015), vol. 16, pp. 26927-26935.
Xie et al., "Calpain-meditated down-regulation of myelin-associated glycoprotein in lysophosphatidic acid-induced neuropathic pain," Journal of Neurochemistry, (2010), vol. 113, No. 4, pp. 1002-1011.
Volser et al., "Calpain-Mediated Signaling Mechanisms in Neuronal Injury and Neurodegeneration," Molecular Neurobiology, (2008), vol. 38, No. 1, pp. 78-100.
Yano et al., "Calpain inhibitor suppresses paclitaxel-induced neuropathic pain and underlying demyelination," Journal of Pharmacologcal Sciences, (2013), vol. 121, Supplement 1, p. 83.
Shea et al, "Enhancement of Neurite Outgrowth Following Calpain Inhibition is Mediated by Protein Kinase C," Journal of Neurochemistry, (1995), vol. 65, pp. 517-527.
Migorance-Le Meur et al., "Neurite consolidation is an active process requiring constant repression of protrusive activity," The EMBO Journal, (2009), vol. 28, No. 3, pp. 248-260.
Bains et al., "Pharmacological analysis of the cortical neuronal cytoskeletal protective efficacy of the calpain inhibitor SNJ-1945 in a mouse traumatic brain injury model," Journal of Neurochemistry, (2013), vol. 125, pp. 125-132.
Smith et al., "Calpain inhibition reduces structural and functional impairment of retinal ganglion cells in experimental optic neuritis," Journal of Neurochemistry, (2016), vol. 139, pp. 270-284.
Bain et al., "Functional Evaluation of Complete Sciatic, Peroneal, and Posterior Tibial Nerve Lesions in the Rat," Plastic and Reconstructive Surgery, (1989), vol. 83, No. 1, pp. 129-138.
Bennett et al., "A peripheral mononeuropathy in rat that produces disorders of pain sensation like those seen in man," Pain, 1988, vol. 33, pp. 87-107.
Stanfield et al., "A transient Postmamillary Component of the Rat Fornix During Development: Implications for Interspecific Differences in Mature Axonal Projections," The Journal of Neuroscience, (1987), vol. 7, No. 10, pp. 3350-3361.
Yamada et al., "Inhibition of calpain increases LIS1 expression and partially rescues in vivo phenotypes in a mouse model of lissencephaly," Nature Medicine, vol. 15, No. 10, pp. 1202-1207, Oct. 2009.
Wynshaw-Boris et al., "Lissencephaly: Mechanistic insights from animal models and potential therapeutic strategies," Seminars in Cell & Developmental Biology, vol. 21, pp. 823-830, available online Aug. 3, 2010.
Takitoh et al., "Inhibiton of calpain increases LIS1 and partially rescues in vivo phenotypes in LIS1 mutant mice: a potential therapy for lissencephaly," Journal of Japanese Biochemical Society, Abstract, p. 3P-0426, 2008.
Hirotsune, "Inhibition of calpain increases LIS1 and partially rescues in vivo phenotypes in LIS1 mutant mice: a potential therapy for lissencephaly," Journal of Japanese Biochemical Society, Abstract, p. 2S2a-3, 2009.
Yamada et al., "Inhibition of calpain increases LIS1 (PAFAH1B1) and partially rescues in vivo phenotypes in a mouse model of lissencephaly," Annual Meeting of the Molecular Biology Society of Japan Koen Yoshishu, vol. $32^{nd}$, No. vol. 2, p. 141, 2P-0404, Oct. 2009.
Shinji, "Development of novel treatment for lissencephaly through elucidation of molecular mechanism," Boshi Kenko Kyokai Shoni Igaku Josei Kenkyu Hokokusho, vol. $21^{st}$, pp. 19-22, Jun. 2010.
Sorimachi, "Diseases caused by calpain deficiency," Medical Science Digest, vol. 36, No. 3, pp. 706-710, vol. 36, No. 3, Mar. 2010.
Shumueli et al., "Platelet-Activating Factor (PAF) Acetylhydrolase Activity, LIS1 Expression, and Seizures," Journal of Neuroscience Research, vol. 57, pp. 176-184, 1999.
Morris et al., "The lissencephaly gene product Lis1, a protein involved in neuronal migration, interacts with a nuclear movement protein, NudC," Current Biology, vol. 8, pp. 603-606, 1998.
Reiner et al., "Lissencephaly Gene (LIS1) Expression in the CNS Suggests a Role in Neuronal Migration," The Journal of Neuroscience, vol. 15, No. 5, pp. 3730-3738, May 1995.
International Search Report issued in application No. PCT/JP2011/078000 dated Dec. 27, 2011.
Takahashi et al., "Retinal distribution of SNJ-1945 by microautoradiography," The $18^{th}$ International Congress for Eye Research, P432, Sep. 24-29, 2008, Bejing, C.
Toba et al., "Post-natal Treatment by a blood-brain-barrier permeable calpain inhibitor, SNJ1945 rescued defective function in lissencephaly", Scientific Reports, vol. 3, Article No. 1224, Feb. 6, 2013, 10 pages.
Yamada et al., "Therapeutic Intervention for Genetic Disease by the Augmented Recycling of Target Proteins"; Editorial, Future Neurology, vol. 5, Issue 1, Jan. 2010, pp. 5-8.
Komura et al., "A Novel Calpain Inhibitor, ((1S)-1((((1S)-1-Benzyl-3-Cyclopropylamino-2,3-DI-Oxopropyl)Amino) Carbonyl)-3-Methylbutyl) Carbamic Acid 5-Methoxy-3-Oxapentyl Ester, Protects Neuronal Cells From Cerebral Ischemia-Induced Damage in Mice," Neuroscience, vol. 157, pp. 309-318, 2008.
Annals New York Academy of Sciences, 1998, vol. 844, No. 1, pp. 131-137.
Office Action dated Nov. 8, 2022 for JP patent application No. 2021-184736.
Guyton et al.,"Calpeptin Attenuated Inflammation, Cell Death, and Axonal Damage in Animal Model of Multiple Sclerosis" Neurosci Res. 88(11): 2398-2408 (Aug. 2010).

* cited by examiner

1. Control treatment
2. SNJ treatment
Red circles: Complete sciatic nerve injury
Blue circles: control

SEQUENCE LISTING

<160> NUMBER OF SEQ ID NOS: 1

<210> SEQ ID NO 1
<211> LENGTH: 25
<212> TYPE: RNA
<213> ORGANISM: Mus musculus

<400> SEQUENCE: 1
uuaaggugau uccucaggag gguga                                              25

COMPOSITION FOR TREATMENT AND/OR PREVENTION OF PERIPHERAL NERVE DISORDER

CROSS-REFERENCE TO RELATED APPLICATIONS

This application is the U.S. National Stage of International Application PCT/JP2017/019067, filed May 22, 2017, which claims priority from Japanese Patent Application No. 2016-102878, filed May 23, 2016.

TECHNICAL FIELD

The present invention relates to a composition for treating and/or preventing peripheral nerve disorder.

BACKGROUND ART

Peripheral nerve disorder (neuropathy) refers to dysfunction of spinal nerves in a distal portion relative to a nerve plexus or nerve root. For example, various levels of sensory dysfunction, pain, muscle weakness and atrophy, decreased deep tendon reflex, vasomotor nerve symptoms, and like symptoms appear alone or in a combination of two or more.

A peripheral nerve disorder may damage a single nerve (mononeuropathy), or simultaneously damage many nerves (polyneuropathy). The treatment of peripheral nerve disorder basically focuses on alleviation or removal of the cause of the neural disorder. However, it is often difficult to specify or remove the cause, and, even if the cause can be removed, it is difficult in many cases to recover the damaged neuron. If regeneration of the peripheral nerve can be facilitated, it is possible to increase the likelihood of starting treatment before specifying the cause of the nerve disorder; further, recovery in function of the damaged neurons increases the possibility of further alleviation of the symptoms. The facilitation of regeneration is also expected to have an effect on the prevention of peripheral nerve disorder. Under such circumstances, a method for facilitating regeneration of peripheral nerves has been demanded.

CITATION LIST

Patent Literature

PTL 1: JP2006-76989A
PTL 2: WO2012/074120

Non-Patent Literature

NPL 1: Bain, J. R., Mackinnon, S. E., and Hunter, D. A. (1989). Functional evaluation of complete sciatic, peroneal, and posterior tibial nerve lesions in the rat. Plastic and reconstructive surgery 83, 129-138.
NPL 2: Bennett, G. J., and Xie, Y. K. (1988). A peripheral mononeuropathy in rat that produces disorders of pain sensation like those seen in man. Pain 33, 87-107.
NPL 3: Stanfield, B. B., Nahin, B. R., and O'Leary, D. D. (1987). A transient postmamillary component of the rat fornix during development: implications for interspecific differences in mature axonal projections. The Journal of Neuroscience: The Official Journal of the Society for Neuroscience 7, 3350-3361.

SUMMARY OF INVENTION

Technical Problem

An object of the present invention is to treat and/or prevent peripheral nerve disorder. In particular, an object of the present invention is to treat and/or prevent peripheral nerve disorder by facilitating regeneration of peripheral nerves.

Solution to Problem

The present inventors found that use of a specific compound makes it possible to facilitate axon outgrowth in peripheral nerves and further enable regeneration of damaged peripheral nerves. The inventors made further improvement based on this finding and completed the present invention. Specifically, the present invention encompasses, for example, the inventions of the following items.

Item 1. A composition for treating and/or preventing peripheral nerve disorder comprising a compound represented by the general formula (I):

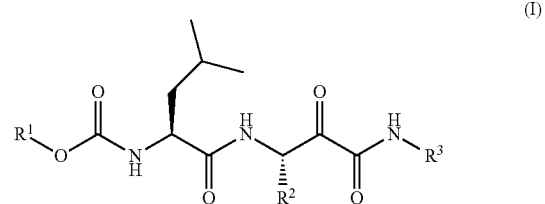

wherein $R^1$ is lower alkyl substituted with lower alkoxy, lower alkyl substituted with a heterocyclic group, a heterocyclic group, or a group represented by the formula (IIa):

$$R^4\text{-}(\text{O-}R^5\text{-})_m \quad (IIa)$$

wherein $R^4$ is lower alkyl, $R^5$ is lower alkylene, and m is an integer of 1 to 6;

$R^2$ is lower alkyl optionally substituted with phenyl; and
$R^3$ is lower alkyl optionally substituted with halogen, lower alkoxy, or phenyl; condensed polycyclic hydrocarbon; or hydrogen.

Item 2. The composition according to item 1, wherein $R^1$ is a group represented by the formula (IIa):

$$R^4\text{-}(\text{O-}R^5\text{-})_m \quad (IIa)$$

wherein $R^4$ is lower alkyl, $R^5$ is lower alkylene, and m is an integer of 1 to 6.

Item 3. The composition according to item 1, wherein $R^1$ is a group represented by the formula (IIb):

$$H_3C\text{-}(\text{O-}CH_2CH_2\text{-})_n \quad (IIb)$$

wherein n is an integer of 1 to 6.

Item 4. The composition according to item 1, wherein the heterocyclic group that is a substituent for the lower alkyl represented by $R^1$ is pyridyl optionally having lower alkyl.

Item 5. The composition according to item 1, wherein the heteroatom of the heterocyclic group represented by R is oxygen.

Item 6. The composition according to any one of items 1 to 5, wherein the lower alkyl represented by $R^3$ is cyclopropyl.

Item 7. The composition according to item 1, wherein the compound represented by the general formula (I) is ((1S)-1-((((1S)-1-benzyl-2,3-dioxo-3-(cyclopropylamino)propyl)amino)carbonyl)-3-methylbutyl)carbamic acid 2-methoxyethyl ester, ((1S)-1-((((1S)-1-benzyl-2,3-dioxo-3-(cyclopropylamino)propyl)amino) carbonyl)-3-methylbutyl) carbamic acid 5-methoxy-3-oxapentyl ester, ((1S)-1-((((1S)-1-benzyl-2,3-dioxo-3-(cyclopropylamino)propyl)amino)carbonyl)-3-methylbutyl)carbamic acid 8-methoxy-3,6-dioxaoctyl ester, ((1S)-1-((((1S)-1-benzyl-2,3-dioxo-3-(cyclopropylamino)propyl)amino)carbonyl)-3-methylbutyl)carbamic acid 11-methoxy-3,6,9-trioxaundecanyl ester, or ((1S)-1-((((1S)-1-benzyl-3-(cyclopropylamino)-2,3-dioxopropyl)amino)carbonyl)-3-methylbutyl)carbamic acid 2-(pyridin-2-yl)ethyl ester.

Item 8. The composition according to any one of items 1 to 7, which is an oral preparation, injection, or intravenous drip.

Item 9. The composition according to any one of items 1 to 8, wherein the compound represented by the general formula (I) is used such that 0.1 to 2,000 mg of the compound is administered to a peripheral nerve disorder patient per day.

Item 10. The composition according to any one of items 1 to 9, wherein the peripheral nerve disorder is at least one member selected from the group consisting of mechanical or entrapment neuropathy, metabolic neuropathy, infectious neuropathy, and drug-induced peripheral nerve disorders.

Item 11. A method for treating peripheral nerve disorder comprising administering a compound represented by the general formula (I):

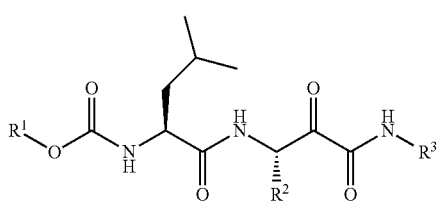
(I)

wherein R is lower alkyl substituted with lower alkoxy, lower alkyl substituted with a heterocyclic group, a heterocyclic group, or a group represented by the formula (IIa):

(IIa)

wherein $R^4$ is lower alkyl, $R^5$ is lower alkylene, and m is an integer of 1 to 6;

$R^2$ is lower alkyl optionally substituted with phenyl; and $R^3$ is lower alkyl optionally substituted with halogen, lower alkoxy, or phenyl; condensed polycyclic hydrocarbon; or hydrogen;

to a peripheral nerve disorder patient.

Item 12. The method according to item 11, wherein $R^1$ is a group represented by the formula (IIb):

(IIb)

wherein n is an integer of 1 to 6.

Item 13. A compound represented by the general formula (I):

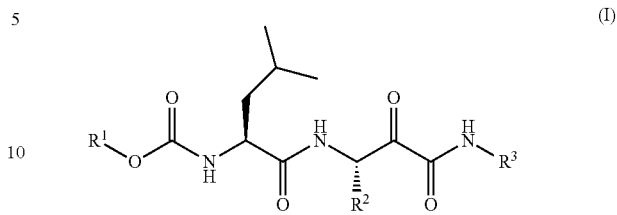
(I)

wherein $R^1$ is lower alkyl substituted with lower alkoxy, lower alkyl substituted with a heterocyclic group, a heterocyclic group, or a group represented by the formula (IIa):

(IIa)

wherein $R^4$ is lower alkyl, $R^5$ is lower alkylene, and m is an integer of 1 to 6;

$R^2$ is lower alkyl optionally substituted with phenyl; and $R^3$ is lower alkyl optionally substituted with halogen, lower alkoxy, or phenyl; condensed polycyclic hydrocarbon; or hydrogen, or a composition comprising the compound, for use in the treatment or prevention of peripheral nerve disorder.

Item 14. The compound or pharmaceutical composition according to item 13, wherein $R^1$ is a group represented by the formula (IIb):

(IIb)

wherein n is an integer of 1 to 6.

Item 15. Use of a compound in the production of a medicament for treating or preventing peripheral nerve disorder, the compound being represented by the general formula (I):

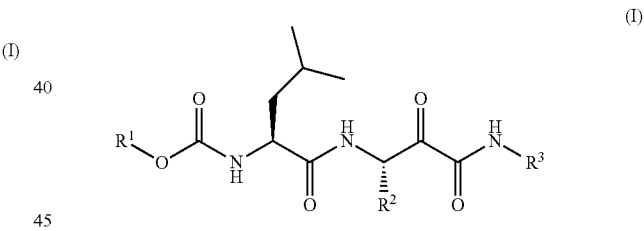
(I)

wherein R is lower alkyl substituted with lower alkoxy, lower alkyl substituted with a heterocyclic group, a heterocyclic group, or a group represented by the formula (IIa):

(IIa)

wherein $R^4$ is lower alkyl, $R^5$ is lower alkylene, and m is an integer of 1 to 6;

$R^2$ is lower alkyl optionally substituted with phenyl; and $R^3$ is lower alkyl optionally substituted with halogen, lower alkoxy, or phenyl; condensed polycyclic hydrocarbon; or hydrogen.

Item 16. The use according to item 15, wherein $R^1$ is a group represented by the formula (IIb):

(IIb)

wherein n is an integer of 1 to 6.

Advantageous Effects of Invention

The composition for treating and/or preventing peripheral nerve disorder of the present invention enables treatment and/or prevention of peripheral nerve disorder. In this specification, the term "treatment" means alleviation or removal of disorders or developed diseases and/or their symptoms. Further, in this specification, the term "prevention" means prevention of occurrence of disorders or onset of diseases. Further, the present composition (and the compound as an active ingredient of the composition) is capable of facilitating peripheral nerve elongation or regeneration. Therefore, the present composition may also be referred to as a "composition for peripheral nerve elongation" or a "composition for peripheral nerve regeneration." The term "peripheral nerve regeneration" used herein means elongation of a peripheral nerve damaged by an external or internal factor toward the target cell, and preferably means a capability to reconstruct the neural circuit.

Further, generally, according to the classification based on histopathological disorders, the pathogenesis of peripheral nerve disorder is divided into axonopathy, neuronopathy, and myelinopathy. Since the compound represented by formula (I) above has, in particular, excellent axon outgrowth and myelin recovery promotion effects, the composition for treating and/or preventing peripheral nerve disorder of the present invention is particularly preferable for the treatment and/or prevention of peripheral nerve disorders mainly caused by axonopathy and myelinopathy.

Further, the compound represented by formula (I) above is capable of significantly facilitating the regenerative capacity even in peripheral nerves with significantly decreased regenerative capacity. Further, the compound represented by formula (I) above is also capable of regeneration of completely damaged (severed) peripheral nerves, or peripheral nerves degenerated after a certain time has passed after the damage. Therefore, in addition to pediatric patients, the compound is also expected to exert effects in adult, middle-aged, presenile, and elderly patients.

BRIEF DESCRIPTION OF DRAWINGS

The right-side figure in FIG. 1 shows a graph showing analysis results regarding axon regeneration. In the graph, the vertical axis denotes axon length ($\mu$m) and the horizontal axis denotes incubation time (hours). Further, the right-side figure in FIG. 1 shows results of observation of dorsal root ganglion neurons obtained from 3-day-old (P3), 10-day-old (P10), or 15-day-old (P15) mice, or from 3-day-old LIS1 heterozygous mice (P3 Lis1(+/−)) using a confocal laser microscope. Each white bar indicates 20 $\mu$m. * denotes $p<0.05$,  denotes $p<0.01$, and * denotes $p<0.001$. The same applies to all figures below.

The left-side figure in FIG. 2 shows analysis results of the expression amount of LIS1 protein in dorsal root ganglion neurons of 3-day-old or 15-day-old mice by western blotting. GAPDH (glyceraldehyde-3-phosphate dehydrogenase) was detected as a positive control. Further, the right-side figure shows the analysis results regarding the expression ratio of LIS1 protein based on the intensity of the band detected by western blotting.

Figure 3:
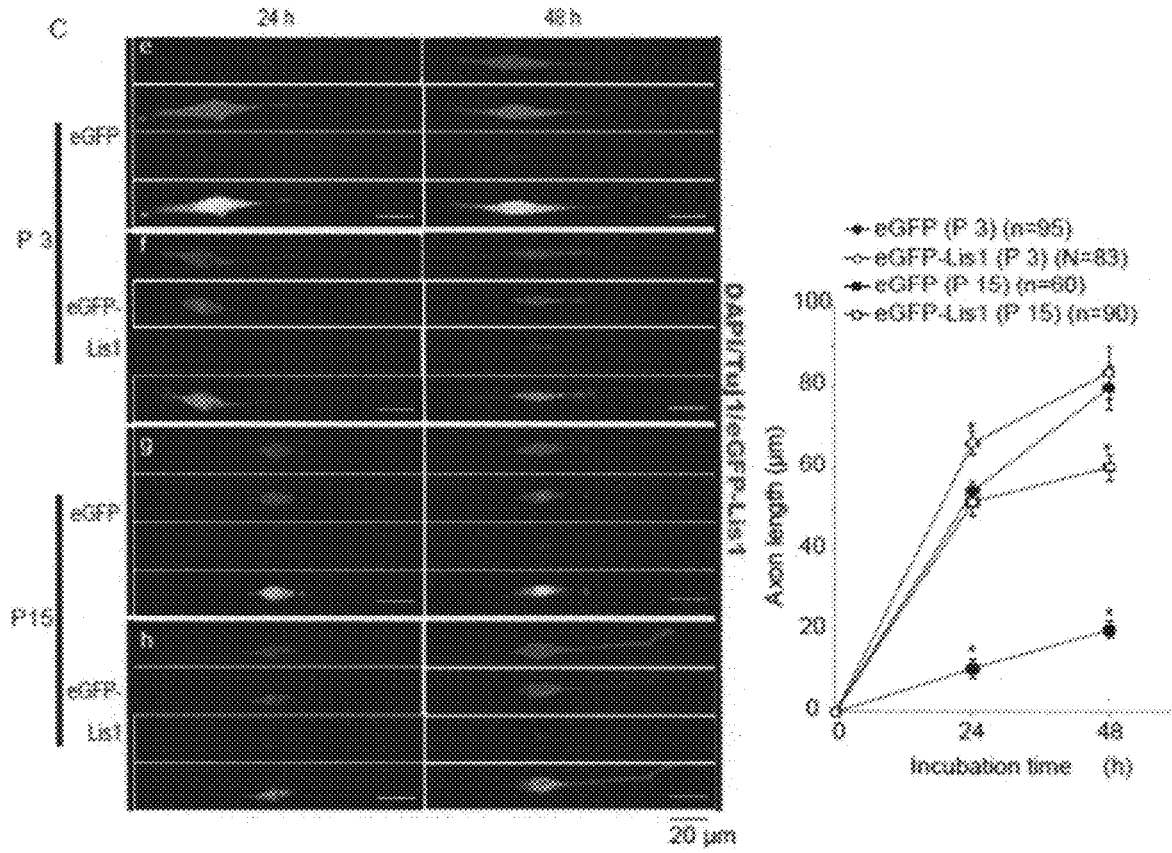

The right-side figure in FIG. 3 shows the analysis results regarding the correlation between acceleration of Lis1 gene expression and axon length; the analysis was performed by using dorsal root ganglion neurons isolated from 3-day-old or 15-day-old mice. Further, the right-side figure shows results of observation of each dorsal root ganglion neuron using a confocal laser microscope. Detection of DAPI is shown in blue, detection of Tuj1 is shown in red, and detection of eGFP is shown in green. In each analysis result, Tuj1, eGFP, DAPI, and Merge thereof are shown in this order from top to bottom. Each white bar indicates 20 $\mu$m.

Figure 4:
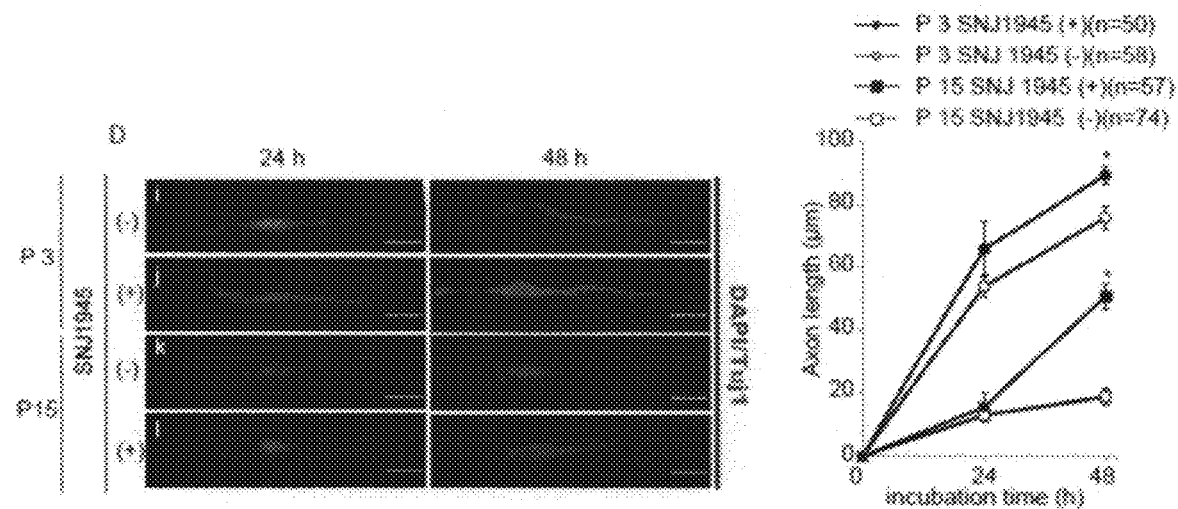

The right-side figure of FIG. 4 shows the analysis results regarding the correlation between presence/absence of SNJ1945 addition and an axon length; the analysis was performed by using dorsal root ganglion neurons isolated from 3-day-old mice. Further, the left-side figure shows results of observation of each dorsal root ganglion neuron using a confocal laser microscope. Each white bar indicates 20 $\mu$m.

Figure 5:
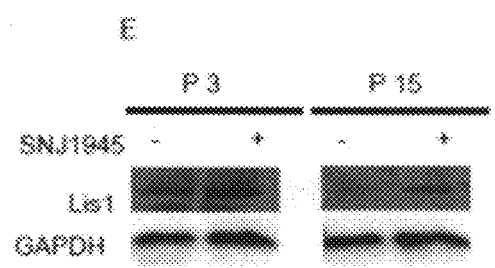
Figure 5:
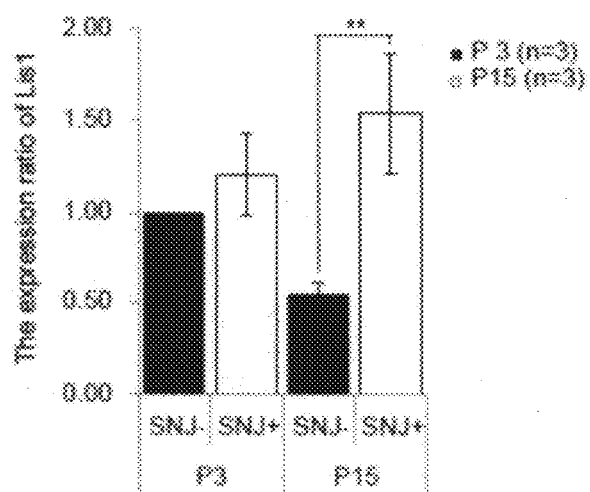

FIG. 5 shows the analysis results as to whether the expression amount of LIS1 protein expressed in dorsal root ganglion neurons isolated from 3-day-old or 15-day-old mice changes depending on the presence or absence of SNJ1945 addition.

Figure 6:
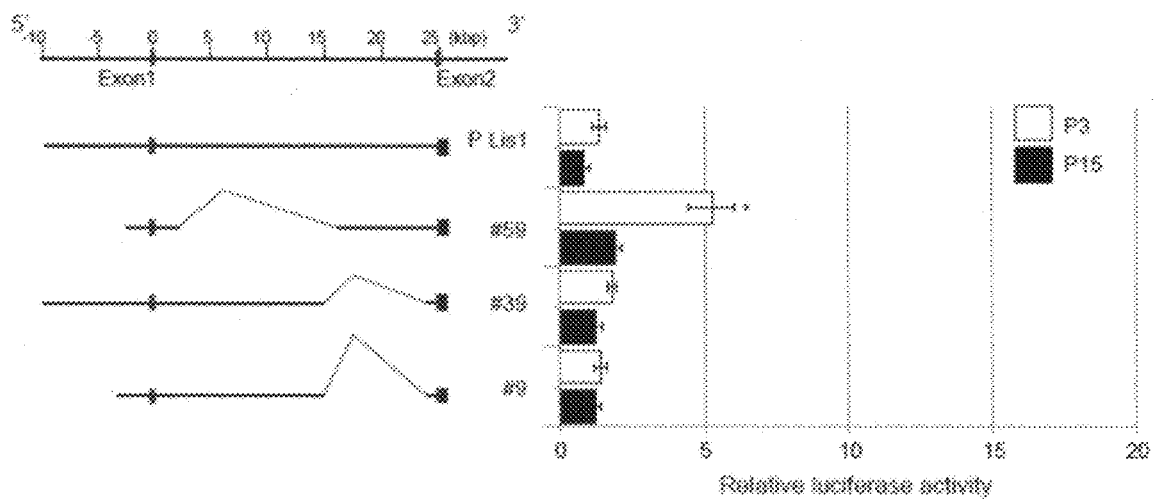
Figure 6:
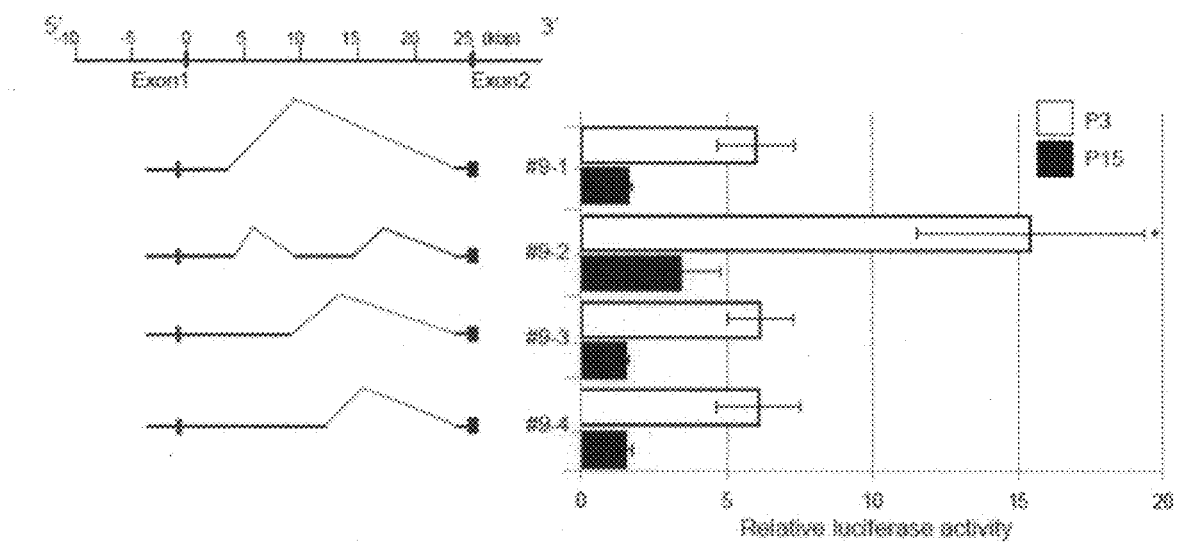

The left-side figure in FIG. 6 shows the structure of a reporter gene introduced into each plasmid to be used for luciferase reporter assay for specifying a transcriptional regulatory region of LIS1 gene. The reporter gene more specifically has a structure in which a luciferase gene is bonded to the 3' end of LIS1 gene in which a part of intron1 and upstream are deleted. The red square denotes the exon of LIS1 gene, and the blue square denotes luciferase gene. Further, the right-side figure shows the results of luciferase assay (relative value of luciferase activity) using each reporter gene.

Figure 7:
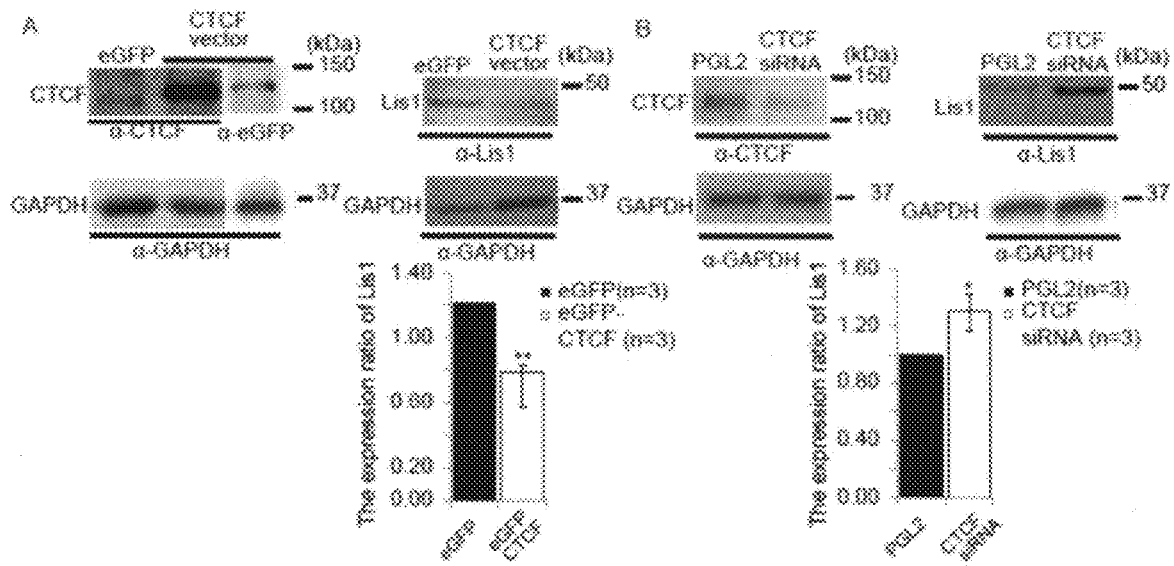

FIG. 7A shows analysis results of the expression amount of LIS1 by western blotting after CTCF was expressed in a dorsal root ganglion neuron by using an expression vector. Further, FIG. 7B shows analysis results of the expression amount of LIS1 by western blotting after knockdown of CTCF in a dorsal root ganglion neuron using siRNA.

Figure 8:
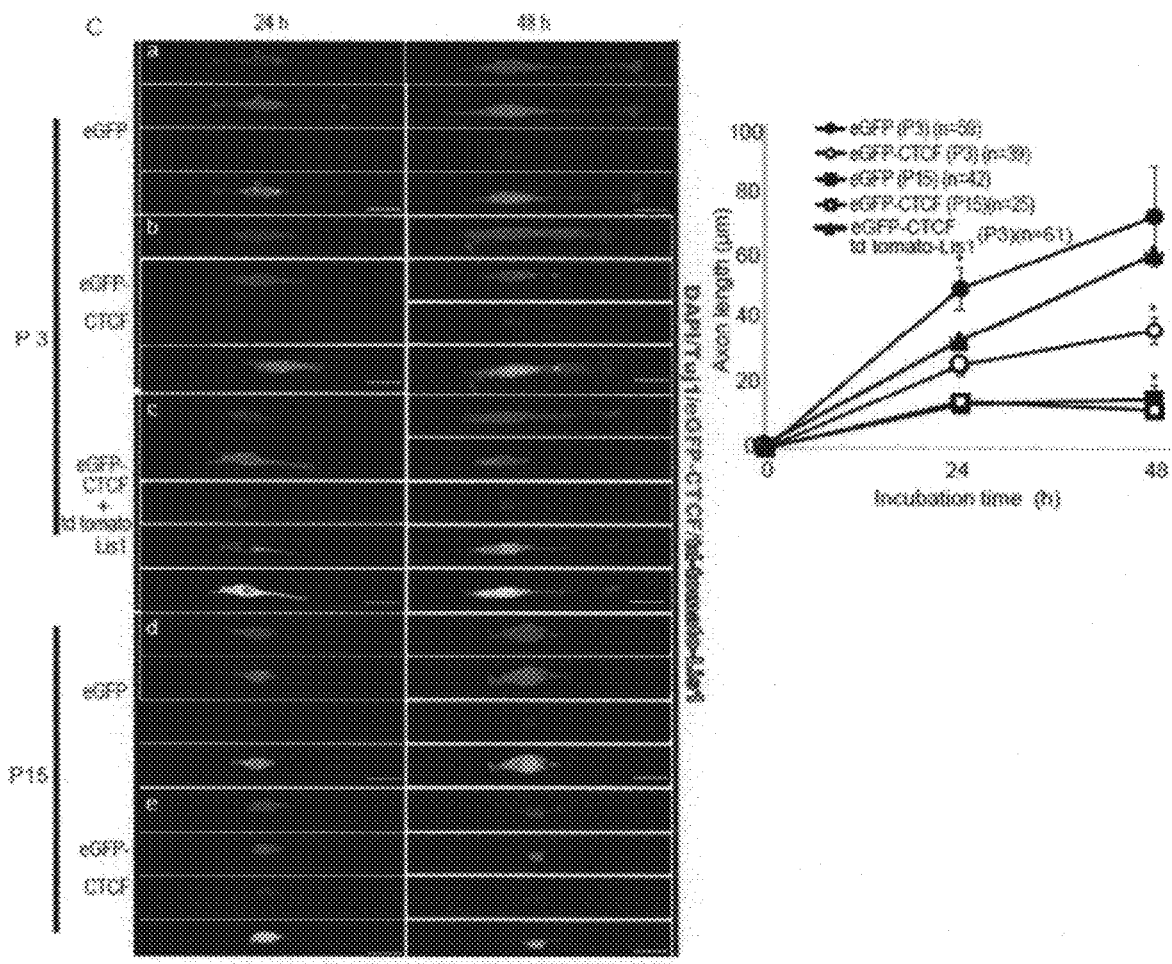

FIG. 8 shows the results of observation using a confocal laser microscope after forced expression of CTCF in a dorsal root ganglion neuron of 3-day-old (P3) and 15-day-old (P15) using an expression vector.

Figure 9:
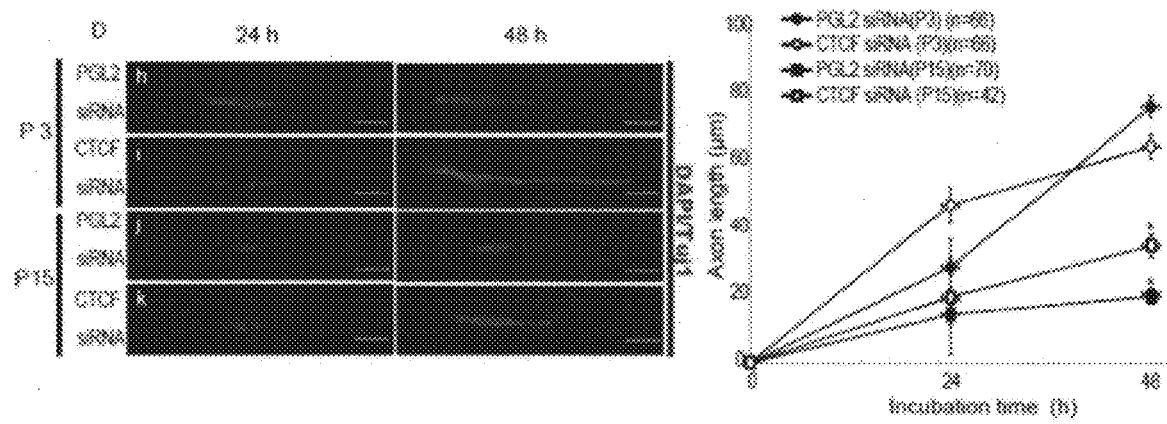

FIG. 9 shows the results of observation using a confocal laser microscope after knockdown of CTCF in a dorsal root ganglion neuron of 3-day-old (P3) and 15-day-old (P15) using siRNA.

Figure 10:
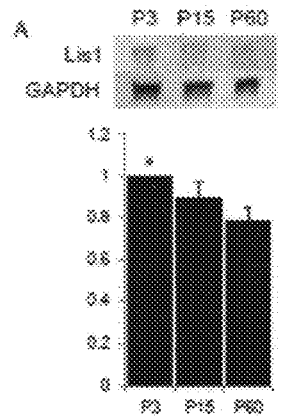

FIG. 10 shows results of analysis regarding the expression amount of LIS1 in a mouse central nervous system by western blotting.

Figure 11:
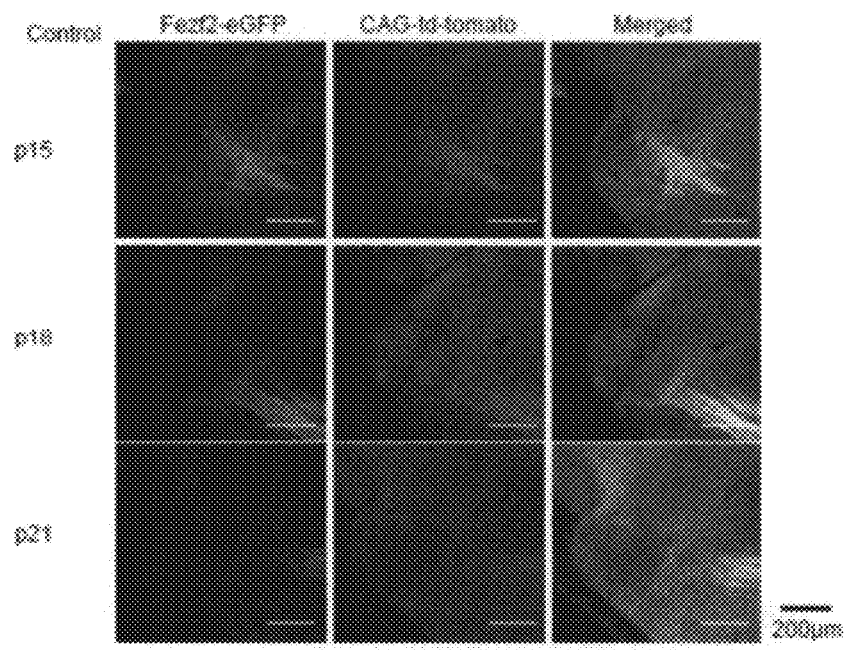

FIG. 11 shows results of visualization of the neural circuit of a mouse fetus (12.5 days) after expression of fluorescent protein td-tomato using a CAG promoter.

Figure 12:
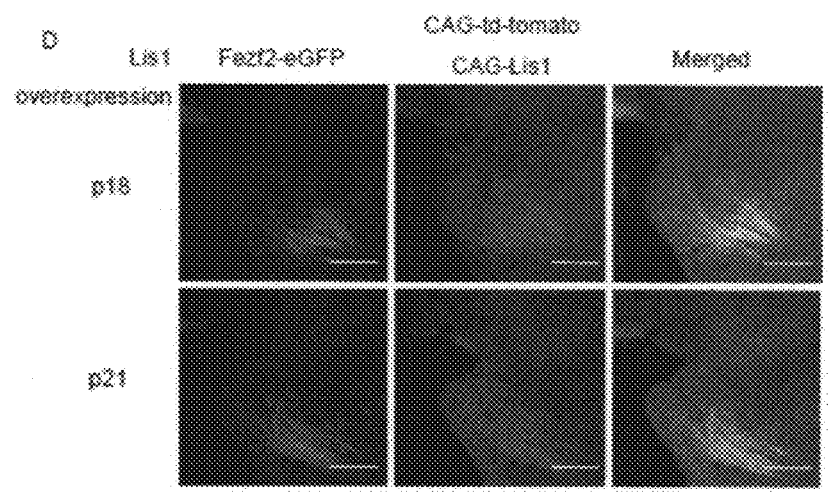

FIG. 12 shows results of visualization of the neural circuit of a mouse fetus (12.5 days) after expression of LIS1 and fluorescent protein td-tomato using a CAG promoter.

Figure 13:
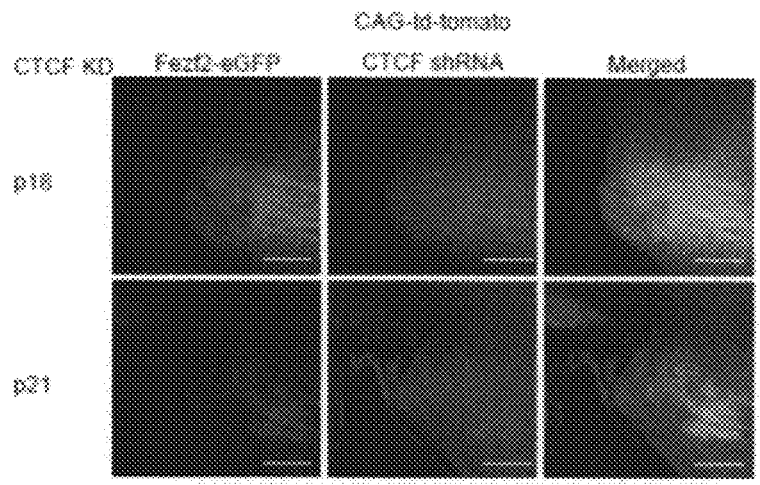

FIG. 13 shows results of visualization of the neural circuit of a mouse fetus (12.5 days) after expression of shRNA of CTCF and fluorescent protein td-tomato using a CAG promoter.

Figure 14:
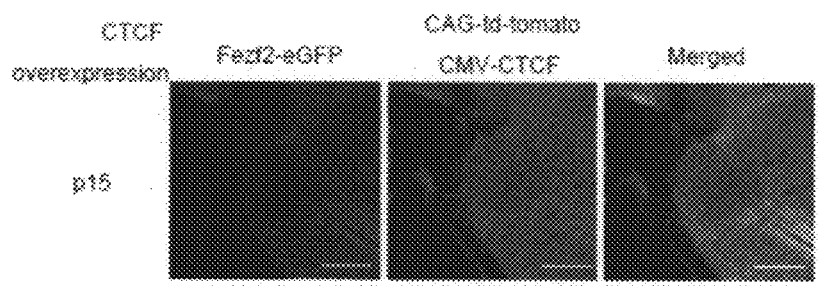

FIG. 14 shows results of visualization of the neural circuit of a mouse fetus (12.5 days) after expression of CTCF and fluorescent protein td-tomato using a CAG promoter and a CMV promoter.

Figure 15:
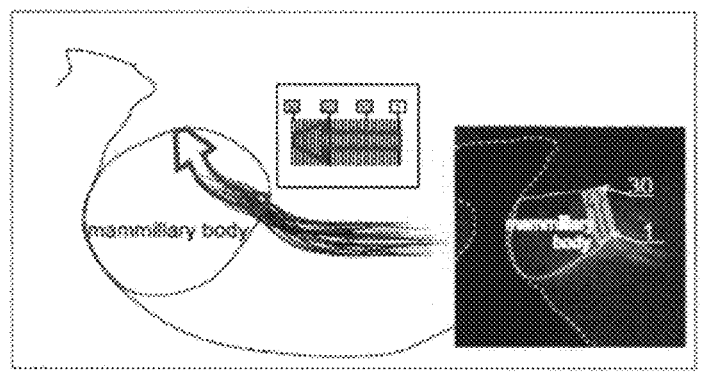

FIG. 15 shows the mammillary body and orientation of nerve fiber in a mouse brain.

Figure 16:
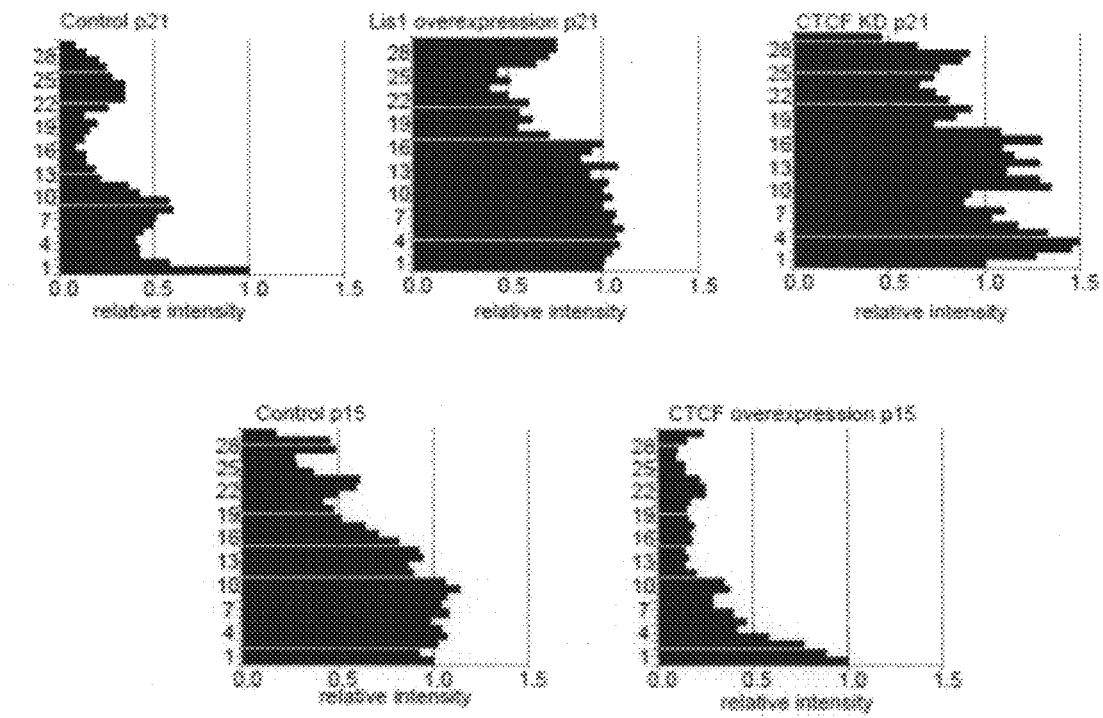

FIG. 16 shows results of quantitative determination of the elimination degree in each analysis result, obtained by using the scale of FIG. 15.

Figure 17:
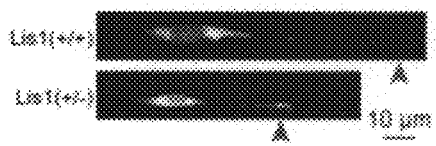

FIG. 17 shows results of staining of dorsal root ganglion neurons of normal type (LIS1 homozygous) and LIS1 heterozygous mutant using anti-GSK$\beta$ antibody.

Figure 18:
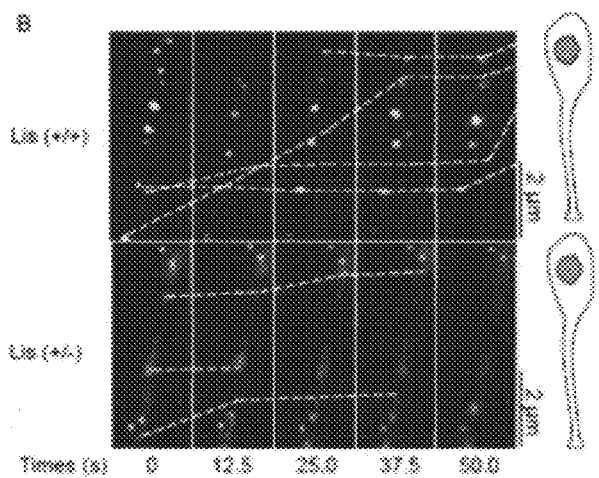

FIG. 18 shows results of analysis of displacement of GSK$\beta$ in dorsal root ganglion neurons using live cell imaging.

Figure 19:
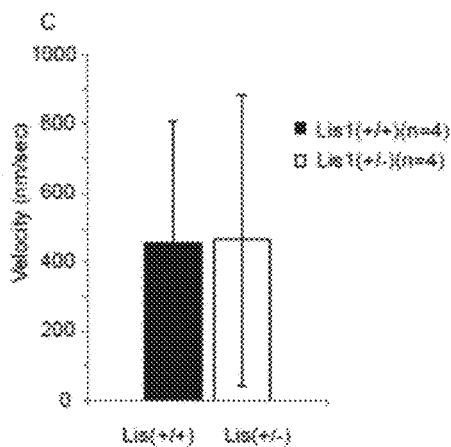

FIG. 19 shows results of analysis of GSK3β displacement velocity by observation of displacement of GSK3β in dorsal root ganglion neurons using live cell imaging.

Figure 20:
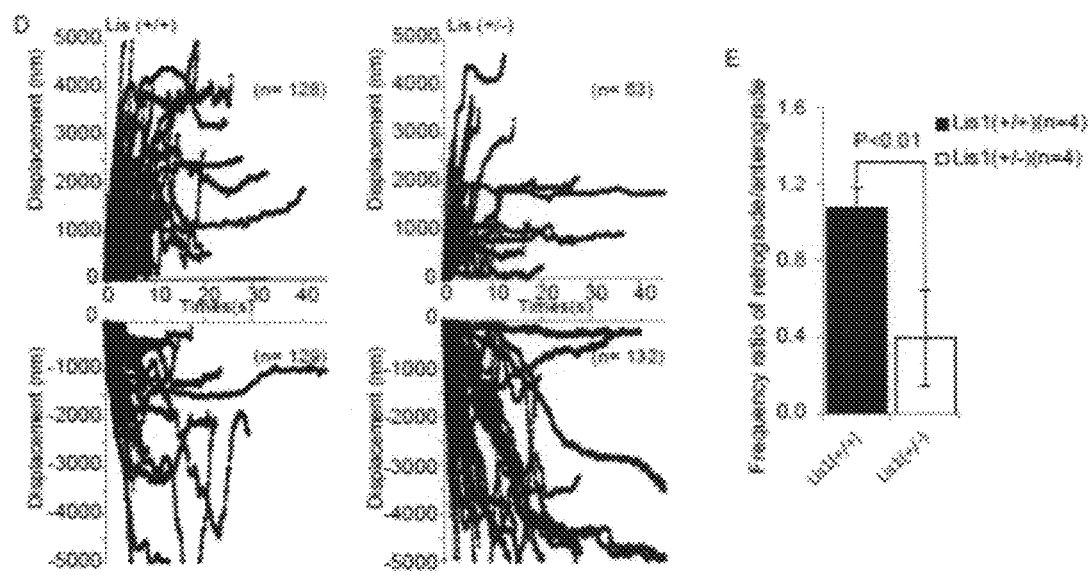

FIG. 20 shows results of analysis of GSK3β displacement frequency by observation of displacement of GSK3β in dorsal root ganglion neurons of normal type and LIS1 heterozygous mutant using live cell imaging.

Figure 21:
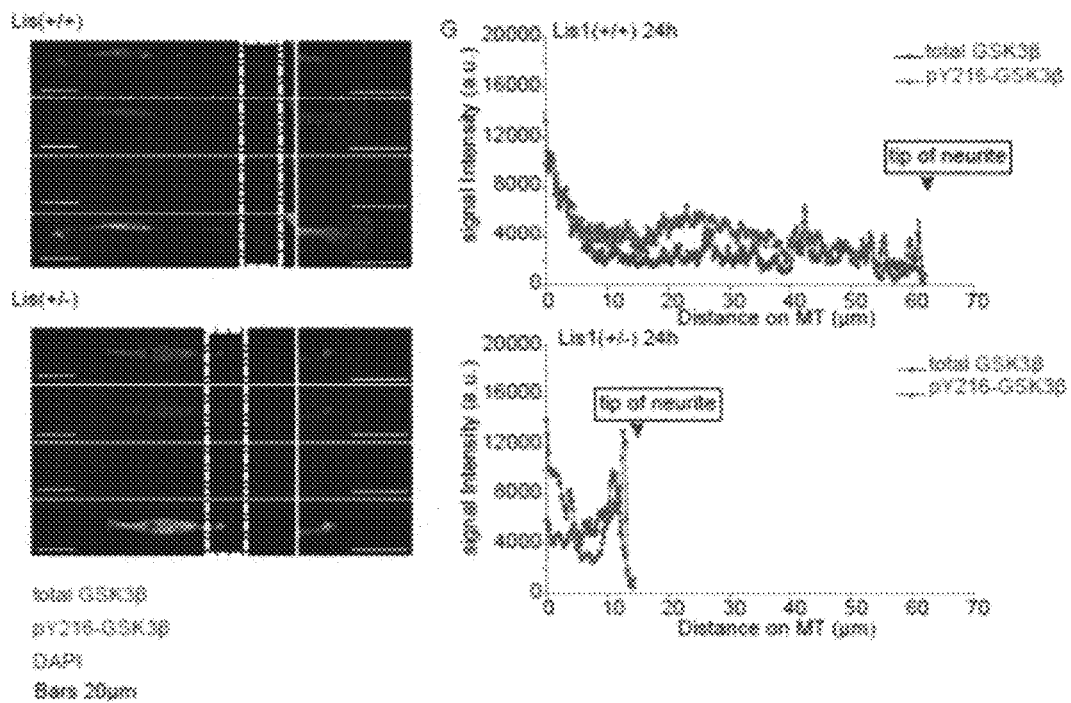

FIG. 21 shows results of analysis of activation of GSKβ in dorsal root ganglion neurons of normal type and LIS1 heterozygous mutant using a phosphorylation-specific antibody of 216 thyrosine.

Figure 22:
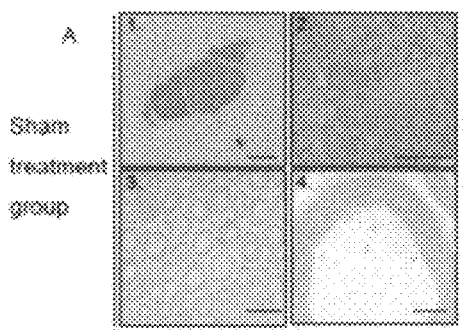

FIG. 22 shows results of microscope analysis of a sciatic nerve portion of a sham group, which was not subjected to sciatic nerve injury upon the production of a mouse sciatic nerve injury model. The details of the four images are as follows. Upper left [1]: small enlargement; upper right [2]: large enlargement, electron microscope image; lower left [3]: small enlargement; lower right [4]: large enlargement. The positions of these photos are the same in all figures showing results of microscope observation of sciatic nerves.

Figure 23:
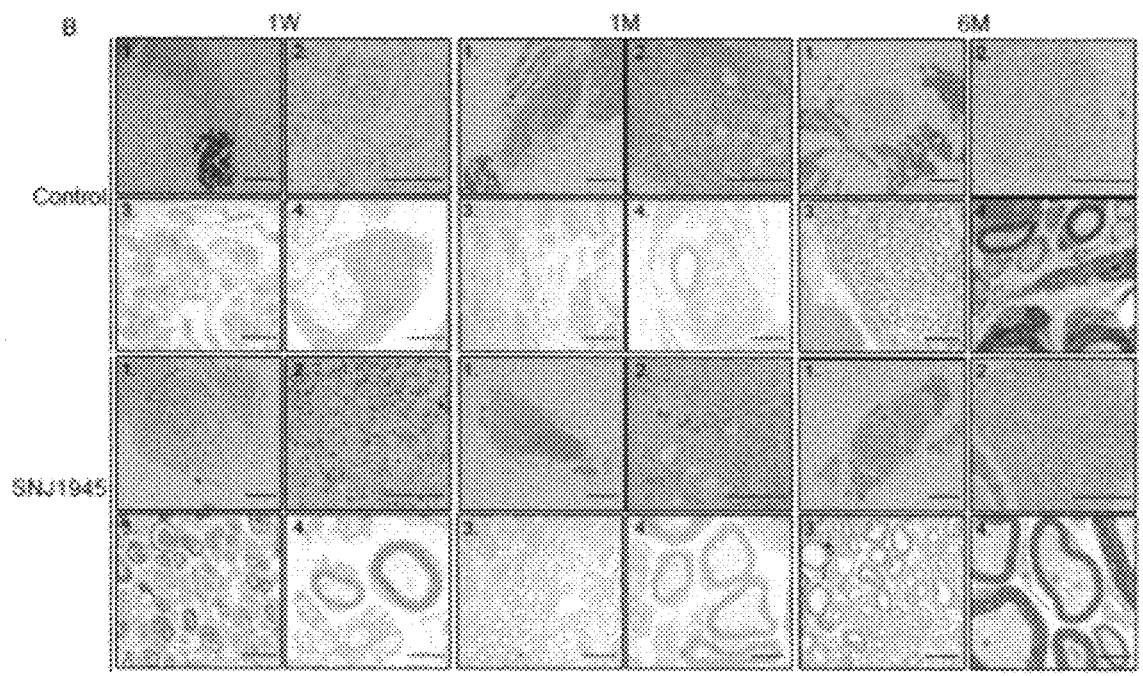

FIG. 23 shows results of microscope analysis of a sciatic nerve portion in a complete nerve injury model and a control group. "1W" indicates 1 week after the treatment, "1M" indicates 1 month after the treatment, and "6M" indicates 6 months after the treatment.

Figure 24:
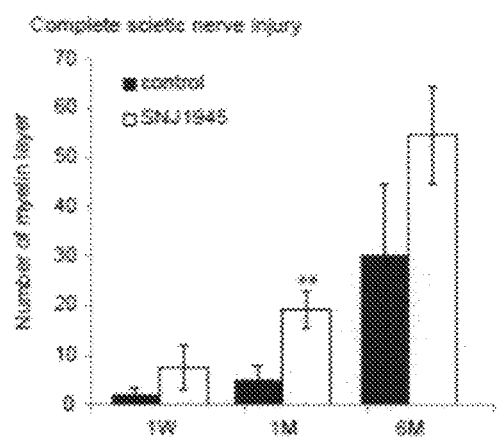

FIG. 24 shows a graph showing the number of myelins that were confirmed to be recovered by referring to the image of FIG. 23.

Figure 25:
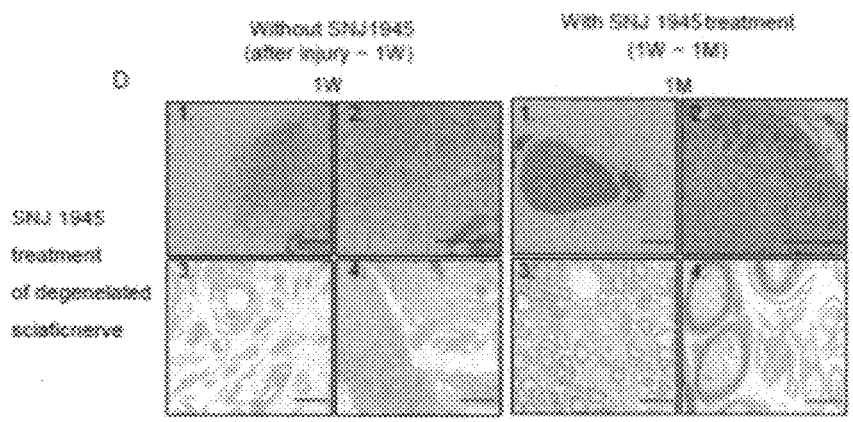

FIG. 25 shows results of analysis in a sciatic nerve portion regarding activation of nerve regeneration; the results were obtained by administering SNJ1945 on a complete nerve injury model 1 week after severance of a sciatic nerve, and analyzing with a microscope 1 month after the severance.

Figure 26:
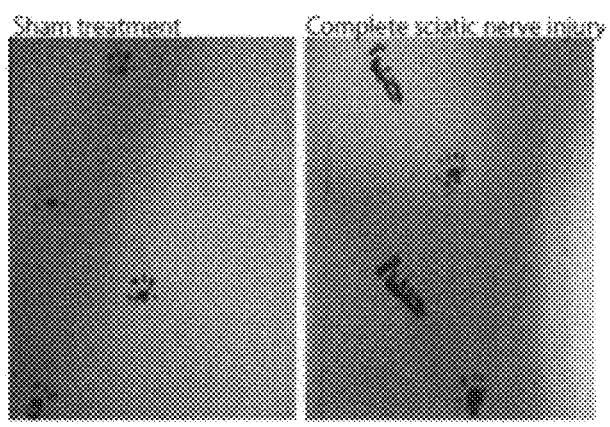

FIG. 26 shows walking footprints of a sham-treated mouse (left) and a complete injury mouse model (right).

Figure 27:
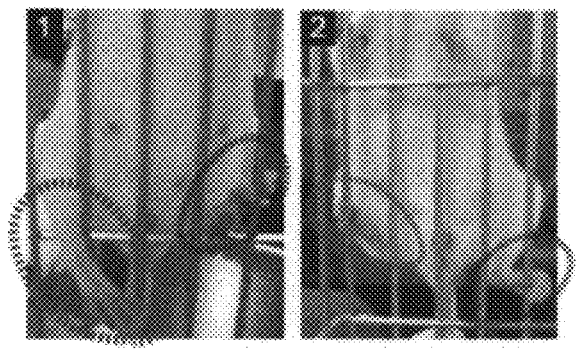

FIG. 27 shows the condition of the feet of a complete injury mouse model that had its right sciatic nerve severed, 1 month after the SNJ1945 administration performed as described above.

Figure 28:
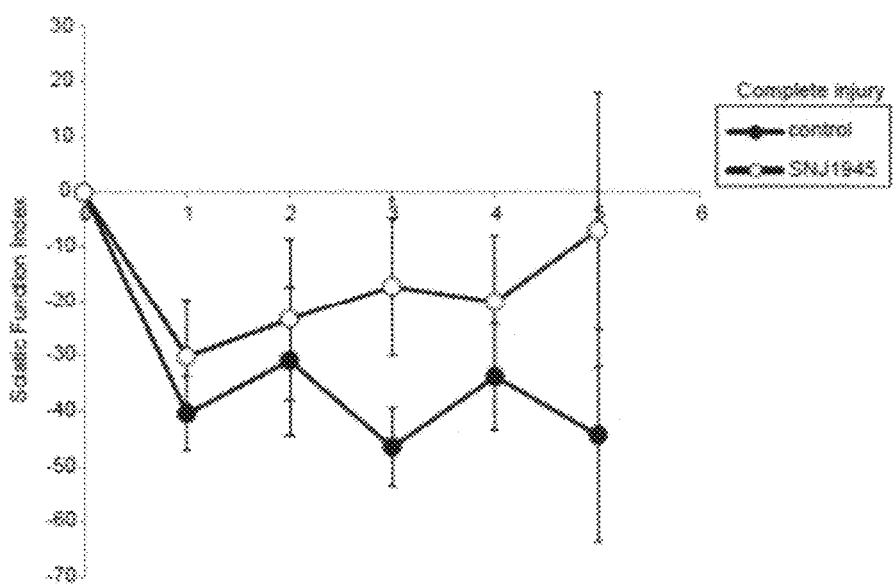

FIG. 28 shows the results of evaluation of motor function of a sciatic nerve injury model mouse based on the sciatic function index (SFI) and print length factor (PLI) using Footprint.

DESCRIPTION OF EMBODIMENTS

In the general formula (I) described above, $R^1$ may be lower alkyl substituted with lower alkoxy, or lower alkyl substituted with a heterocyclic group. That is, $R^1$ may be lower alkyl, which is substituted with lower alkoxy or a heterocyclic group. The lower alkyl is preferably $C_{1-6}$ (1, 2, 3, 4, 5, or 6) linear or branched alkyl, such as methyl, ethyl, propyl, isopropyl, butyl, isobutyl, sec-butyl, tert-butyl, pentyl, isopentyl, neopentyl, tert-pentyl, 1-methylbutyl, 2-methylbutyl, 1,2-dimethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1-ethyl-2-methylpropyl, or 1,1,2-trimethyl propyl. More preferred among these is linear or branched alkyl having 2 or 3 carbon atoms, and particularly preferred is ethyl.

The lower alkoxy that is a substituent for the lower alkyl represented by $R^1$ is preferably $C_{1-6}$ (1, 2, 3, 4, 5, or 6) lower alkoxy. That is, the lower alkyl substituted with lower alkoxy represented by R is preferably lower alkyl substituted with $C_{1-6}$ lower alkoxy. Examples of the $C_{1-6}$ lower alkoxy include methoxy, ethoxy, propoxy, isopropoxy, butoxy, isobutoxy, sec-butoxy, tert-butoxy, pentyloxy, isopentyloxy, neopentyloxy, tert-pentyloxy, 1-methylbutoxy, 2-methylbutoxy, 1,2-dimethylpropoxy, hexyloxy, 1-methylpentyloxy, 2-methylpentyloxy, 3-methylpentyloxy, 4-methylpentyloxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1-ethyl-2-methylpropoxy, and 1,1,2-trimethylpropoxy. Preferred among these are methoxy and ethoxy.

The alkoxy is optionally substituted with lower alkoxy on the carbon that forms the alkoxy. The lower alkoxy that is a substituent is further optionally substituted with lower alkoxy. Such substitution may be repeated several times. That is, $R^1$ may also be a group represented by the formula (IIa):

$$R^4{+}O{-}R^5{+}_m \quad \text{(IIa)}$$

wherein $R^4$ is lower alkyl, $R^5$ is lower alkylene, and m is an integer of 1 to 6.

A more preferable group is represented by the formula (IIb):

$$H_3C{+}O{-}CH_2CH_2{+}_n \quad \text{(IIb)}$$

wherein n is an integer of 1 to 6.

The lower alkyl represented by $R^4$ in the formula (IIa) is preferably $C_{1-6}$ (1, 2, 3, 4, 5, or 6) linear or branched alkyl, such as methyl, ethyl, propyl, isopropyl, butyl, isobutyl, sec-butyl, or tert-butyl. Preferred among these are methyl, isopropyl, and tert-butyl, and more preferred is methyl.

The lower alkylene represented by $R^5$ in the formula (IIa) is preferably $C_{1-4}$ (1, 2, 3, or 4) alkylene, such as methylene, ethylene, trimethylene, or tetramethylene; among which ethylene is more preferred. The lower alkylene represented by $R^5$ is optionally substituted with, for example, lower alkyl (in particular, $C_{1-6}$ linear or branched alkyl), such as methyl or ethyl.

m in the formula (IIa) is an integer of 1 to 6 (1, 2, 3, 4, 5, or 6), and preferably an integer of 2 to 5. n in the formula (IIb) is an integer of 1 to 6 (1, 2, 3, 4, 5, or 6), preferably an integer of 1 to 5, and more preferably an integer of 2 to 5.

The heterocyclic group that is a substituent for the lower alkyl represented by $R^1$ is preferably pyridyl optionally having lower alkyl (i.e., optionally substituted with lower alkyl). More specifically, the lower alkyl substituted with a heterocyclic group represented by $R^1$ is preferably lower alkyl substituted with pyridyl optionally having lower alkyl. Examples of the pyridyl include 2-pyridyl, 3-pyridyl, and 4-pyridyl. The lower alkyl that the pyridyl optionally has is preferably $C_{1-3}$ lower alkyl, such as methyl, ethyl, propyl, or isopropyl. When the pyridyl has lower alkyl, the lower alkyl is preferably, but not limited to, located at the 5- or 6-position of the pyridyl (i.e., the hydrogen at the 5- or 6-position of the pyridyl is substituted with the lower alkyl).

$R^1$ may also be a heterocyclic group. Examples of the heterocyclic group represented by $R^1$ include 5- to 7-membered aromatic groups containing one to three atoms independently selected from the group consisting of sulfur, oxygen, and nitrogen; and partially or fully reduced, saturated heterocyclic groups. Specific examples thereof include furyl, thienyl, pyrrolyl, azepinyl, pyrazolyl, imidazolyl, oxazolyl, isoxazolyl, thiazolyl, isothiazolyl, 1,2,3-oxadiazolyl, triazolyl, tetrazolyl, thiadiazolyl, pyranyl, pyridyl, pyridazinyl, pyrimidinyl, pyrazinyl, morpholinyl, thiomorpholinyl, pyrrolidinyl, pyrrolinyl, imidazolidinyl, pyrazolidinyl, piperidinyl, piperazinyl, oxazolidinyl, isoxazolidinyl, thiazolidinyl, pyrazolidinyl, tetrahydrofuranyl, tetrahydropyranyl, tetrahydrothiophenyl, and the like. Preferred among these are saturated heterocyclic groups, more preferred are 5- to 6-membered saturated heterocyclic groups containing oxygen atoms, even more preferred are 1-, 2-, or 3-tetrahydrofuranyl and 1-, 2-, 3-, or 4-tetrahydropyranyl, and most preferred are 3-tetrahydrofuranyl and 4-tetrahydropyranyl.

Examples of the lower alkyl represented by $R^2$ include those mentioned as examples of lower alkyl substituted with lower alkoxy, or lower alkyl substituted with a heterocyclic group represented by $R^1$; among which methyl, ethyl, or isobutyl is preferred. The lower alkyl represented by $R^2$ is preferably substituted with phenyl. Preferable examples of the lower alkyl substituted with phenyl represented by $R^2$ are benzyl and phenylethyl.

The lower alkyl represented by $R^3$ is preferably $C_{1-6}$ (1, 2, 3, 4, 5, or 6) linear or branched alkyl, such as methyl, ethyl, propyl, isopropyl, butyl, isobutyl, sec-butyl, tert-butyl, pentyl, isopentyl, neopentyl, tert-pentyl, 1-methylbutyl, 2-methylbutyl, 1,2-dimethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1-ethyl-2-methylpropyl, or 1,1,2-trimethylpropyl. Linear or branched alkyl having 2 or 3 carbon atoms is more preferred. The lower alkyl represented by $R^3$ may also be cycloalkyl. Examples of the cycloalkyl include cyclopropyl, cyclobutyl, cyclopentyl, cyclohexyl, and the like; among which cyclopropyl or cyclobutyl is preferred.

This lower alkyl is optionally substituted with halogen, such as fluorine, chlorine, or bromine; among which fluorine is preferred. When the lower alkyl is substituted with halogen, $R^3$ is preferably trifluoromethyl or 2,2,2-trifluoroethyl.

Examples of the lower alkyl substituted with lower alkoxy represented by $R^3$ include those mentioned as examples of the lower alkyl substituted with lower alkoxy represented by $R^1$. Among these, $C_{1-6}$ (1, 2, 3, 4, 5, or 6) lower alkoxy substituted with methoxy or ethoxy is preferred. Examples of the lower alkyl substituted with phenyl represented by $R^3$ include those mentioned as examples of the lower alkyl substituted with phenyl represented by $R^2$.

The condensed polycyclic hydrocarbon represented by $R^3$ is, for example, indanyl, indenyl, naphthyl, anthranil, pentalenyl, or azulenyl; among which indanyl is preferred.

The compounds to be contained in the composition for treating and/or preventing peripheral nerve disorder of the present invention may be various solvates, crystalline polymorphs, or prodrugs of the compounds.

The above compounds can be synthesized, for example, by the following method. Some of the compounds are known compounds (see PTL 1 mentioned above).

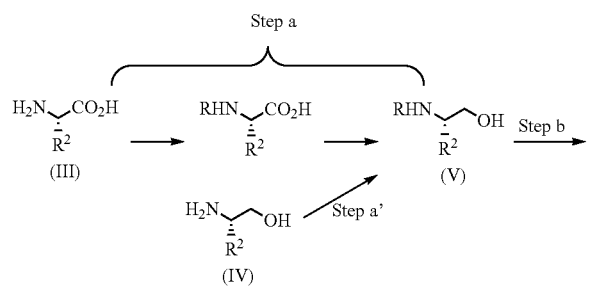

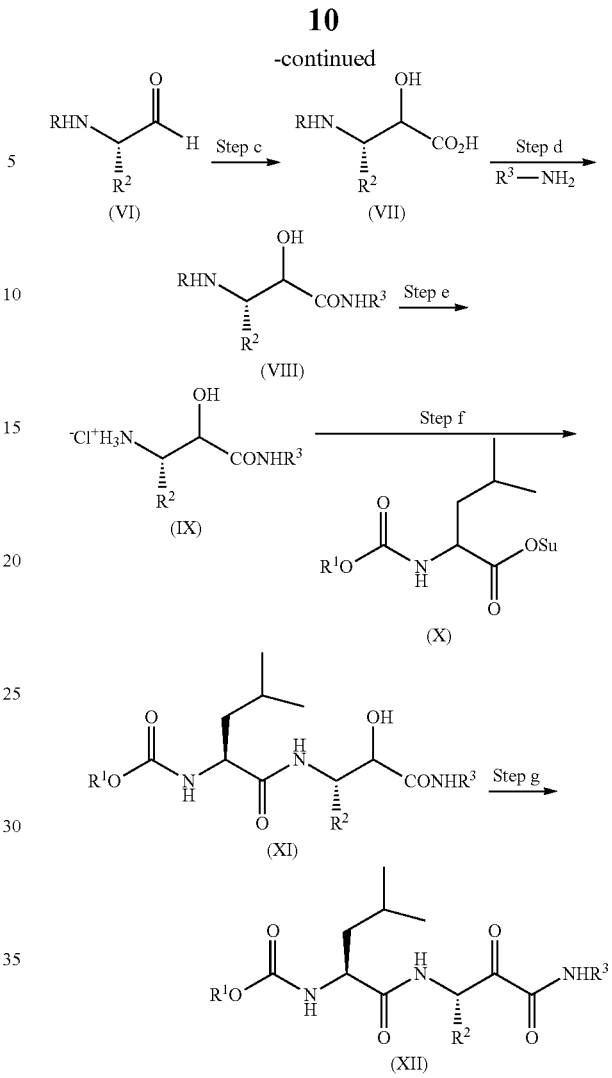

wherein R is a protecting group, and the other groups are as defined above.

Step a comprises adding a protecting group to the amino group of an amino acid represented by the formula (III) to convert it to a mixed acid anhydride, and reducing the mixed acid anhydride with a reducing agent to obtain a compound represented by the formula (V) (hereinafter referred to as compound (V)). The addition and removal of the protecting group can be carried out by a known method. Examples of the protecting group include formyl, optionally substituted $C_{1-6}$ alkylcarbonyl (e.g., acetyl and propionyl), optionally substituted phenylcarbonyl, optionally substituted $C_{1-6}$ alkyl-oxycarbonyl (e.g., methoxycarbonyl, ethoxycarbonyl, and tert-butoxycarbonyl), optionally substituted phenyloxycarbonyl, optionally substituted $C_{7-10}$ aralkyloxycarbonyl (e.g., phenyl-$C_{1-4}$ alkyloxycarbonyl, such as benzyloxycarbonyl), and the like. Usable examples of their substituents include halogen (e.g., fluorine, chlorine, bromine, and iodine), nitro, and the like. The number of substituents is about 1 to 3. The most preferable protecting group is tert-butoxycarbonyl (Boc).

Examples of the reducing agent used in the above reaction include lithium aluminum hydride, sodium borohydride, sodium bis(2-methoxyethoxy)aluminum hydride, and the like; among which sodium borohydride is preferred. The reaction temperature is in the range of −40° C. to 30° C., and preferably −20° C. to 0° C.

The compound (V) can also be obtained by similarly adding an aforementioned amino-protecting group to an amino alcohol represented by the formula (IV) (step a').

Step b comprises oxidizing the compound (V) with dimethyl sulfoxide (DMSO) in the presence of an activating agent for DMSO to obtain a compound represented by the formula (VI) (hereinafter referred to as compound (VI)). The DMSO oxidation can be carried out by a known method. For example, the compound (V) is dissolved in DMSO alone or in a mixture of DMSO and a solvent that does not inhibit the oxidation (e.g., tetrahydrofuran, dichloromethane, chloroform, ethyl acetate, benzene, or ether), and diisopropylethylamine is added thereto generally in an amount of about 1 to 10 times by mole per mole of the compound (V). The amount of DMSO used in the above reaction is about 1 to about 20 mL based on 1 g of the compound (V). As the activating agent for DMSO, a sulfur trioxide-pyridine complex, oxalyl chloride, dicyclohexylcarbodiimide, acetic anhydride, or the like can be advantageously used. A sulfur trioxide-pyridine complex is particularly preferred.

Step c comprises treating the compound (VI) with sodium hydrogen sulfite, reacting the resulting product with sodium cyanide to obtain a cyanohydrin compound, hydrolyzing the cyanohydrin compound in the presence of an acid or alkali catalyst without purification to obtain a diastereomer mixture of α-hydroxy-β-amino acid, and re-adding an aforementioned amino-protecting group to the amino group of the α-hydroxy-β-amino acid in a similar manner, thereby producing a compound represented by the formula (VII) (hereinafter referred to as compound (VII)) as a diastereomer mixture.

The hydrolysis reaction is carried out by heating or by heating under reflux using an acid (e.g., hydrochloric acid, sulfuric acid, acetic acid, or formic acid) or an alkali (e.g., sodium hydroxide, potassium hydroxide, or barium hydroxide). The heating temperature is about 50 to about 100° C. As the solvent, a mixture of water and an organic solvent (e.g., dioxane or tetrahydrofuran) is preferably used.

Step d comprises condensing the compound (VII) with various amines to obtain a compound represented by the formula (VIII) (hereinafter referred to as compound (VIII)). A preferable amine can be suitably selected depending on the target compound. Examples of amines include ethylamine, propylamine, cyclopropylamine, butylamine, cyclobutylamine, methoxyethylamine, 2-phenoxyethylamine, 2-aminoindane, 2,2,2-trifluoroethylamine, and the like.

The condensation reaction is preferably carried out in the presence of a dehydration condensing agent, such as 1-ethyl-3-(3-dimethylaminopropyl)carbodiimide hydrochloride or N,N-dicyclohexylcarbodiimide. Examples of the organic solvent used in the condensation reaction include N,N-dimethylformamide, DMSO, tetrahydrofuran, dichloromethane, methanol, ethanol, benzene, toluene, ethyl acetate, and mixtures thereof; among which N,N-dimethylformamide is preferred. The reaction temperature is within the range of ice-cooling to room temperature.

Step e comprises deprotecting the amino-protecting group of the compound (VIII) under acidic conditions with hydrochloric acid to obtain an amine hydrochloride represented by the formula (IX) (hereinafter referred to as compound (IX)). The deprotection of the amino-protecting group can be carried out by a known method. For example, the compound (VIII) is dissolved in a commonly used organic solvent, and the mixture is stirred in the presence of an acid to remove the amino-protecting group. Examples of the acid include hydrochloric acid, trifluoroacetic acid, p-toluenesulfonic acid, and the like. Alternatively, a commercially available hydrochloric acid-ethyl acetate solution or hydrochloric acid-dioxane solution can be used to remove the amino-protecting group. The reaction temperature is within the range of ice-cooling to room temperature. Step f comprises condensing the compound (IX) with a compound represented by the formula (X) (hereinafter referred to as compound (X)) in the presence of triethylamine to obtain a compound represented by the formula (XI) (hereinafter referred to as compound (XI)).

The compound (X) can be produced, for example, according to the following general reaction route.

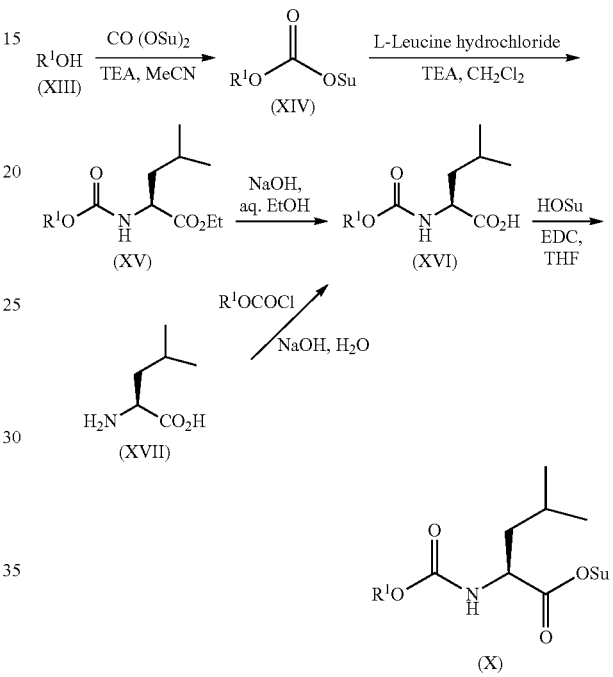

wherein each group is as defined above.

An alcohol represented by the formula (XIII) (hereinafter referred to as compound (XIII)) is reacted with di(N-succinimidyl) carbonate to obtain a mixed carbonate ester represented by the formula (XIV). The mixed carbonate ester is then condensed with L-leucine ethyl ester hydrochloride in the presence of triethylamine to obtain a compound represented by the formula (XV). Alkali saponification of the compound (XV) yields a compound represented by the formula (XVI) (hereinafter referred to as compound (XVI)). Alternatively, the compound (XVI) can be obtained by direct reaction between L-leucine and chloroformate. The compound (XVI) is reacted with hydroxysuccinimide (HOSu) to obtain a succinimide ester represented by the formula (X) (hereinafter referred to as compound (X)).

Step g comprises oxidizing the compound (XI) to obtain a compound represented by the formula (XII) (hereinafter referred to as compound (XII)). The oxidation reaction is carried out by a known method, such as oxidation classified as chromic acid oxidation, including pyridinium dichromate (PDC) oxidation, pyridinium chlorochromate (PCC) oxidation, Jones oxidation, and Collins oxidation; oxidation classified as DMSO oxidation, including Swern oxidation, DMSO/sulfur trioxide-pyridine complex oxidation, DMSO/dicyclohexylcarbodiimide oxidation, and DMSO/oxalyl chloride oxidation; Dess-Martin oxidation using a Dess-Martin reagent (Dess-Martin periodinane); hypohalous acid oxidation; or N-halogenocarboxylic acid amide oxidation; among which Dess-Martin oxidation is particularly preferred. When Dess-Martin oxidation is employed, the compound (XI) is dissolved in a commonly used organic solvent, and a Dess-Martin reagent is added thereto. Examples of the commonly used organic solvent include commonly used solvents that do not adversely affect the reaction, and mixtures of such solvents, such as dichloromethane, N,N-dimethylformamide, DMSO, tetrahydrofuran, methanol, ethanol, benzene, toluene, and ethyl acetate; among which dichloromethane is preferred. The amount of Dess-Martin reagent used is about 1- to 20-fold molar equivalents, preferably 1- to 3-fold molar equivalents, of the compound (XI). The reaction temperature is not particularly limited, and is within the range of ice-cooling to room temperature. The thus-obtained compound (XII) can be separated and purified by a known method, such as concentration, concentration under reduced pressure, solvent extraction, crystallization, recrystallization, solvent transfer, or chromatography. The compound (XII) is represented by the general formula (I).

Each of the above steps is carried out in the presence of a commonly used solvent that does not adversely affect the reaction, or a mixture of such solvents. Examples of the solvent that does not adversely affect the reaction include dichloromethane, N,N-dimethylformamide, DMSO, tetrahydrofuran, methanol, ethanol, benzene, toluene, ethyl acetate, and the like.

Among the compounds represented by the general formula (I) produced by the above-described method, for example, the following compounds are preferably contained in the composition for treating and/or preventing peripheral nerve disorder of the present invention:

((S)-1-((((1S)-1-benzyl-2,3-dioxo-3-(ethylamino) propyl) amino) carbonyl)-3-methylbutyl) carbamic acid 2-methoxyethyl ester (compound 1; the structural formula is shown below),

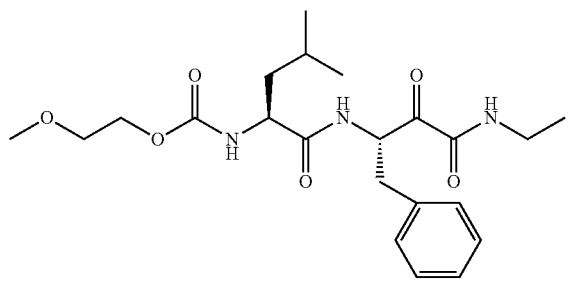 [SMILES: CCNC(=O)C(=O)[C@H](Cc1ccccc1)NC(=O)[C@H](CC(C)C)NC(=O)OCCOC]

((1S)-1-((((1S)-1-benzyl-2,3-dioxo-3-(ethylamino) propyl) amino) carbonyl)-3-methylbutyl) carbamic acid (3S)-tetrahydrofuran-3-yl ester (compound 2; the structural formula is shown below),

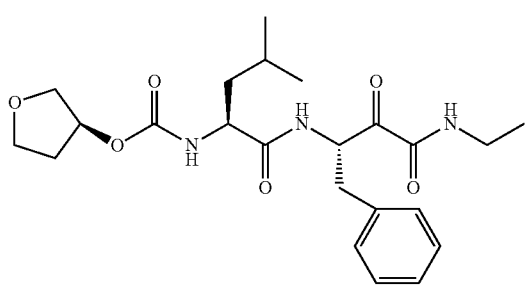 [SMILES: CCNC(=O)C(=O)[C@H](Cc1ccccc1)NC(=O)[C@H](CC(C)C)NC(=O)O[C@H]1CCOC1]

((1S)-1-((((1S)-1-benzyl-2,3-dioxo-3-(ethylamino) propyl) amino) carbonyl)-3-methylbutyl) carbamic acid tetrahydro-4H-pyran-4-yl ester (compound 3; the structural formula is shown below),

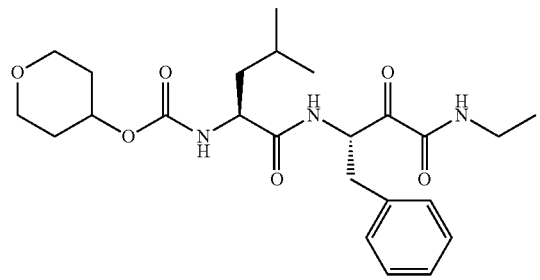 [SMILES: CCNC(=O)C(=O)[C@H](Cc1ccccc1)NC(=O)[C@H](CC(C)C)NC(=O)OC1CCOCC1]

((1S)-1-((((1S)-1-benzyl-2,3-dioxo-3-(cyclopropylamino) prop)amino) carbonyl))-3-methylbutyl) carbamic acid 2-methoxyethyl ester (compound 4; the structural formula is shown below),

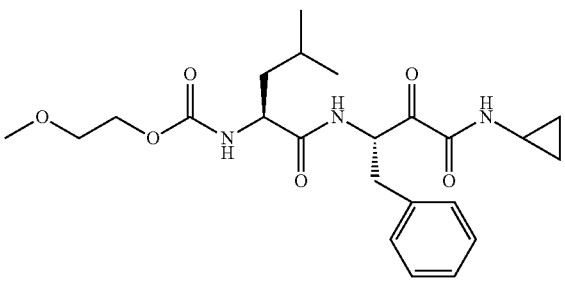 [SMILES: COCCOC(=O)N[C@@H](CC(C)C)C(=O)N[C@@H](Cc1ccccc1)C(=O)C(=O)NC1CC1]

((1S)-1-((((1S)-1-benzyl-3-(cyclopropylamino)-2,3-dioxo-propyl)amino) carbonyl)-3-methylbutyl) carbamic acid (3S)-tetrahydrofuran-3-yl ester (compound 5; the structural formula is shown below),

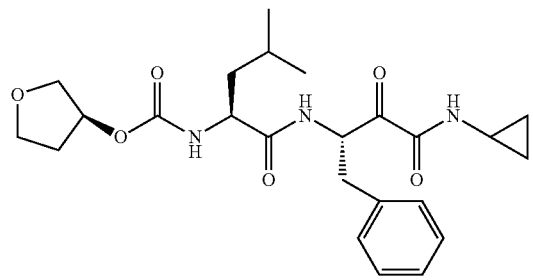 [SMILES: CC(C)C[C@H](NC(=O)O[C@H]1CCOC1)C(=O)N[C@@H](Cc1ccccc1)C(=O)C(=O)NC1CC1]

((1S)-1-((((1S)-1-benzyl-3-cyclopropylamino-2,3-dioxo-propyl)amino) carbonyl)-3-methylbutyl) carbamic acid tetrahydro-4H-pyran-4-yl ester (compound 6; the structural formula is shown below),

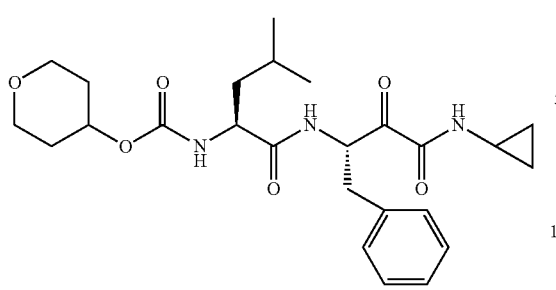

((1S)-1-(((((1S)-1-benzyl-2,3-dioxo-3-(propylamino) propyl)amino) carbonyl)-3-methylbutyl) carbamic acid 2-methoxyethyl ester (compound 7; the structural formula is shown below),

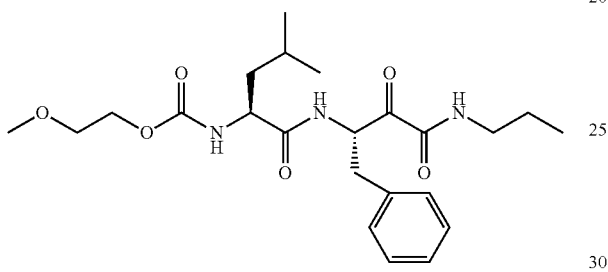

((1S)-1-(((((1S)-1-benzyl-2,3-dioxo-3-(cyclobutylamino) prop)amino) carbonyl)-3-methylbutyl) carbamic acid 2-methoxyethyl ester (compound 8; the structural formula is shown below),

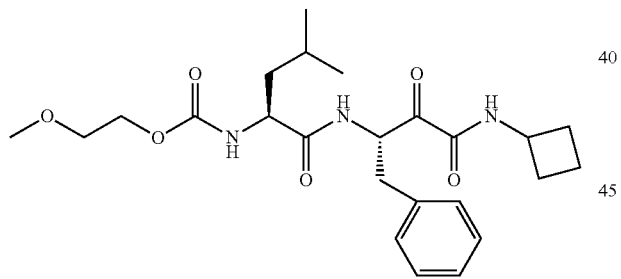

((1S)-1-(((((1S)-1-benzyl-3-butylamino-2,3-dioxopropyl)amino) carbonyl)-3-methylbutyl) carbamic acid 2-methoxyethyl ester (compound 9; the structural formula is shown below),

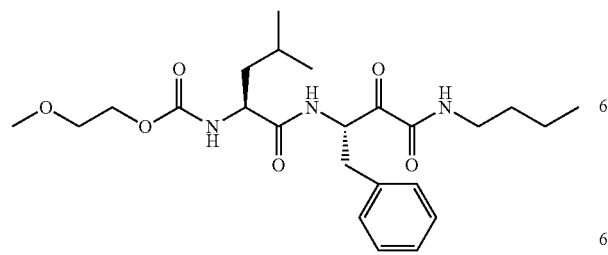

((1S)-1-(((((1S)-1-benzyl-2,3-dioxo-3-(2,2,2-trifluoroethylamino)prop)amino) carbonyl))-3-methylbutyl) carbamic acid 2-methoxyethyl ester (compound 10; the structural formula is shown below),

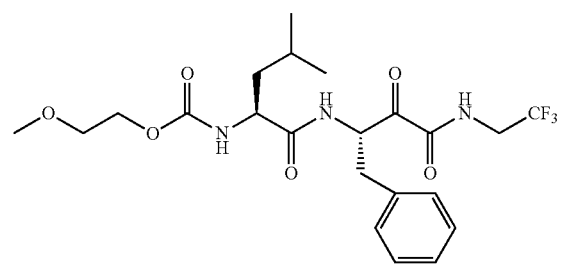 [SMILES: COCCOC(=O)N[C@@H](CC(C)C)C(=O)N[C@@H](Cc1ccccc1)C(=O)C(=O)NCC(F)(F)F]

((1S)-1-(((((1S)-1-benzyl-2,3-dioxo-3-(2-indanylamino) propyl)amino) carbonyl)-3-methylbutyl) carbamic acid 2-methoxyethyl ester (compound 11; the structural formula is shown below),

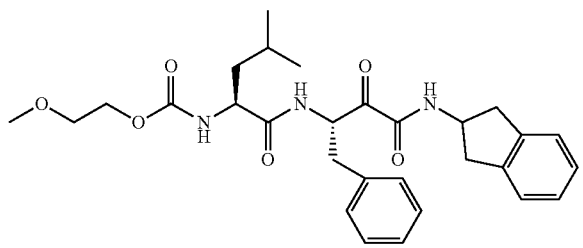 [SMILES: COCCOC(=O)N[C@@H](CC(C)C)C(=O)N[C@@H](Cc1ccccc1)C(=O)C(=O)NC1Cc2ccccc2C1]

((1S)-1-(((((1S)-1-benzyl-2,3-dioxo-3-(2-methoxyethylamino) propyl)amino) carbonyl)-3-methylbutyl) carbamic acid 2-methoxyethyl ester (compound 12; the structural formula is shown below),

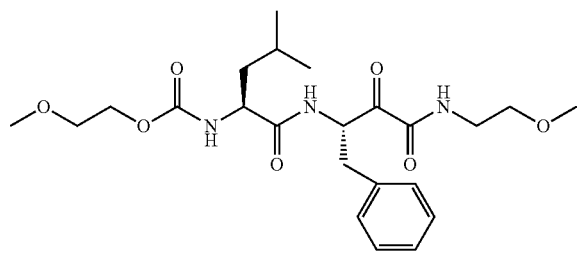

((1S)-1-(((((1S)-2,3-dioxo-3-ethylamino-1-(phenylethyl) propyl)amino) carbonyl)-3-methylbutyl) carbamic acid 2-methoxyethyl ester (compound 13; the structural formula is shown below),

17

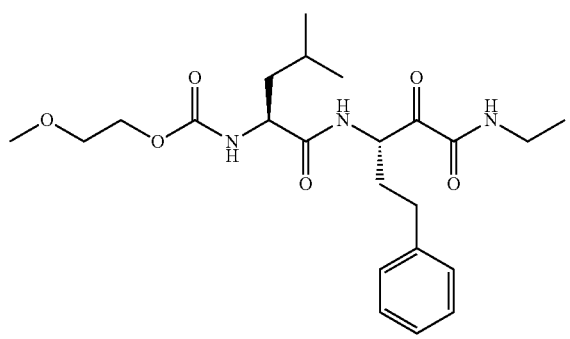 [SMILES: CCNC(=O)C(=O)[C@H](CCc1ccccc1)NC(=O)[C@H](CC(C)C)NC(=O)OCCOC]

((1S)-1-((((1S)-2,3-dioxo-3-ethylamino-1-(phenylethyl) propyl)amino) carbonyl)-3-methylbutyl) carbamic acid (3S)-tetrahydrofuran-3-yl ester (compound 14; the structural formula is shown below),

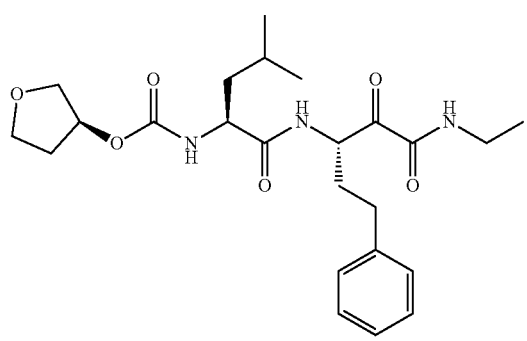 [SMILES: CCNC(=O)C(=O)[C@H](CCc1ccccc1)NC(=O)[C@H](CC(C)C)NC(=O)O[C@H]1CCOC1]

((1S)-1-((((1S)-2,3-dioxo-3-cyclopropylamino-1-(phenylethyl) propyl)amino) carbonyl)-3-methylbutyl) carbamic acid 2-methoxyethyl ester (compound 15; the structural formula is shown below),

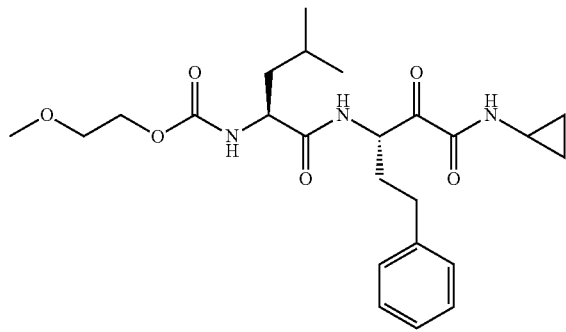 [SMILES: COCCOC(=O)N[C@@H](CC(C)C)C(=O)N[C@@H](CCc1ccccc1)C(=O)C(=O)NC1CC1]

18

((1S)-1-((((1S)-2,3-dioxo-3-cyclopropylamino-1-(phenylethyl) propyl)amino) carbonyl)-3-methylbutyl) carbamic acid (3S)-tetrahydrofuran-3-yl ester (compound 16; the structural formula is shown below),

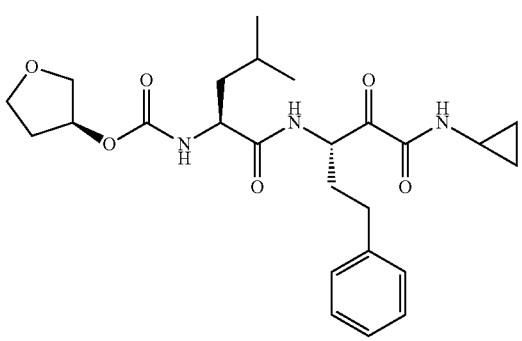 [SMILES: CC(C)C[C@H](NC(=O)O[C@H]1CCOC1)C(=O)N[C@@H](CCc1ccccc1)C(=O)C(=O)NC1CC1]

((1S)-1-((((1S)-1-benzyl-2,3-dioxo-3-(cyclopropylamino) propyl)amino) carbonyl)-3-methylbutyl) carbamic acid 8-methoxy-3,6-dioxaoctyl ester (compound 18; the structural formula is shown below),

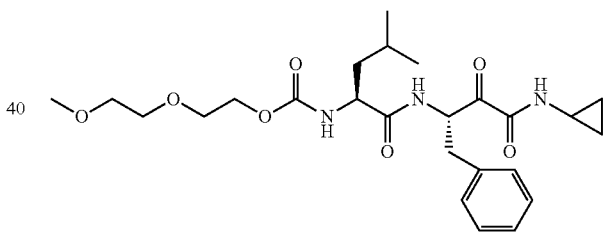

((1S)-1-((((1S)-1-benzyl-2,3-dioxo-3-(cyclopropylamino) propyl)amino)carbonyl)-3-methylbutyl)carbamic acid 8-methoxy-3,6-dioxaoctyl ester (compound 18; the structural formula is shown below),

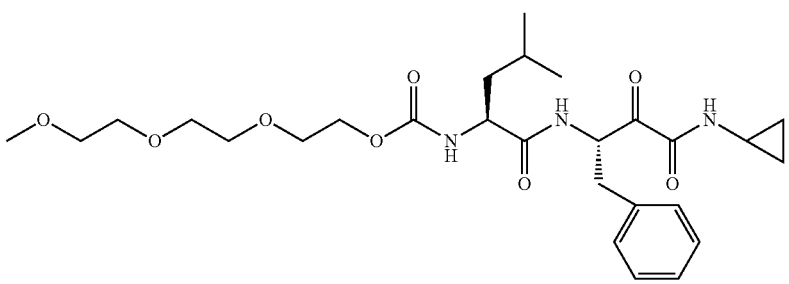 [SMILES: COCCOCCOCCOC(=O)N[C@@H](CC(C)C)C(=O)N[C@@H](Cc1ccccc1)C(=O)C(=O)NC1CC1]

((1S)-1-((((1S)-1-benzyl-2,3-dioxo-3-(cyclopropylamino)
propyl)amino) carbonyl)-3-methylbutyl) carbamic acid
11-methoxy-3,6,9-trioxaundecanyl ester (compound 19;
the structural formula is shown below),

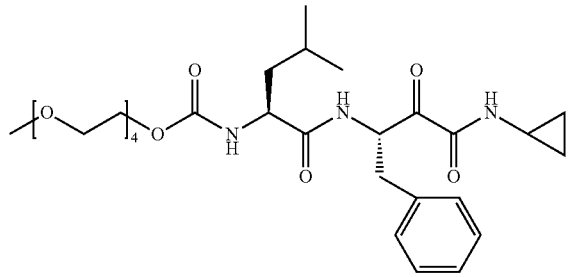

((S)-1-((((S)-1-benzyl-2,3-dioxo-3-(cyclopropylamino) pro-
p)amino) carbonyl))-3-methylbutyl) carbamic acid
14-methoxy-3,6,9,12-tetraoxatetradecanyl ester (compound
20; the structural formula is shown below),

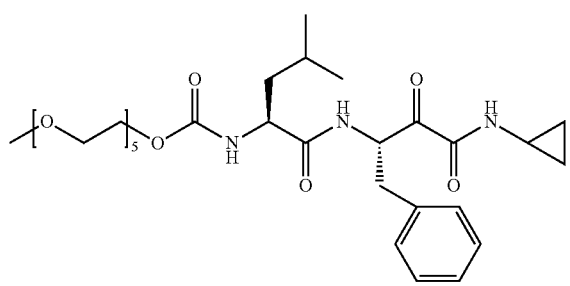

((1S)-1-((((1S)-2,3-dioxo-1-(2-methylpropyl)-3-(2-phe-
noxyethyl)aminopropyl)amino) carbonyl)-3-methylbutyl)
carbamic acid 2-methoxyethyl ester (compound 21; the
structural formula is shown below),

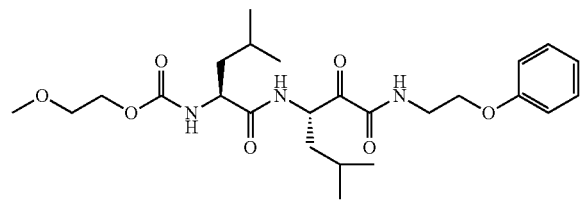 [SMILES: COCCOC(=O)N[C@@H](CC(C)C)C(=O)N[C@@H](CC(C)C)C(=O)C(=O)NCCOc1ccccc1]

((1S)-1-((((1S)-2,3-dioxo-1-(2-methylpropyl)-3-(2-phe-
noxyethyl)aminopropyl)amino) carbonyl)-3-methylbutyl)
carbamic acid 5-methoxy-3-oxapentyl ester (compound
22; the structural formula is shown below), ((1S)-1-((((1RS)-β-amino-1-benzyl-2,3-dioxopropyl)
amino) carbonyl)-3-methylbutyl) carbamic acid
5-methoxy-3-oxapentyl ester (compound 23; the struc-
tural formula is shown below),

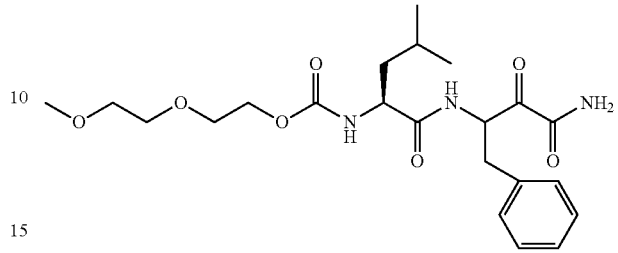

((1S)-1-((((1S)-1-benzyl-3-(cyclopropylamino)-2,3-dioxo-
propyl)amino) carbonyl)-3-methylbutyl) carbamic acid
2-(pyridin-2-yl)ethyl ester (compound 24; the structural
formula is shown below),

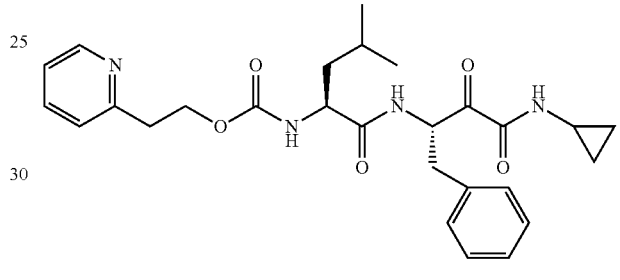

((1S)-1-((((1S)-1-benzyl-3-(cyclopropylamino)-2,3-dioxo-
propyl)amino) carbonyl)-3-methylbutyl) carbamic acid
2-(6-methylpyridin-2-yl)ethyl ester (compound 25; the
structural formula is shown below),

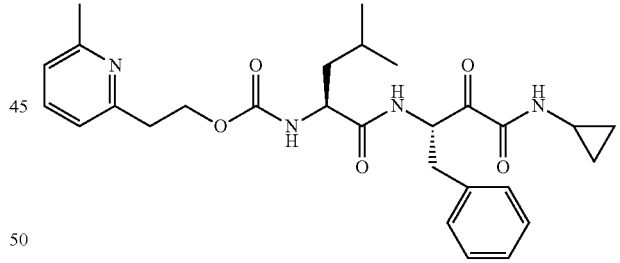

((1S)-1-((((1S)-1-benzyl-3-(cyclopropylamino)-2,3-dioxo-
propyl)amino)-3-methylbutyl) carbamic acid

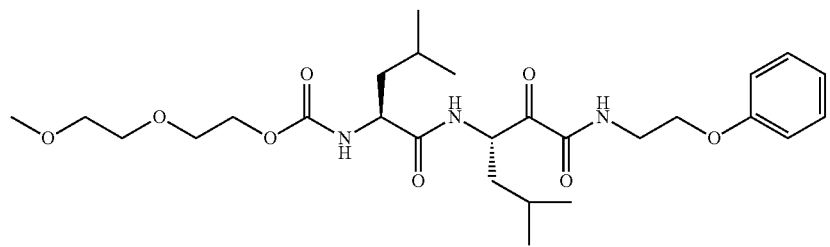 [SMILES: COCCOCCOC(=O)N[C@@H](CC(C)C)C(=O)N[C@@H](CC(C)C)C(=O)C(=O)NCCOc1ccccc1]

2-(5-ethylpyridin-2-yl)ethyl ester (compound 26; the structural formula is shown below),

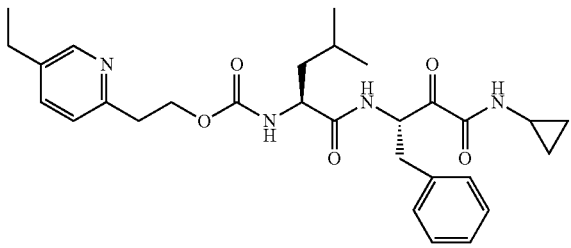 [SMILES: CCc1ccc(CCOC(=O)N[C@@H](CC(C)C)C(=O)N[C@@H](Cc2ccccc2)C(=O)C(=O)NC2CC2)nc1]

((1S)-1-((((1S)-1-benzyl-3-(cyclopropylamino)-2,3-dioxopropyl)amino) carbonyl)-3-methylbutyl) carbamic acid 2-tert-butoxyethyl ester (compound 27; the structural formula is shown below),

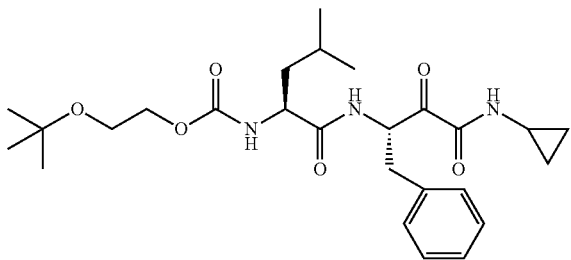 [SMILES: CC(C)C[C@H](NC(=O)OCCOC(C)(C)C)C(=O)N[C@@H](Cc1ccccc1)C(=O)C(=O)NC1CC1]

and
((1S)-1-((((1S)-1-benzyl-3-(cyclopropylamino)-2,3-dioxopropyl)amino) carbonyl)-3-methylbutyl) carbamic acid 2-isopropoxyethyl ester (compound 28; the structural formula is shown below).

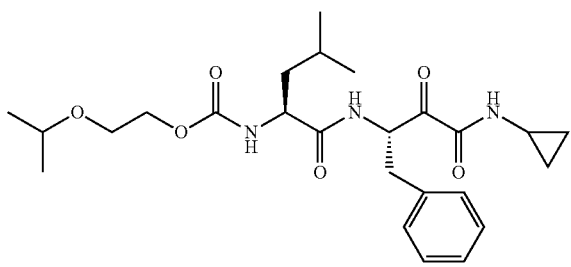 [SMILES: CC(C)C[C@H](NC(=O)OCCOC(C)C)C(=O)N[C@@H](Cc1ccccc1)C(=O)C(=O)NC1CC1]

More preferred among these are the compounds 4, 17, 18, 19, or 24; and still more preferred is the compound 17.

PTL 1 (JP2006-76989A) mentioned above discloses the specific production methods and physical properties of the compounds 1 to 28.

These compounds have excellent calpain inhibitory activity, as shown in PTL 1, and can be preferably used as active ingredients of the composition for treating and/or preventing peripheral nerve disorder of the present invention.

The composition for treating and/or preventing peripheral nerve disorder of the present invention can be used not only for humans, but also for non-human mammals (e.g., rats, mice, rabbits, cattle, pigs, dogs, and cats).

In addition, the above compounds are advantageous for treating or preventing peripheral nerve disorder, because they are excellent in tissue transfer and absorbability, are significantly less toxic, and are highly safe. These advantages make the composition for treating and/or preventing peripheral nerve disorder of the present invention, which comprises such a compound, favorable. The composition for treating and/or preventing peripheral nerve disorder of the present invention can be administered systemically or locally. Systemic administration includes, for example, oral administration, and parenteral administration, such as intravenous injection, subcutaneous injection, and intramuscular injection. Local administration includes, for example, transdermal administration, mucosal administration, intranasal administration, ocular administration, etc.

The composition for treating and/or preventing peripheral nerve disorder of the present invention may be a composition (in particular, a pharmaceutical composition) comprising the compound and a pharmaceutically acceptable carrier or additive, etc. The composition may contain other pharmacologically active substances and pharmaceutically acceptable optional components, to the extent that the effect of the present invention is not impaired. A person skilled in the art can suitably select such carriers, additives, optional components, other pharmacologically active substances, etc., depending on the purpose, and can also suitably determine their amounts and other conditions.

When the composition for treating and/or preventing peripheral nerve disorder of the present invention is in the form of a pharmaceutical composition, its dosage form includes, but is not limited thereto, solid preparations (e.g., powders, granules, tablets, capsules, and suppositories), liquid preparations (e.g., syrups, injections, intravenous drips, eye drops, and nasal drops), and the like. Among these, preparations that can be orally administered (oral preparations), injections, and drops are preferred. These can be produced by a known method.

For example, in the production of granules or tablets, any dosage form can be prepared with the use of pharmaceutically acceptable additives, such as excipients (e.g., lactose, sucrose, glucose, starch, crystalline cellulose, hydroxypropyl methyl cellulose, hydroxyethyl cellulose, hydroxypropyl cellulose, carboxymethyl cellulose, and methyl cellulose), lubricants (e.g., magnesium stearate, talc, stearic acid, and calcium stearate), disintegrators (e.g., starch, carmellose sodium, and calcium carbonate), or binders (e.g., starch paste, hydroxypropylcellulose solution, carmellose solution, gum arabic solution, gelatin solution, and sodium alginate solution). Further, the granules and tablets may be coated with a suitable coating agent (e.g., gelatin, sucrose, gum arabic, or carnauba wax) or a suitable enteric coating agent (e.g., cellulose acetate phthalate, methacrylic copolymer, hydroxypropylcellulose phthalate, or carboxymethylethylcellulose).

In the production of capsules, a known excipient, such as magnesium stearate, calcium stearate, talc, or light silicic acid anhydride, all of which can improve flowability and lubricity; crystalline cellulose and lactose, both of which can increase flowability under pressure; an aforementioned disintegrator; or the like is suitably selected; then mixed or granulated homogenously with the compound of the present invention; and filled in capsules. Alternatively, the granulated products may be coated with a suitable coating agent, and then filled in capsules, or may be encapsulated with a suitable capsule base (e.g., gelatin) having increased plasticity endowed with addition of glycerin, sorbitol, or the like. The capsules may contain, if necessary, coloring agents, preservatives (e.g., sulfur dioxide, and parabens such as methyl parahydroxybenzoate, ethyl parahydroxybenzoate, and propyl parahydroxybenzoate), and the like. The capsules may be in the form of enteric-coated capsules, gastroresistant capsules, or release-controlled capsules, as well as general capsules. Enteric-coated capsules can be prepared by encapsulating the compound of the present invention coated with an enteric coating agent, or a mixture of the compound of the present invention and an aforementioned suitable excipient, into regular capsules. Alternatively, they can be prepared by encapsulating the compound of the present invention or a mixture of the compound of the present invention and an aforementioned suitable excipient into capsules coated with an enteric coating agent or capsules made from an enteric polymer as a base material.

In the production of suppositories, suppository bases (e.g., cacao butter and macrogol) can be suitably selected and used.

In the production of syrups, stabilizers (e.g., sodium edetate), suspending agents (e.g., gum arabic and carmellose), corrigents (e.g., simple syrup and glucose), perfumes, and the like can be suitably used. A person skilled in the art can suitably select such optional components depending on the purpose, and can also suitably determine their amounts and other conditions.

Injections, intravenous drips, eye drops, or nasal drops of the present invention can be produced by dissolving or dispersing the above compound in a solution suitably containing pharmaceutically acceptable additives, such as isotonic agents (e.g., sodium chloride, potassium chloride, glycerin, mannitol, sorbitol, boric acid, borax, glucose, and propylene glycol), buffers (e.g., phosphate buffer, acetate buffer, borate buffer, carbonate buffer, citrate buffer, Tris buffer, glutamate buffer, and epsilon-aminocaproic acid buffer), preservatives (e.g., methyl parahydroxybenzoate, ethyl parahydroxybenzoate, propyl parahydroxybenzoate, chlorobutanol, benzyl alcohol, benzalkonium chloride, sodium dehydroacetate, sodium edetate, boric acid, and borax), thickeners (e.g., hydroxyethylcellulose, hydroxypropylcellulose, polyvinyl alcohol, and polyethylene glycol), stabilizers (e.g., sodium hydrogen sulfite, sodium thiosulfate, sodium edetate, sodium citrate, ascorbic acid, and dibutylhydroxytoluene), and pH adjusters (e.g., hydrochloric acid, sodium hydroxide, phosphoric acid, and acetic acid). A person skilled in the art can suitably select such pharmaceutically acceptable additives depending on the purpose, and can also suitably determine their amounts and other conditions.

Although the amount of additives in the above-mentioned injections, eye drops, or nasal drops depends on the type and application of additives to be added, the additive content may be determined so that the purpose of the additives can be achieved.

The dosage of the composition for treating and/or preventing peripheral nerve disorder of the present invention depends on the degree of peripheral nerve disorder progression in the patient to be administered, age, administration route, and other conditions; for example, the amount of the above compound, which is an active ingredient of the composition, is about 0.1 to about 2,000 mg, and preferably about 1 to about 1,500 mg, per day. In particular, in the case of oral administration or intravascular administration (preferably intravenous administration), the dosage per day is, for example, about 10 to about 1,500 mg, preferably about 20 to about 1,500 mg, more preferably about 50 to about 1,200 mg, and even more preferably about 100 to about 1,000 mg. The composition for treating and/or preventing peripheral nerve disorder of the present invention may be administered in several divided doses (preferably 1, 2, or 3 doses) per day, for example.

Further, the amount of the compound contained in the composition for treating and/or preventing peripheral nerve disorder of the present invention as an active ingredient is not particularly limited. For example, the compound can be obtained in an amount of 0.01 to 100 wt %, preferably 0.1 to 99 wt %, based on the entire composition.

The diseases to be treated or prevented by the composition for treating and/or preventing peripheral nerve disorder of the present invention are not particularly limited insofar as they are peripheral nerve disorders. Examples include mechanical or entrapment neuropathy, metabolic neuropathy, infectious neuropathy, drug-induced peripheral nerve disorders, and the like. Specific examples of mechanical or entrapment neuropathy include carpal tunnel syndrome, cubital tunnel syndrome, sciatic nerve paralysis, peroneal nerve paralysis, tarsal tunnel syndrome, severed nerve from injury, and the like. Examples of metabolic neuropathy include diabetic neuropathy, uremic neuropathy, neuropathy due to vitamin deficiency, and the like. Examples of infectious neuropathy include nerve disorder as an aftereffect from shingles, and the like. Specific examples of drug-induced peripheral nerve disorders include peripheral nerve disorders caused by taxane-based therapeutic agent (e.g. paclitaxel, docetaxel, etc.), microtubule polymerization inhibitors, and the like. Further, although the present invention is not particularly limited, the composition for treating and/or preventing peripheral nerve disorder of the present invention is particularly effective for the treatment of physically damaged peripheral nerves. Further, among peripheral nerve disorders, the composition of the present invention is preferably used for sciatic nerve disorders.

Furthermore, this composition may contribute to fetal neuron network construction by being administered to a mother's womb or fetus during the fetal period. Therefore, this composition is capable of treatment and/or prevention of fetal neuron network construction disorders during the fetal period. Therefore, this composition is also effective for treatment and/or prevention of fetal neuron network construction disorders during the fetal period.

Examples of fetal neuron network construction disorders during the fetal period include genetic disorders of midline crossing, genetic disorders of neuron migration, autism spectrum disorders, epilepsy, and the like. Specific examples of genetic disorders of midline crossing include congenital mirror movements, horizontal gaze palsy with progressive scoliosis, dyslexia, and the like. Specific examples of genetic disorders of neuron migration include Kallmann's syndrome, Hirschsprung's disease, and the like. Specific examples of autism spectrum disorders and epilepsy include autism spectrum disorders, epilepsy, fragile X syndrome, and the like.

The compound described above contained in the composition for treating and/or preventing peripheral nerve disorder of the present invention also has an advantage that it has particularly low toxicity and relatively low side effects, compared with other calpain inhibitors. Further, the compound has a peripheral nerve regeneration facilitation effect higher than those of other calpain inhibitors, and therefore is capable of significantly regenerating peripheral nerves that have significantly decreased regenerative capacity.

EXAMPLES

The present invention is described below in more detail. However, the scope of the present invention is not limited to the following Examples. In the following study, well-known textbooks in this field (e.g., Molecular Cloning: A Laboratory Manual (Cold Spring Harbor Laboratory Press), *Kyoushouten Kenbikyou Katsuyou Protocol* [Protocol for Practical Use of Confocal Microscope] (Yodosha Company Limited), *Tanpakushitsu Jikken Handbook* [Handbook for Experiments on Proteins] (Yodosha Company Limited), and *Nou Shinkei Kenkyu no Susumekata* [How to Proceed with Research on Brain and Nerves](Yodosha Company Limited)) may appropriately be referred to for basic operations, etc.

Synthesis of Each Compound

Compounds 1 to 28 were synthesized to obtain crystals according to the method disclosed in Patent Literature 1 above. Specifically, the synthesis was performed in the following manner. In the analytical values of the following compounds, the melting point was measured using a Yanaco MP-500V (uncorrected). Nuclear magnetic resonance spectra (NMR) were recorded on a Varian Gemini 2000 (300 MHz). Matrix-assisted laser desorption/ionization time-of-flight mass spectra (MALDI-TOF MS) were obtained on a PerSeptive Voyager DE Mass Spectrometer. The mass numbers were corrected with a standard substance (α-cyano-4-hydroxycinnamic acid). The ratio is a volume ratio.

Reference Example 1

N-((2-Methoxyethoxy)carbonyl)-L-leucine N-hydroxysuccinimide ester (1) L-Leucine (25 g, 0.19 mol) was dissolved in a 2M aqueous sodium hydroxide solution (0.12 L), to which chloroformic acid 2-methoxyethyl ester (30 g, 0.22 mol) and a 1M aqueous sodium hydroxide solution were simultaneously and slowly added under ice-cold conditions. This solution was stirred at room temperature for 18 hours, followed by dilution with water (600 mL) and washing with diethyl ether (2×200 mL). The aqueous layer was cooled in an ice bath, and the pH was adjusted to 3 with 6M hydrochloric acid. This solution was extracted with ethyl acetate (5×150 mL). The organic layer was dehydrated with anhydrous magnesium sulfate and concentrated in vacuo to yield N-((2-methoxyethoxy)carbonyl)-L-leucine (41 g, 92%) as a colorless oil.

(2) N-((2-Methoxyethoxy)carbonyl)-L-leucine (20 g, 86 mmol) and N-hydroxysuccinimide (13 g, 0.11 mmol) were dissolved in tetrahydrofuran (200 mL), and a suspension of 1-ethyl-3-(3-dimethylaminopropyl)carbodiimide hydrochloride (21 g, 0.11 mol) in dichloromethane (200 mL) was added thereto. This solution was stirred at room temperature for 18 hours and concentrated in vacuo. The residue was dissolved in ethyl acetate (300 mL), and the solution was washed with 1M hydrochloric acid, saturated aqueous sodium hydrogen carbonate solution, and saturated saline solution, dehydrated with anhydrous magnesium sulfate, and concentrated in vacuo to yield the title compound (27 g, 95%) as a colorless oil.

$^1$H-NMR (300 MHz, DMSO-$d_6$) δ0.89 (d, 3H, J=6.6), 0.93 (d, 3H, J=6.6), 1.57-1.84 (m, 3H), 2.81 (s, 4H), 3.26 (s, 3H), 3.51 (t, 2H, J=4.7), 4.10 (t, 2H, J=4.7), 4.40 (m, 1H), 8.04 (d, 1H, J=8.1).

Reference Example 2

N-(((3S)-Tetrahydrofuran-3-yloxy)carbonyl)-L-leucine N-hydroxysuccinimide ester (1) N,N'-Disuccinimidyl carbonate (4.3 g, 17 mmol) and triethylamine (4.4 g, 17 mmol, 4.8 mL) were added at room temperature to a solution of (S)-3-hydroxytetrahydrofuran (1.0 g, 11 mmol) in acetonitrile (50 mL) with stirring. This solution was stirred at room temperature for 18 hours, and concentrated in vacuo. A saturated aqueous sodium hydrogen carbonate solution (100 mL) was added to the residue, and the mixture was extracted with ethyl acetate (200 mL). The organic layer was washed with a saturated saline solution, dehydrated with anhydrous magnesium sulfate, and concentrated in vacuo to quantitatively yield N-succinimidyl (3S)-3-tetrahydrofuranyl carbonate (2.6 g) as a brown oil.

(2) A solution of N-succinimidyl (3S)-3-tetrahydrofuranyl carbonate (2.6 g, 11 mmol) in dichloromethane (20 mL) was added to a solution of L-leucine ethyl ester hydrochloride (2.7 g, 14 mmol) and triethylamine (2.9 g, 28 mmol) in dichloromethane (50 mL). This reaction solution was stirred at room temperature for 18 hours, and concentrated in vacuo. The residue was dissolved in ethyl acetate (200 mL), and the solution was washed with 1M hydrochloric acid, saturated aqueous sodium hydrogen carbonate solution, and saturated saline solution, dehydrated with anhydrous magnesium sulfate, and concentrated in vacuo. The residue was washed with hexane to yield N-(((3S)-tetrahydrofuran-3-yloxy)carbonyl)-L-leucine ethyl ester (3.1 g, 98%) as a white solid.

(3) A 1M aqueous sodium hydroxide solution (33 mL) was added to a solution of N-(((3S)-tetrahydrofuran-3-yloxy)carbonyl)-L-leucine ethyl ester (2.9 g, 11 mmol) in ethanol (100 mL). This solution was stirred for 3 hours under ice-cold conditions, after which the pH was adjusted to 3 with hydrochloric acid. Ethanol was distilled off in vacuo, and the residue was extracted with ethyl acetate. The organic layer was washed with 1M hydrochloric acid and saturated saline solution, dehydrated with anhydrous magnesium sulfate, and concentrated in vacuo. The residue was crystallized from a liquid mixture of ethyl acetate and hexane, thereby yielding N-(((3S)-tetrahydrofuran-3-yloxy)carbonyl)-L-leucine (2.6 g, 85%) as a colorless crystal.

Melting point: 94.9-96.0° C.

(4) The reaction was performed as in Reference Example 1 (2) by using N-(((3S)-tetrahydrofuran-3-yloxy)carbonyl)-L-leucine in place of N-((2-methoxyethoxy)carbonyl)-L-leucine, thereby yielding the title compound as a colorless oil.

$^1$H-NMR (300 MHz, DMSO-$d_6$) δ0.89 (d, 3H, J=6.0), 0.92 (d, 3H, J=6.3), 1.55-1.82 (m, 3H), 1.88 (m, 1H), 2.12 (m, 1H), 2.81 (s, 4H), 3.64-3.84 (m, 4H), 4.39 (m, 1H), 5.15 (m, 1H), 8.04 (d, 1H, J=7.8).

Reference Example 3

N-((Tetrahydro-4H-pyran-4-yloxy) carbonyl)-L-leucine N-hydroxysuccinimide ester (1) The reaction was performed as in Reference Example 2 (1) by using 4-hydroxytetrahydro-4H-pyran in place of (S)-3-hydroxytetrahydrofuran, thereby yielding N-succinimidyl tetrahydro-4H-pyran-4-ylcarbonate as a brown oil.

(2) The reaction was performed as in Reference Example 2 (2) by using N-succinimidyl tetrahydro-4H-pyran-4-ylcarbonate in place of N-succinimidyl (3S)-3-tetrahydrofuranyl carbonate, thereby yielding N-((tetrahydro-4H-pyran-4-yloxy)carbonyl)-L-leucine ethyl ester as a colorless solid.

(3) The reaction was performed as in Reference Example 2 (3) by using N-((tetrahydro-4H-pyran-4-yloxy)carbonyl)-L-leucine ethyl ester in place of N-(((3S)-tetrahydrofuran-3-yloxy) carbonyl)-L-leucine ethyl ester, thereby yielding N-((tetrahydro-4H-pyran-4-yloxy)carbonyl)-L-leucine as a colorless solid.

(4) The reaction was performed as in Reference Example 1 (2) by using N-((tetrahydro-4H-pyran-4-yloxy) carbonyl)-L-leucine in place of N-((2-methoxyethoxy)carbonyl)-L-leucine, thereby yielding the title compound as a colorless solid.

$^1$H-NMR (300 MHz, DMSO-$d_6$) δ0.89 (d, 3H, J=6.0), 0.92 (d, 3H, J=6.3), 1.43-1.93 (m, 7H), 2.80 (s, 4H), 3.42 (m, 2H), 3.78-3.82 (m, 2H), 4.39 (m, 1H), 4.72 (m, 1H), 7.94 (d, 1H, J=7.8).

Reference Example 4

N-((5-Methoxy-3-oxapentyloxy) carbonyl)-L-leucine N-hydroxysuccinimide ester (1) The reaction was performed as in Reference Example 2 (1) by using diethylene glycol monomethyl ether in place of (S)-3-hydroxytetrahydrofuran, thereby yielding 5-methoxy-3-oxapentyl N-succinimidyl carbonate as a colorless oil.

(2) The reaction was performed as in Reference Example 2 (2) by using 5-methoxy-3-oxapentyl N-succinimidyl carbonate in place of N-succinimidyl (3S)-3-tetrahydrofuranyl carbonate, thereby yielding N-((5-methoxy-3-oxapentyloxy) carbonyl)-L-leucine ethyl ester as a colorless oil.

(3) The reaction was performed as in Reference Example 2 (3) by using N-((5-methoxy-3-oxapentyloxy)carbonyl)-L-leucine ethyl ester in place of N-(((3S)-tetrahydrofuran-3-yloxy) carbonyl)-L-leucine ethyl ester, thereby yielding N-((5-methoxy-3-oxapentyloxy)carbonyl)-L-leucine as a colorless oil.

(4) The reaction was performed as in Reference Example 1 (2) by using N-((5-methoxy-3-oxapentyloxy) carbonyl)-L-leucine in place of N-((2-methoxyethoxy)carbonyl)-L-leucine, thereby yielding the title compound as a colorless oil.

$^1$H-NMR (300 MHz, DMSO-$d_6$) δ0.90 (dd, 6H, J=9.5, 6.5), 1.56-1.80 (m, 3H), 2.80 (s, 4H), 3.24 (s, 3H), 3.41-3.46 (m, 2H), 3.50-3.54 (m, 2H), 3.56-3.60 (m, 2H), 4.08-4.11 (m, 2H), 4.39 (m, 1H), 8.05 (d, 1H, J=7.8).

Reference Example 5

N-((8-Methoxy-3,6-dioxaoctyloxy)carbonyl)-L-leucine N-hydroxysuccinimide ester (1) The reaction was performed as in Reference Example 2 (1) by using triethylene glycol monomethyl ether in place of (S)-3-hydroxytetrahydrofuran, thereby yielding 8-methoxy-3,6-dioxaoctyl N-succinimidyl carbonate as a colorless oil.

(2) The reaction was performed as in Reference Example 2 (2) by using 8-methoxy-3,6-dioxaoctyl N-succinimidyl carbonate in place of N-succinimidyl (3S)-3-tetrahydrofuranyl carbonate, thereby yielding N-((8-methoxy-3,6-dioxaoctyloxy) carbonyl)-L-leucine ethyl ester as a colorless oil.

(3) The reaction was performed as in Reference Example 2 (3) by using N-((8-methoxy-3,6-dioxaoctyloxy) carbonyl)-L-leucine ethyl ester in place of N-(((3S)-tetrahydrofuran-3-yloxy) carbonyl)-L-leucine ethyl ester, thereby yielding N-((8-methoxy-3,6-dioxaoctyloxy) carbonyl)-L-leucine as a colorless oil.

(4) The reaction was performed as in Reference Example 1 (2) by using N-((8-methoxy-3,6-dioxaoctyloxy) carbonyl)-L-leucine in place of N-((2-methoxyethoxy)carbonyl)-L-leucine, thereby yielding the title compound as a colorless oil.

$^1$H-NMR (300 MHz, DMSO-$d_6$) δ0.89 (d, 3H, J=6.3), 0.92 (d, 3H, J=6.3), 1.56-1.82 (m, 3H), 2.81 (s, 4H), 3.24 (s, 3H), 3.43 (m, 2H), 3.52 (m, 6H), 3.59 (m, 2H), 4.10 (m, 2H), 4.40 (m, 1H), 8.06 (d, 1H, J=7.8).

Reference Example 6

N-((11-Methoxy-3,6,9-trioxaundecanyloxy)carbonyl)-L-leucine N-hydroxysuccinimide ester (1) The reaction was performed as in Reference Example 2 (1) by using tetraethylene glycol monomethyl ether in place of (S)-3-hydroxytetrahydrofuran, thereby yielding 11-methoxy-3,6,9-trioxaundecanyl N-succinimidyl carbonate as a colorless oil.

(2) The reaction was performed as in Reference Example 2 (2) by using 11-methoxy-3,6,9-trioxaundecanyl N-succinimidyl carbonate in place of N-succinimidyl (3S)-3-tetrahydrofuranyl carbonate, thereby yielding N-((11-methoxy-3,6,9-trioxaundecanyloxy)carbonyl)-L-leucine ethyl ester as a colorless oil.

(3) The reaction was performed as in Reference Example 2 (3) by using N-((11-methoxy-3,6,9-trioxaundecanyloxy) carbonyl)-L-leucine ethyl ester in place of N-(((3S)-tetrahydrofuran-3-yloxy)carbonyl)-L-leucine ethyl ester, thereby yielding N-((11-methoxy-3,6,9-trioxaundecanyloxy) carbonyl)-L-leucine as a colorless oil.

(4) The reaction was performed as in Reference Example 1 (2) by using N-((11-methoxy-3,6,9-trioxaundecanyloxy)carbonyl)-L-leucine in place of N-((2-methoxyethoxy)carbonyl)-L-leucine, thereby yielding the title compound as a colorless oil.

$^1$H-NMR (300 MHz, DMSO-$d_6$) δ0.91 (dd, 6H, J=9.3, 6.3), 1.56-1.77 (m, 3H), 2.81 (s, 4H), 3.24 (s, 3H), 3.41-3.44 (m, 2H), 3.49-3.52 (m, 10H), 3.59 (t, 2H, J=4.7), 4.08-4.11 (m, 2H), 4.38 (m, 1H), 8.06 (d, 1H, J=7.8).

Reference Example 7

N-((14-Methoxy-3,6,9,12-tetraoxatetradecanyloxy) carbonyl)-L-leucine N-hydroxysuccinimide ester (1) The reaction was performed as in Reference Example 2 (1) by using pentaethylene glycol monomethyl ether in place of (S)-3-hydroxytetrahydrofuran, thereby yielding 14-methoxy-3,6,9,12-tetraoxatetradecanyl N-succinimidyl carbonate as a colorless oil.

(2) The reaction was performed as in Reference Example 2 (2) by using 14-methoxy-3,6,9,12-tetraoxatetradecanyl N-succinimidyl carbonate in place of N-succinimidyl (3S)-3-tetrahydrofuranyl carbonate, thereby yielding N-((14-methoxy-3,6,9,12-tetraoxatetradecanyloxy) carbonyl)-L-leucine ethyl ester as a colorless oil.

(3) The reaction was performed as in Reference Example 2 (3) by using N-((14-methoxy-3,6,9,12-tetraoxatetradecanyloxy)carbonyl)-L-leucine ethyl ester) in place of N-(((3S)-tetrahydrofuran-3-yloxy)carbonyl)-L-leucine ethyl ester, thereby yielding N-((14-methoxy-3,6,9,12-tetraoxatetradecanyloxy)carbonyl)-L-leucine as a colorless oil.

(4) The reaction was performed as in Reference Example 1 (2) by using N-((14-methoxy-3,6,9,12-tetraoxatetradecanyloxy)carbonyl)-L-leucine in place of N-((2-methoxyethoxy)carbonyl)-L-leucine, thereby yielding the title compound as a colorless oil.

$^1$H-NMR (300 MHz, DMSO-$d_6$) δ0.89 (d, 3H, J=6.6), 0.92 (d, 3H, J=6.3), 1.57-1.82 (m, 3H), 2.81 (s, 4H), 3.24 (s, 3H), 3.43 (m, 2H), 3.51 (m, 14H), 3.59 (m, 2H), 4.10 (m, 2H), 4.40 (m, 1H), 8.05 (d, 1H, J=7.8).

Reference Example 8

(3S)-3-Amino-N-ethyl-2-hydroxy-4-phenylbutanamide hydrochloride (1) A solution of di-t-butyldicarbonate (140 g, 0.67 mol) in tetrahydrofuran (500 mL) and a 1M aqueous sodium hydroxide solution (660 mL) were simultaneously and slowly added to a solution of L-phenylalaninol (50 g, 66 mmol) in tetrahydrofuran (1.3 L) and water (630 mL) under ice-cold conditions. This solution was stirred at room temperature for 18 hours, and the organic solvent was distilled off in vacuo, after which ethyl acetate (1 L) was added thereto. This solution was washed with 1M hydrochloric acid, saturated aqueous sodium hydrogen carbonate solution, and saturated saline solution, dehydrated with anhydrous magnesium sulfate, and concentrated in vacuo. The obtained white solid was recrystallized from a liquid mixture of ethyl acetate/hexane (1:10), thereby yielding N-(tert-butoxycarbonyl)-L-phenylalaninol (70 g, 84%) as a colorless crystal.

(2) N-(tert-Butoxycarbonyl)-L-phenylalaninol (69 g, 0.28 mol) was dissolved in DMSO (280 mL) and dichloromethane (140 mL), and this solution was cooled in an ice bath. Then, N,N-diisopropylethylamine (110 g, 0.82 mol) and a suspension of purified sulfur trioxide pyridine complex (130 g, 0.82 mol) in DMSO (100 mL) were added thereto. This solution was stirred for 1 hour under ice-cold conditions. The reaction solution was diluted with ethyl acetate (1.5 L), washed with 1M hydrochloric acid, saturated aqueous sodium hydrogen carbonate solution, and saturated saline solution, dehydrated with anhydrous magnesium sulfate, and concentrated in vacuo. The residue was crystallized from a liquid mixture of ethyl acetate/hexane mixture, thereby yielding N-(tert-butoxycarbonyl)-L-phenylalaninal (53 g, 77%) as a colorless crystal.

(3) N-(tert-Butoxycarbonyl)-L-phenylalaninal (17 g, 67 mmol) was dissolved in methanol (100 mL), and the solution was cooled to 5° C. Sodium bisulfite (7.0 g, 67 mmol) was dissolved in water (150 mL) and cooled to 5° C. The solution was added to an aldehyde solution, and the mixture was stirred at 5° C. for 18 hours. Sodium cyanide (4.0 g, 81 mmol) was dissolved in water (100 mL), and added with ethyl acetate (300 mL) to the above reaction mixture. The reaction solution was stirred at room temperature for 5 hours. The organic layer was separated, dehydrated with anhydrous magnesium sulfate, and concentrated in vacuo to yield cyanohydrin as a colorless oil. The cyanohydrin was dissolved in dioxane (250 mL) and concentrated hydrochloric acid (250 mL), followed by the addition of anisole (10 mL). This solution was gently refluxed for 18 hours. The reaction solution was cooled to room temperature and then concentrated in vacuo to yield a brown semi-solid substance. The brown semi-solid substance was dissolved in water (100 mL) and washed with diethyl ether (3×50 mL). The aqueous layer was then applied to a column of Dowex 50×8 (100 to 200 mesh, H+ type; 25×1.8 cm), washed with water until the pH reached 5.5, and eluted with 2M ammonia water (about 1.5 L). The eluted ammonia water was concentrated in vacuo to yield (3S)-3-amino-2-hydroxy-4-phenylbutyric acid (12 g, 88%) as a white solid.

(4) (3S)-3-Amino-2-hydroxy-4-phenylbutyric acid (11 g, 56.34 mmol) was dissolved in a 1M aqueous sodium hydroxide solution (70 mL), and a solution of di-t-butyldicarbonate (12 g, 57 mmol) in dioxane (70 mL) was added thereto. The solution was stirred at room temperature for 18 hours while the pH was maintained between 10 and 11 by appropriately adding a 1M aqueous sodium hydroxide solution. The mixture was diluted with water (600 mL) and washed with diethyl ether (2×200 mL). While the aqueous layer was cooled in an ice bath, the pH was adjusted to 2 by the addition of 1M hydrochloric acid. Then, the mixture was extracted with diethyl ether (3×250 mL). The organic layer was dehydrated with anhydrous magnesium sulfate, followed by concentration to yield (3S)-3-(tert-butoxycarbonylamino)-2-hydroxy-4-phenylbutyric acid (12 g, 72%) as a colorless solid of a diastereomeric mixture.

(5) (3S)-3-(tert-butoxycarbonylamino)-2-hydroxy-4-phenylbutyric acid (6.3 g, 21 mmol) and 1-hydroxybenzotriazole (3.0 g, 22.4 mmol) were dissolved in DMF (45 mL), and cooled in an ice bath. Thereafter, 1-ethyl-3-(3-dimethylaminopropyl) carbodiimide hydrochloride (4.6 g, 24 mmol) was added thereto, and an aqueous ethylamine solution (3.0 mL) was further added thereto. The solution was stirred for 18 hours. The solution was then diluted with ethyl acetate (200 mL), washed with 1M hydrochloric acid, saturated aqueous sodium hydrogen carbonate solution, and saturated saline solution, dehydrated with anhydrous magnesium sulfate, and concentrated in vacuo, thereby yielding ((1S)-1-benzyl-3-ethylamino-2-hydroxy-3-oxopropyl) carbamic acid 1,1-dimethylethyl ester (5.8 g, 84%) as a white solid.

(6) ((1S)-1-benzyl-3-ethylamino-2-hydroxy-3-oxopropyl) carbamic acid 1,1-dimethylethyl ester (5.5 g, 17 mmol) was dissolved in 4N hydrochloric acid/dioxane solution (65 mL), and the solution was stirred at room temperature for 3 hours. This solution was concentrated in vacuo to quantitatively yield the title compound (4.4 g) as a white solid.

Melting point: 162.8-163.3° C. (Major), $^1$H-NMR (300 MHz, DMSO-$d_6$) δ1.02 (t, 3H, J=7.2), 2.93 (m, 2H), 3.05-3.20 (m, 2H), 3.60 (m, 1H), 3.88 (m, 1H), 6.75 (d, 1H, J=6.0), 7.19-7.37 (m, 5H), 8.08 (m, 1H), 8.17 (br s, 3H). (Minor), $^1$H-NMR (300 MHz, DMSO-$d_6$) δ0.97 (t, 3H, J=7.4), 2.80 (d, 2H, J=6.9), 3.00 (m, 2H), 3.69 (m, 1H), 4.26 (m, 1H), 6.53 (d, 1H, J=5.4), 7.19-7.37 (m, 5H), 8.03 (t, 1H, J=5.7), 8.17 (br s, 3H).

Reference Example 9

(3S)-3-Amino-N-cyclopropyl-2-hydroxy-4-phenylbutanamide hydrochloride

The reaction was performed as in Reference Example 8 (5) by using cyclopropylamine in place of an aqueous ethylamine solution, thereby yielding ((1S)-1-benzyl-3-cyclopropylamino-2-hydroxy)-3-oxopropyl)carbamic acid 1,1-dimethylethyl ester as a white solid. The reaction was performed as in Reference Example 8 (6) by using ((1S)-1-benzyl-3-cyclopropylamino-2-hydroxy-3-oxopropyl)carbamic acid 1,1-dimethylethyl ester in place of ((1S)-1-benzyl-3-ethylamino-2-hydroxy-3-oxopropyl) carbamic acid 1,1-dimethylethyl ester, thereby yielding the title compound as a white solid.

Melting point: 162.9-163.3° C. $^1$H-NMR (300 MHz, DMSO-$d_6$) δ0.44 (m, 2H), 0.57 (m, 2H), 2.50 (m, 0.5H), 2.65 (m, 0.5H), 2.82 (d, 1H, J=6.9), 2.94 (m, 1H), 3.60 (m, 0.5H), 3.70 (m, 0.5H), 3.87 (m, 0.5H), 4.26 (d, 0.5H, J=2.4), 6.45 (br s, 0.5H), 6.69 (br s, 0.5H), 7.23-7.35 (m, 5H), 7.99 (d, 0.5H, J=4.2), 8.08 (br s, 1.5H), 8.09 (d, 0.5H, J=4.5), 8.23 (br s, 1.5H).

Reference Example 10

(3S)-3-Amino-2-hydroxy-4-phenyl-N-propylbutanamide hydrochloride

The reaction was performed as in Reference Example 8 (5) by using propylamine in place of an aqueous ethylamine solution, thereby yielding ((1S)-1-benzyl-2-hydroxy-3-oxo-3-(propylamino)propyl)carbamic acid 1,1-dimethylethyl ester as a white solid. The reaction was performed as in Reference Example 8 (6) by using ((1S)-1-benzyl-2-hydroxy-3-oxo-3-(propylamino)propyl)carbamic acid 1,1-dimethylethyl ester in place of ((1S)-1-benzyl-3-ethylamino-2-hydroxy-3-oxopropyl)carbamic acid 1,1-dimethylethyl ester, thereby yielding the title compound as a white solid.

Melting point: 127.8-129.5° C. $^1$H-NMR (300 MHz, DMSO-$d_6$) δ0.82 (m, 3H), 1.35-1.47 (m, 2H), 2.82 (m, 0.5H), 2.95 (m, 3H), 3.09 (m, 0.5H), 3.58 (m, 0.5H), 3.70 (m, 0.5H), 3.92 (m, 0.5H), 4.31 (m, 0.5H), 6.55 (d, 0.5H, J=4.8), 6.77 (d, 0.5H, J=6.6), 7.21-7.36 (m, 5H), 7.98-8.15 (m, 2.5H), 8.24 (br s, 1.5H).

Reference Example 11

(3S)-3-Amino-N-cyclobutyl-2-hydroxy-4-phenylbutanamide hydrochloride

The reaction was performed as in Reference Example 8 (5) by using cyclobutylamine in place of an aqueous ethylamine solution, thereby yielding ((1S)-1-benzyl-3-cyclobutylamino-2-hydroxy-3-oxopropyl)carbamic acid 1,1-dimethylethyl ester as a white solid. The reaction was performed as in Reference Example 8 (6) by using ((1S)-1-benzyl-3-cyclobutylamino-2-hydroxy-3-oxopropyl)carbamic acid 1,1-dimethylethyl ester in place of ((1S)-1-benzyl-3-ethylamino-2-hydroxy-3-oxopropyl) carbamic acid 1,1-dimethylethyl ester, thereby yielding the title compound as a white solid.

Melting point: 162.5-163.7° C. $^1$H-NMR (300 MHz, DMSO-$d_6$) δ1.59 (m, 2H), 1.88-2.18 (m, 4H), 2.80 (d, 1H, J=6.6), 2.91 (m, 1H), 3.58 (m, 0.5H), 3.69 (m, 0.5H), 3.87 (m, 0.5H), 4.08 (m, 0.5H), 4.16-4.24 (m, 1H), 6.50 (d, 0.5H, J=5.4), 6.72 (d, 0.5H, J=6.0), 7.21-7.33 (m, 5H), 8.05 (br s, 1.5H), 8.19 (d, 0.5H, J=7.8), 8.20 (br s, 1.5H), 8.29 (d, 0.5H, J=8.1).

Reference Example 12

(3S)-3-Amino-N-butyl-2-hydroxy-4-phenylbutanamide hydrochloride

The reaction was performed as in Reference Example 8 (5) by using butylamine in place of an aqueous ethylamine solution, thereby yielding ((1S)-1-benzyl-3-butylamino-2-hydroxy-3-oxopropyl)carbamic acid 1,1-dimethylethyl ester as a white solid. The reaction was performed as in Reference Example 8 (6) by using ((1S)-1-benzyl-3-butylamino-2-hydroxy-3-oxopropyl)carbamic acid 1,1-dimethylethyl ester in place of ((S)-1-benzyl-3-ethylamino-2-hydroxy-3-oxopropyl) carbamic acid 1,1-dimethylethyl ester, thereby yielding the title compound as a white solid.

Melting point: 141.0-141.4° C. $^1$H-NMR (300 MHz, DMSO-$d_6$) δ0.86 (m, 3H), 1.16-1.47 (m, 4H), 2.80 (m, 0.5H), 2.99 (m, 3H), 3.13 (m, 0.5H), 3.57 (m, 0.5H), 3.70 (m, 0.5H), 3.92 (m, 0.5H), 4.30 (m, 0.5H), 6.53 (br s, 0.5H), 6.77 (d, 0.5H, J=6.6), 7.19-7.39 (m, 5H), 7.97-8.15 (m, 2.5H), 8.22 (s, 1.5H).

Reference Example 13

(3S)-3-Amino-2-hydroxy-4-phenyl-N-(2,2,2-trifluoroethyl) butanamide hydrochloride The reaction was performed as in Reference Example 8 (5) by using 2,2,2-trifluoroethylamine in place of an aqueous ethylamine solution, thereby yielding ((1S)-1-benzyl-2-hydroxy-3-oxo-3-(2,2,2-trifluoroethylamino)propyl) carbamic acid 1,1-dimethylethyl ester as a white solid. The reaction was performed as in Reference Example 8 (6) by using ((1S)-1-benzyl-2-hydroxy-3-oxo-3-(2,2,2-trifluoroethylamino)propyl)carbamic acid 1,1-dimethylethyl ester in place of ((1S)-1-benzyl-3-ethylamino-2-hydroxy-3-oxopropyl) carbamic acid 1,1-dimethylethyl ester, thereby yielding (3S)-β-amino-2-hydroxy-4-phenyl-N-(2,2,2-trifluoroethyl) butanamide hydrochloride as a white solid. Melting point: 103.0-108.5° C. $^1$H-NMR (300 MHz, DMSO-$d_6$) δ2.71-2.85 (m, 1H), 2.88-2.97 (m, 1H), 3.60-3.82 (m, 2.5H), 3.91-4.05 (m, 1H), 4.45 (m, 0.5H), 6.75 (d, 0.5H, J=5.7), 6.98 (d, 0.5H, J=6.3), 7.20-7.35 (m, 5H), 8.12 (br s, 1.5H), 8.25 (br s, 1.5H), 8.70 (m, 1H).

Reference Example 14

(3S)-3-Amino-2-hydroxy-N-(2-indanyl)-4-phenylbutanamide hydrochloride

The reaction was performed as in Reference Example 8 (5) by using 2-aminoindan in place of an aqueous ethylamine solution, thereby yielding ((1S)-1-benzyl-3-(2-indanylamino)-2-hydroxy-3-oxopropyl)carbamic acid 1,1-dimethylethyl ester as a white solid.

The reaction was performed as in Reference Example 8 (6) by using ((1S)-1-benzyl-3-(2-indanylamino)-2-hydroxy-3-oxopropyl)carbamic acid 1,1-dimethylethyl ester in place of ((1S)-1-benzyl-3-ethylamino-2-hydroxy-3-oxopropyl) carbamic acid 1,1-dimethylethyl ester, thereby yielding (3S)-β-amino-2-hydroxy-N-(2-indanyl)-4-phenylbutanamide hydrochloride as a white solid. Melting point: 183.0-184.8° C. $^1$H-NMR (300 MHz, DMSO-$d_6$) δ2.76-2.96 (m, 4H), 3.01-3.18 (m, 2H), 3.62 (m, 0.5H), 3.74 (m, 0.5H), 3.92 (m, 0.5H), 4.25-4.39 (m, 1H), 4.49 (m, 0.5H), 6.48 (d, 0.5H, J=5.7), 6.72 (d, 0.5H, J=5.7), 7.13-7.35 (m, 9H), 8.15 (m, 3.5H), 8.26 (d, 0.5H, J=7.2).

Reference Example 15

(3S)-3-Amino-2-hydroxy-N-(2-methoxyethyl)-4-phenylbutanamide hydrochloride

The reaction was performed as in Reference Example 8 (5) by using methoxyethylamine in place of an aqueous ethylamine solution, thereby obtaining ((1S)-1-benzyl-2-hydroxy-3-(2-methoxyethyl)-3-oxopropyl) carbamic acid 1,1-dimethylethyl ester as a white solid.

The reaction was performed as in Reference Example 8 (6) by using ((1S)-1-benzyl-2-hydroxy-3-(2-methoxyethyl)-3-oxopropyl)carbamic acid 1,1-dimethylethyl ester in place of ((1S)-1-benzyl-3-ethylamino-2-hydroxy-3-oxopropyl) carbamic acid 1,1-dimethylethyl ester, thereby obtaining (3S)-β-amino-2-hydroxy-N-(2-methoxyethyl)-4-phenylbutanamide hydrochloride as a white solid.

Melting point: 113.9-117.7° C. $^1$H-NMR (300 MHz, DMSO-$d_6$) δ2.82 (d, 1H, J=6.6), 2.95 (m, 1H), 3.10-3.19 (m, 2H), 3.22 (s, 1.5H), 3.23 (s, 1.5H), 3.28-3.34 (m, 2H), 3.57 (m, 0.5H), 3.70 (m, 0.5H), 3.92 (m, 0.5H), 4.32 (m, 0.5H), 6.59 (d, 0.5H, J=4.5), 6.87 (d, 0.5H, J=6.0), 7.22-7.36 (m, 5H), 7.92 (t, 0.5H, J=5.7), 7.98 (t, 0.5H, J=5.1), 8.09 (br s, 1.5H), 8.24 (br s, 1.5H).

Reference Example 16

(3S)-3-Amino-N-ethyl-2-hydroxy-5-phenylpentanamide hydrochloride (1) N-Methylmorpholine (7.2 g, 72 mmol) and isobutyl chlorocarbonate (9.8 g, 72 mmol) were added to a solution of Boc-L-homophenylalanine (20 g, 72 mmol) in dimethoxyethane (100 mL) under ice-cold conditions. After one hour stirring, the reaction solution was filtered, and the filtrate was cooled in an ice bath. Thereafter, an aqueous solution (10 mL) of sodium borohydride (4.1 g, 107 mmol) was added thereto, followed by further addition of water (300 mL). The resulting precipitate was collected by filtration and washed with water and methanol to yield N-(tert-butoxycarbonyl)-L-homophenylalaninol (15 g, 79%) as a colorless crystal.

(2) The reaction was performed as in Reference Example 8 (2) by using N-(tert-butoxycarbonyl)-L-homophenylalaninol in place of N-(tert-butoxycarbonyl)-L-phenylalaninol, thereby yielding N-(tert-butoxycarbonyl)-L-homophenylalaninal as a colorless oil.

(3) The reaction was performed as in Reference Example 8 (3) by using N-(tert-butoxycarbonyl)-L-homophenylalaninal in place of N-(tert-butoxycarbonyl)-L-phenylalaninal, thereby yielding (3S)-3-amino-2-hydroxy-5-phenylpentanoic acid as a white solid.

(4) The reaction was performed as in Reference Example 8 (4) by using (3S)-β-amino-2-hydroxy-5-phenylpentanoic acid in place of (3S)-β-amino-2-hydroxy-4-phenylbutyric acid, thereby yielding (3S)-3-(tert-butoxycarbonylamino)-2-hydroxy-5-phenylpentanoic acid as a colorless oil.

(5) The reaction was performed as in Reference Example 8 (5) by using (3S)-3-(tert-butoxycarbonylamino)-2-hydroxy-5-phenylpentanoic acid in place of (3S)-3-(tert-butoxycarbonylamino)-2-hydroxy-4-phenylbutyric acid, thereby yielding ((1S)-3-ethylamino-2-hydroxy-3-oxo-1-(phenylethyl)propyl)carbamic acid 1,1-dimethylethyl ester as a white solid.

(6) The reaction was performed as in Reference Example 8 (6) by using ((1S)-3-ethylamino-2-hydroxy-3-oxo-1-(phenylethyl)propyl)carbamic acid 1,1-dimethylethyl ester in place of ((1S)-1-benzyl-3-ethylamino-2-hydroxy-3-oxopropyl)carbamic acid 1,1-dimethylethyl ester, thereby yielding (3S)-β-amino-N-ethyl-2-hydroxy-5-phenylpentanamide hydrochloride as a white solid.

Melting point: 134.4-134.9° C. $^1$H-NMR (300 MHz, DMSO-$d_6$) δ0.99-1.06 (m, 3H), 1.65-1.96 (m, 2H), 2.54-2.76 (m, 2H), 3.07-3.23 (m, 2H), 4.15 (br s, 0.5H), 4.25 (br s, 0.5H), 6.44 (br s, 0.5H), 6.55 (br s, 0.5H), 7.17-7.33 (m, 5H), 7.99 (br s, 1.5H), 8.15 (t, 1H, J=6.2), 8.23 (br s, 1.5H).

Reference Example 17

(3S)-3-Amino-N-cyclopropyl-2-hydroxy-5-phenylpentanamide hydrochloride

The reaction was performed as in Reference Example 16 (5) by using cyclopropylamine in place of an aqueous ethylamine solution, thereby yielding ((1S)-3-cyclopropylamino-2-hydroxy-3-oxo-1-(phenylethyl)propyl)carbamic acid 1,1-dimethylethyl ester as a white solid.

The reaction was performed as in Reference Example 16 (6) by using ((1S)-3-cyclopropylamino-2-hydroxy-3-oxo-1-(phenylethyl)propyl)carbamic acid 1,1-dimethylethyl ester in place of ((1S)-1-benzyl-3-ethylamino-2-hydroxy-3-oxopropyl)carbamic acid 1,1-dimethylethyl ester, thereby yielding (3S)-β-amino-N-cyclopropyl-2-hydroxy-5-phenylpentanamide hydrochloride as a white solid.

Melting point: 140.2-141.3° C. $^1$H-NMR (300 MHz, DMSO-$d_6$) δ0.46-0.64 (m, 4H), 1.64-1.99 (m, 2H), 2.54-2.78 (m, 3H), 3.35 (m, 1H), 4.13 (br s, 0.5H), 4.26 (br s, 0.5H), 6.37 (br s, 0.5H), 6.51 (br s, 0.5H), 7.17-7.33 (m, 5H), 8.05 (br s, 1.5H), 8.15 (d, 0.5H, J=4.5), 8.20 (d, 0.5H, J=4.8), 8.27 (br s, 1.5H).

Reference Example 18

(3S)-3-Amino-2-hydroxy-5-methyl-N-(2-phenoxyethyl)hexanamide hydrochloride (1) The reaction was performed as in Reference Example 8 (1) by using L-leucinol in place of L-phenylalaninol, thereby yielding N-(tert-butoxycarbonyl)-L-leucinol (70 g, 84%) as a colorless oil.

(2) The reaction was performed as in Reference Example 8 (2) by using N-(tert-butoxycarbonyl)-L-leucinol in place of N-(tert-butoxycarbonyl)-L-phenylalaninol, thereby yielding N-(tert-butoxycarbonyl)-L-leucinal as a colorless oil.

(3) The reactions were performed as in Reference Examples 8 (3) and 8 (4), by using N-(tert-butoxycarbonyl)-L-leucinal in place of N-(tert-butoxycarbonyl)-L-phenylalaninal, thereby yielding (3S)-3-(tert-butoxycarbonylamino)-2-hydroxy-5-methyl hexanoic acid as a colorless oil.

(4) The reaction was performed as in Reference Example 8 (5) by using (3S)-3-(tert-butoxycarbonylamino)-2-hydroxy-5-methyl hexanoic acid in place of (3S)-3-(tert-butoxycarbonylamino)-2-hydroxy-4-phenylbutyric acid, and by using 2-phenoxyethylamine in place of an aqueous ethylamine solution, thereby yielding ((1S)-2-hydroxy-1-(2-methylpropyl)-3-oxo-3-(2-phenoxyethyl)aminopropyl carbamic acid 1,1-dimethylethyl ester as a colorless oil.

(5) The reaction was performed as in Reference Example 8 (6) by using ((1S)-2-hydroxy-1-(2-methylpropyl)-3-oxo-3-(2-phenoxyethyl)aminopropyl)carbamic acid 1,1-dimethylethyl ester in place of ((1S)-1-benzyl-3-ethylamino-2-hydroxy-3-oxopropyl)carbamic acid 1,1-dimethylethyl ester, thereby yielding the title compound as a white solid.

Melting point: 93.6-96.2° C. $^1$H-NMR (300 MHz, DMSO-d$_6$) δ0.71-0.89 (m, 6H), 1.35-1.47 (m, 2H), 1.72 (m, 1H), 3.48-3.54 (m, 4H), 4.00-4.07 (m, 2H), 4.12 (d, 0.5H, J=3.6), 4.33 (d, 0.5H, J=1.8), 6.91-6.96 (m, 3H), 7.27-7.32 (m, 2H), 7.95 (br s, 1.5H), 8.19-8.29 (m, 2.5H).

Reference Example 19

3-Amino-2-hydroxy-5-phenylpentanamide hydrochloride

The reaction was performed as in Reference Example 8 (5) by using ammonia gas in place of an aqueous ethylamine solution, thereby yielding (1-benzyl-β-amino-2-hydroxy-3-oxopropyl)carbamic acid 1,1-dimethylethyl ester as a white solid.

The reaction was performed as in Reference Example 8 (6) by using (1-benzyl-β-amino-2-hydroxy-3-oxopropyl)carbamic acid 1,1-dimethylethyl ester in place of ((1S)-1-benzyl-3-ethylamino-2-hydroxy-3-oxopropyl)carbamic acid 1,1-dimethylethyl ester, thereby yielding the title compound as a white solid.

$^1$H-NMR (300 MHz, DMSO-d$_6$) δ2.82 (m, 1H), 2.93 (m, 1H), 3.61 (m, 1H), 3.85 (m, 0.5H), 4.26 (m, 0.5H), 6.48 (d, 0.5H, J=4.8), 6.75 (d, 0.5H, J=5.7), 7.24-7.35 (m, 5H), 7.52 (m, 2H), 8.04 (brs, 1.5H), 8.17 (brs, 1.5H).

Reference Example 20

N-((2-(Pyridin-2-yl)ethyl)carbonyl)-L-leucine N-hydroxysuccinimide ester (1) The reaction was performed as in Reference Example 2 (1) by using (2-pyridyl)ethanol in place of (S)-3-hydroxytetrahydrofuran, thereby yielding N-succinimidyl 2-(pyridin-2-yl)ethyl carbonate as a brown oil.
(2) The reaction was performed as in Reference Example 2 (2) by using N-succinimidyl 2-(pyridin-2-yl)ethyl carbonate in place of N-succinimidyl(3S)-3-tetrahydrofuranyl carbonate, thereby yielding N-((2-(pyridin-2-yl)ethyloxy)carbonyl)-L-leucine ethyl ester as a colorless oil.
(3) The reaction was performed as in Reference Example 2 (3) by using N-((2-(pyridin-2-yl)ethyloxy)carbonyl)-L-leucine ethyl ester in place of N-(((3S)-tetrahydrofuran-3-yloxy) carbonyl)-L-leucine ethyl ester, thereby yielding N-((2-(pyridin-2-yl)ethyloxy)carbonyl)-L-leucine as a white solid.
(4) The reaction was performed as in Reference Example 1 (2) by using N-((2-(pyridin-2-yl)ethyloxy) carbonyl)-L-leucine) in place of N-((2-methoxyethoxy)carbonyl)-L-leucine, thereby yielding the title compound as a colorless oil.

$^1$H-NMR (300 MHz, DMSO-d$_6$) δ0.82-0.91 (m, 6H), 1.42-1.76 (m, 3H), 2.76-2.81 (m, 4H), 3.00-3.06 (m, 2H), 4.30-4.40 (m, 3H), 7.23 (dd, 1H, J=7.1, 5.3), 7.30 (d, 1H, J=7.8), 7.71 (m, 1H), 7.90 (d, 1H, J=8.1), 8.50 (d, 1H, J=4.5).

Reference Example 21

N-((2-(6-Methylpyridin-2-yl)ethyloxy)carbonyl)-L-leucine N-hydroxysuccinimide ester (1) The reaction was performed as in Reference Example 2 (1) by using 2-(6-methyl-2-pyridyl)ethanol in place of (S)-3-hydroxytetrahydrofuran, thereby yielding N-succinimidyl 2-(6-methylpyridin-2-yl)ethyl carbonate as a brown oil.
(2) The reaction was performed as in Reference Example 2 (2) by using N-succinimidyl 2-(6-methylpyridin-2-yl)ethyl carbonate in place of N-succinimidyl (3S)-3-tetrahydrofuranyl carbonate, thereby yielding N-((2-(6-methylpyridin-2-yl)ethyloxy)carbonyl)-L-leucine ethyl ester as a colorless oil.
(3) The reaction was performed as in Reference Example 2 (3) by using N-((2-(6-methylpyridin-2-yl)ethyloxy)carbonyl)-L-leucine ethyl ester in place of N-(((3S)-tetrahydrofuran-3-yloxy)carbonyl)-L-leucine ethyl ester, thereby yielding N-((2-(6-methylpyridin-2-yl)ethyloxy)carbonyl)-L-leucine as a colorless oil.
(4) The reaction was performed as in Reference Example 1 (2) by using N-((2-(6-methylpyridin-2-yl)ethyloxy)carbonyl)-L-leucine in place of N-((2-methoxyethyloxy)carbonyl)-L-leucine, thereby yielding the title compound as a colorless oil.

$^1$H-NMR (300 MHz, DMSO-d$_6$) δ0.83-0.92 (m, 6H), 1.49-1.77 (m, 3H), 2.43 (s, 3H), 2.81 (s, 4H), 2.99 (t, 2H, J=6.5), 4.29-4.42 (m, 3H), 7.07-7.09 (m, 2H), 7.58 (t, 1H, J=7.7), 7.91 (d, 1H, J=8.4).

Reference Example 22

N-((2-(5-Ethylpyridin-2-yl)ethyloxy)carbonyl)-L-leucine N-hydroxysuccinimide ester (1) The reaction was performed as in Reference Example 2 (1) by using (5-ethylpyridin-2-yl)ethanol in place of (S)-3-hydroxytetrahydrofuran, thereby yielding N-succinimidyl 2-(5-ethylpyridin-2-yl)ethyl carbonate as a brown oil.
(2) The reaction was performed as in Reference Example 2 (2) by using N-succinimidyl 2-(5-ethylpyridin-2-yl)ethyl carbonate in place of N-succinimidyl(3S)-3-tetrahydrofuranyl carbonate, thereby yielding N-((2-(5-ethylpyridin-2-yl)ethyloxy)carbonyl)-L-leucine ethyl ester as a colorless oil.
(3) The reaction was performed as in Reference Example 2 (3) by using N-((2-(5-ethylpyridin-2-yl)ethyloxy)carbonyl)-L-leucine ethyl ester in place of N-(((3S)-tetrahydrofuran-3-yloxy)carbonyl)-L-leucine ethyl ester, thereby yielding N-((2-(5-ethylpyridin-2-yl)ethyloxy)carbonyl)-L-leucine as a colorless oil.
(4) The reaction was performed as in Reference Example 1 (2) by using N-((2-(5-ethylpyridin-2-yl)ethyloxy)carbonyl)-L-leucine in place of N-((2-methoxyethoxy)carbonyl)-L-leucine, thereby yielding the title compound as a colorless oil.

$^1$H-NMR (300 MHz, DMSO-d$_6$) δ0.75-0.92 (m, 6H), 1.12-1.25 (m, 3H), 1.36-1.72 (m, 3H), 2.54-2.63 (m, 2H), 2.81-2.83 (m, 4H), 2.96-3.02 (m, 2H), 4.04 (m, 1H), 4.29-4.37 (m, 2H), 7.21 (d, 1H, J=7.8), 7.53 (m, 1H), 7.90 (d, 1H, J=7.8), 8.34 (m, 1H).

Reference Example 23

N-((2-tert-Butoxyethyloxy)carbonyl)-L-leucine N-hydroxysuccinimide ester (1) The reaction was performed as in Reference Example 2 (1) by using ethylene glycol tert-butyl ether in place of (S)-3-hydroxytetrahydrofuran, thereby yielding N-succinimidyl 2-tert-butoxyethyl carbonate as a colorless oil.

(2) The reaction was performed as in Reference Example 2 (2) by using N-succinimidyl 2-tert-butoxyethyl carbonate in place of N-succinimidyl (3S)-3-tetrahydrofuranyl carbonate, thereby yielding N-((2-tert-butoxyethyloxy)carbonyl)-L-leucine ethyl ester as a colorless oil.

(3) The reaction was performed as in Reference Example 2 (3) by using N-((2-tert-butoxyethyloxy) carbonyl)-L-leucine ethyl ester in place of N-(((3S)-tetrahydrofuran-3-yloxy)carbonyl)-L-leucine ethyl ester, thereby yielding N-((2-tert-butoxyethyloxy)carbonyl)-L-leucine as a colorless oil.

(4) The reaction was performed as in Reference Example 1 (2) by using N-((2-tert-butoxyethyloxy)carbonyl)-L-leucine in place of N-((2-methoxyethyloxy) carbonyl)-L-leucine, thereby yielding the title compound as a colorless oil.

$^1$H-NMR (300 MHz, DMSO-$d_6$) δ0.89 (d, 3H, J=6.3), 0.92 (d, 3H, J=6.3), 1.13 (s, 9H), 1.61 (m, 1H), 1.74 (m, 2H), 2.81 (s, 4H), 3.48 (t, 2H, J=4.7), 4.04 (m, 2H), 4.40 (m, 1H), 8.00 (d, 1H, J=7.8).

Reference Example 24

N-((2-Isopropoxyethyloxy)carbonyl)-L-leucine N-hydroxysuccinimide ester (1) The reaction was performed as in Reference Example 2 (1) by using ethylene glycol isopropyl ether in place of (S)-3-hydroxytetrahydrofuran, thereby yielding N-succinimidyl 2-isopropoxyethyl carbonate as a colorless oil.

(2) The reaction was performed as in Reference Example 2 (2) by using N-succinimidyl 2-isopropoxyethyl carbonate in place of N-succinimidyl (3S)-3-tetrahydrofuranyl carbonate, thereby yielding N-((2-isopropoxyethyloxy)carbonyl)-L-leucine ethyl ester as a colorless oil.

(3) The reaction was performed as in Reference Example 2 (3) by using N-((2-isopropoxyethyloxy)carbonyl)-L-leucine ethyl ester in place of N-(((3S)-tetrahydrofuran-3-yloxy)carbonyl)-L-leucine ethyl ester, thereby yielding N-((2-isopropoxyethyloxy)carbonyl)-L-leucine as a colorless oil.

(4) The reaction was performed as in Reference Example 1 (2) by using N-((2-isopropoxyethyloxy)carbonyl)-L-leucine in place of N-((2-methoxyethyloxy) carbonyl)-L-leucine, thereby yielding the title compound as a colorless oil.

$^1$H-NMR (300 MHz, DMSO-$d_6$) δ0.89 (d, 3H, J=6.6), 0.92 (d, 3H, J=6.3), 1.08 (d, 6H, J=6.3), 1.61 (m, 1H), 1.74 (m, 2H), 2.81 (s, 4H), 3.53 (m, 2H), 3.57 (m, 1H), 4.07 (m, 2H), 4.40 (m, 1H), 8.02 (d, 1H, J=7.8).

Production Example 1

((1S)-1-((((1S)-1-Benzyl-2,3-dioxo-3-(ethylamino) propyl)amino)carbonyl)-3-methylbutyl) carbamic acid 2-methoxyethyl ester (Compound 1)

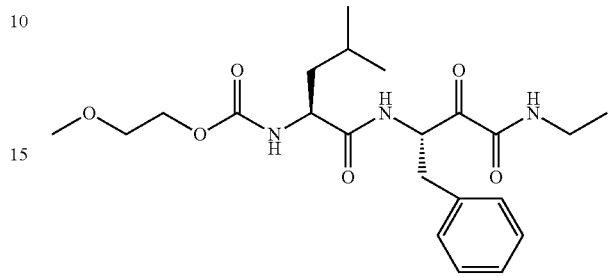

Triethylamine (1.1 g, 11 mmol) was added to a solution of the compound of Reference Example 1 (1.2 g, 3.6 mmol) and the compound of Reference Example 8 (1.0 g, 4.0 mmol) in DMF. This solution was stirred at room temperature for 18 hours and concentrated in vacuo. The residue was dissolved in ethyl acetate, and the solution was washed with 1M hydrochloric acid, saturated aqueous sodium hydrogen carbonate solution, and saturated saline solution, dehydrated with anhydrous magnesium sulfate, and concentrated in vacuo. The resulting solid was washed with a liquid mixture of ethyl acetate/hexane (1:9) to yield ((1S)-1-((((1S)-1-benzyl-3-ethylamino-2-hydroxy-3-oxopropyl)amino) carbonyl)-3-methylbutyl) carbamic acid 2-methoxyethyl ester (0.75 g, 47%) as a white solid. A Dess-Martin reagent (1.0 g, 2.4 mmol) was added to a solution of ((1S)-1-((((1S)-1-benzyl-3-ethylamino-2-hydroxy-3-oxopropyl)amino) carbonyl)-3-methylbutyl) carbamic acid 2-methoxyethyl ester (0.7 g, 1.6 mmol) in dichloromethane (70 mL), and the resulting solution was stirred at room temperature for 18 hours. Thereafter, a 10% aqueous sodium thiosulfate solution (35 mL) and a saturated aqueous sodium hydrogen carbonate solution (35 mL) were added thereto, and the mixture was stirred at room temperature for 30 minutes. The organic layer was separated, washed with 1M hydrochloric acid, saturated aqueous sodium hydrogen carbonate solution, and saturated saline solution, dehydrated with anhydrous magnesium sulfate, and concentrated in vacuo. The residue was crystallized from a liquid mixture of ethyl acetate/hexane to yield the title compound (0.62 g, 88%) as a colorless crystal.

Melting point: 138.0-138.3° C. $^1$H-NMR (300 MHz, DMSO-$d_6$) δ0.83 (d, 3H, J=7.5), 0.85 (d, 3H, J=7.2), 1.04 (t, 3H, J=7.1), 1.35 (m, 2H), 1.56 (m, 1H), 2.82 (m, 1H), 3.14 (m, 3H), 3.25 (s, 3H), 3.47 (t, 2H, J=4.5), 4.04 (m, 3H), 5.19 (m, 1H), 7.16-7.33 (m, 6H), 8.24 (d, 1H, J=7.2), 8.70 (m, 1H). MALDI-TOF-MS: $C_{22}H_{33}N_3O_6$ (M+Na)$^+$, 458.2267, Actual measurement value, 458.2361

Production Example 2

((1S)-1-((((1S)-1-Benzyl-2,3-dioxo-3-(ethylamino) propyl)amino)carbonyl)-3-methylbutyl)carbamic acid (3S)-tetrahydrofuran-3-yl ester (Compound 2)

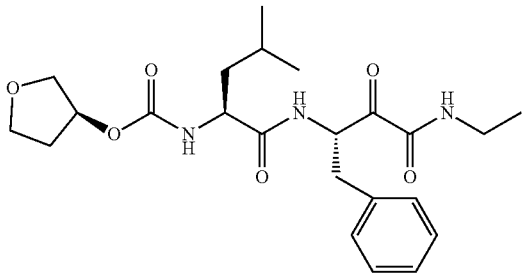 [SMILES: CCNC(=O)C(=O)[C@H](Cc1ccccc1)NC(=O)[C@H](CC(C)C)NC(=O)O[C@H]1CCOC1]

The reaction was performed as in Production Example 1 by using the compound of Reference Example 2 in place of the compound of Reference Example 1, thereby obtaining the title compound as a colorless crystal, via ((1S)-1-((((1S)-1-benzyl-3-ethylamino-2-hydroxy-3-oxopropyl)amino)carbonyl)-3-methylbutyl)carbamic acid (3S)-tetrahydrofuran-3-yl ester. Melting point: 158.9-160.7° C. $^1$H-NMR (300 MHz, DMSO-$d_6$) δ0.83 (d, 3H, J=6.6), 0.85 (d, 3H, J=6.9), 1.04 (t, 3H, J=7.1), 1.35 (m, 2H), 1.55 (m, 1H), 1.83 (m, 1H), 2.08 (m, 1H), 2.82 (m, 1H), 3.14 (m, 3H), 3.61-3.78 (m, 4H), 4.01 (m, 1H), 5.07 (m, 1H), 5.19 (m, 1H), 7.17-7.33 (m, 6H), 8.22 (d, 1H, J=7.2), 8.69 (t, 1H, J=5.7). MALDI-TOF-MS: $C_{23}H_{33}N_3O_6$ (M+H)$^+$, 448.2447, Actual measurement value, 448.2509.

Production Example 3

((1S)-1-((((1S)-1-Benzyl-2,3-dioxo-3-(ethylamino) propyl)amino)carbonyl)-3-methylbutyl)carbamic acid tetrahydro-4H-pyran-4-yl ester (Compound 3)

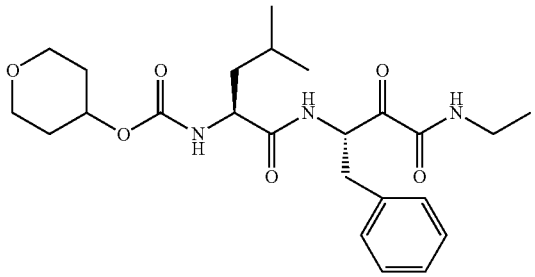 [SMILES: CCNC(=O)C(=O)[C@H](Cc1ccccc1)NC(=O)[C@H](CC(C)C)NC(=O)OC1CCOCC1]

The reaction was performed as in Production Example 1 by using the compound of Reference Example 3 in place of the compound of Reference Example 1, thereby obtaining the title compound as a colorless crystal, via ((1S)-1-((((1S)-1-benzyl-3-ethylamino-2-hydroxy-3-oxopropyl)amino)carbonyl)-3-methylbutyl)carbamic acid tetrahydro-4H-pyran-4-yl ester. Melting point: 140.0-141.8° C. $^1$H-NMR (300 MHz, DMSO-$d_6$) δ0.84 (m, 6H), 1.04 (t, 3H, J=7.2), 1.35 (m, 2H), 1.49 (m, 3H), 1.79 (m, 2H), 2.82 (m, 1H), 3.14 (m, 3H), 3.41 (m, 2H), 3.78 (m, 2H), 4.02 (m, 1H), 4.66 (m, 1H), 5.19 (m, 1H), 7.15-7.33 (m, 6H), 8.22 (d, 1H, J=7.2), 8.69 (t, 1H, J=5.7). MALDI-TOF-MS: $C_{24}H_{35}N_3O_6$ (M+Na)$^+$, 484.2424, Actual measurement value, 484.2486.

Production Example 4

((1S)-1-((((1S)-1-Benzyl-2,3-dioxo-3-(cyclopropylamino)propyl)amino)carbonyl)-3-methylbutyl)carbamic acid 2-methoxyethyl ester (compound 4)

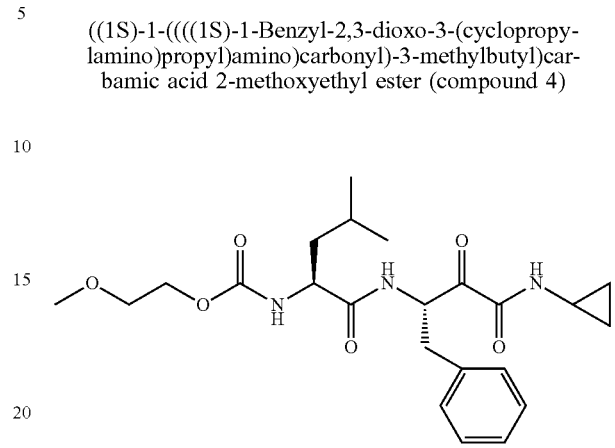

The reaction was performed as in Production Example 1 by using the compound of Reference Example 9 in place of the compound of Reference Example 8, thereby obtaining the title compound as a colorless crystal, via ((1S)-1-((((1S)-1-benzyl-3-cyclopropylamino-2-hydroxy-3-oxopropyl) amino) carbonyl)-3-methylbutyl)carbamic acid 2-methoxyethyl ester.

Melting point: 112.4-113.5° C. $^1$H-NMR (300 MHz, DMSO-$d_6$) δ0.58 (m, 2H), 0.65 (m, 2H), 0.83 (d, 3H, J=6.6), 0.85 (d, 3H, J=6.6), 1.35 (m, 2H), 1.56 (m, 1H), 2.68-2.88 (m, 2H), 3.11 (m, 1H), 3.25 (s, 3H), 3.47 (t, 2H, J=4.5), 4.04 (m, 3H), 5.17 (m, 1H), 7.17-7.34 (m, 6H), 8.25 (d, 1H, J=7.2), 8.73 (d, 1H, J=4.8). MALDI-TOF-MS: $C_{23}H_{33}N_3O_6$ (M+Na)$^+$, 470.2267, Actual measurement value, 470.2441. $[\alpha]_D^{25}$+6.3° (c0.20, DMSO)

Production Example 5

((1S)-1-((((1S)-1-Benzyl-3-(cyclopropylamino)-2,3-dioxopropyl)amino)carbonyl)-3-methylbutyl)carbamic acid (3S)-tetrahydrofuran-3-yl ester (Compound 5)

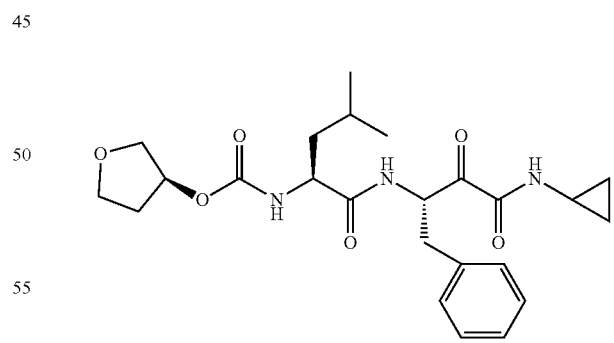

The reaction was performed as in Production Example 1 by using the compound of Reference Example 2 in place of the compound of Reference Example 1, and by using the compound of Reference Example 9 in place of the compound of Reference Example 8, thereby yielding the title compound as a colorless crystal, via ((1S)-1-((((1S)-1-benzyl-3-cyclopropylamino-2-hydroxy-3-oxopropyl)amino) carbonyl)-3-methylbutyl) carbamic acid (3S)-tetrahydrofuran-3-yl ester.

Melting point: 169.2-170.5° C. $^1$H-NMR (300 MHz, DMSO-$d_6$) δ0.58 (m, 2H), 0.65 (m, 2H), 0.83 (d, 3H, J=8.1), 0.85 (d, 3H, J=6.9), 1.34 (m, 2H), 1.55 (m, 1H), 1.83 (m, 1H), 2.08 (m, 1H), 2.79 (m, 2H), 3.12 (m, 1H), 3.61-3.80 (m, 4H), 4.02 (m, 1H), 5.08 (m, 1H), 5.17 (m, 1H), 7.22-7.35 (m, 6H), 8.24 (d, 1H, J=6.6), 8.74 (d, 1H, J=5.1). MALDI-TOF-MS: $C_{24}H_{33}N_3O_6$ (M+Na)$^+$, 482.2267, Actual measurement value, 482.2586.

Production Example 6

((1S)-1-((((1S)-1-Benzyl-3-cyclopropylamino-2,3-dioxopropyl)amino)carbonyl)-3-methylbutyl)carbamic acid tetrahydro-4H-pyran-4-yl ester (Compound 6)

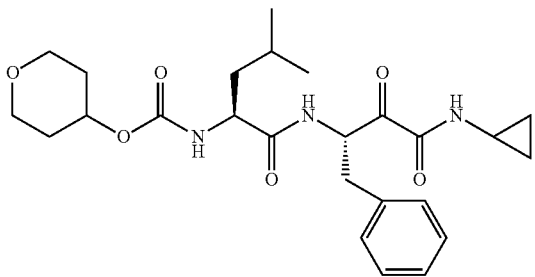 [SMILES: CC(C)C[C@H](NC(=O)OC1CCOCC1)C(=O)N[C@@H](Cc1ccccc1)C(=O)C(=O)NC1CC1]

The reaction was performed as in Production Example 1 by using the compound of Reference Example 3 in place of the compound of Reference Example 1, and by using the compound of Reference Example 9 in place of the compound of Reference Example 8, thereby yielding the title compound as a colorless crystal, via ((1S)-1-((((1S)-1-benzyl-3-cyclopropylamino-2-hydroxy-3-oxopropyl)amino) carbonyl)-3-methylbutyl) carbamic acid tetrahydro-4H-pyran-4-yl ester.

Melting point: 137.0-138.2° C. 1H-NMR (300 MHz, DMSO-$d_6$) δ0.58 (m, 2H), 0.65 (m, 2H), 0.84 (m, 6H), 1.35 (m, 2H), 1.48 (m, 3H), 1.80 (m, 2H), 2.79 (m, 2H), 3.11 (m, 1H), 3.41 (m, 2H), 3.79 (m, 2H), 4.03 (m, 1H), 4.65 (m, 1H), 5.18 (m, 1H), 7.15-7.30 (m, 6H), 8.23 (d, 1H, J=6.9), 8.73 (d, 1H, J=5.4). MALDI-TOF-MS: $C_{25}H_{35}N_3O_6$ (M+H)$^+$, 474.2604, Actual measurement value, 474.2643.

Production Example 7

((1S)-1-((((1S)-1-Benzyl-2,3-dioxo-3-(propylamino) propyl)amino) carbonyl)-3-methylbutyl) carbamic acid 2-methoxyethyl ester (Compound 7)

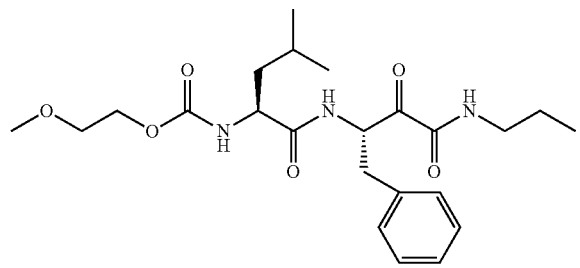 [SMILES: CCCNC(=O)C(=O)[C@H](Cc1ccccc1)NC(=O)[C@H](CC(C)C)NC(=O)OCCOC]

The reaction was performed as in Production Example 1 by using the compound of Reference Example 10 in place of the compound of Reference Example 8, thereby yielding the title compound as a colorless crystal, via ((1S)-1-((((1S)-1-benzyl-2-hydroxy-3-oxo-3-(propylamino) propyl)amino) carbonyl)-3-methylbutyl)carbamic acid 2-methoxyethyl ester.

Melting point: 108.8-109.9° C. $^1$H-NMR (300 MHz, DMSO-$d_6$) δ0.83 (m, 9H), 1.35 (m, 2H), 1.46 (m, 2H), 1.55 (m, 1H), 2.83 (dd, 1H, J=14.0, 9.2), 3.08 (m, 3H), 3.25 (s, 3H), 3.48 (t, 2H, J=4.4), 4.04 (m, 3H), 5.19 (m, 1H), 7.22-7.28 (m, 6H), 8.24 (d, 1H, J=6.9), 8.68 (t, 1H, J=5.6). MALDI-TOF-MS: $C_{23}H_{35}N_3O_6$ (M+H)$^+$, 450.2604, Actual measurement value, 450.2832.

Production Example 8

((1S)-1-((((1S)-1-Benzyl-2,3-dioxo-3-(cyclobutylamino)propyl)amino)carbonyl)-3-methylbutyl) carbamic acid 2-methoxyethyl ester (Compound 8)

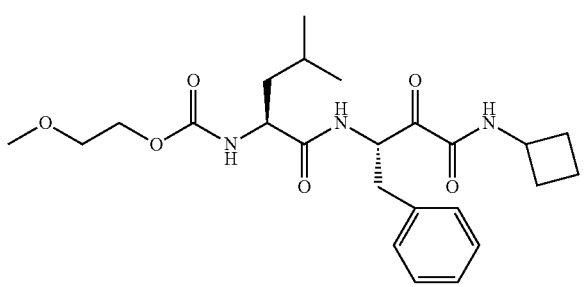 [SMILES: COCCOC(=O)N[C@@H](CC(C)C)C(=O)N[C@@H](Cc1ccccc1)C(=O)C(=O)NC1CCC1]

The reaction was performed as in Production Example 1 by using the compound of Reference Example 11 in place of the compound of Reference Example 8, thereby yielding the title compound as a colorless crystal, via ((1S)-1-((((1S)-1-benzyl-3-cyclobutylamino-2-hydroxy-3-oxopropyl)amino) carbonyl)-3-methylbutyl)carbamic acid 2-methoxyethyl ester.

Melting point: 114.2-115.3° C. 1H-NMR (300 MHz, DMSO-$d_6$) δ0.84 (m, 6H), 1.34 (m, 2H), 1.49-1.72 (m, 3H), 2.10 (m, 4H), 2.81 (dd, 1H, J=13.8, 9.3), 3.10 (m, 1H), 3.25 (s, 3H), 3.47 (m, 2H), 4.03 (m, 3H), 4.22 (m, 1H), 5.15 (m, 1H), 7.24 (m, 6H), 8.24 (d, 1H, J=7.2), 8.91 (d, 1H, J=7.8). MALDI-TOF-MS: $C_{24}H_{35}N_3O_6$ (M+Na)$^+$, 484.2424, Actual measurement value, 484.2400.

Production Example 9

((1S)-1-((((1S)-1-Benzyl-3-butylamino-2,3-dioxopropyl)amino) carbonyl)-3-methylbutyl) carbamic acid 2-methoxyethyl ester (Compound 9)

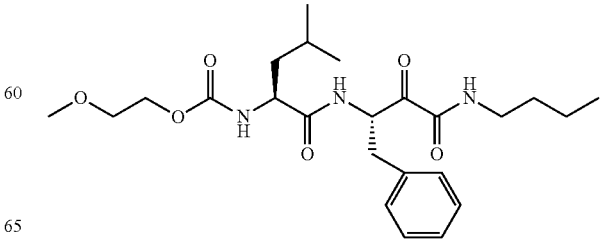

The reaction was performed as in Production Example 1 by using the compound of Reference Example 12 in place of the compound of Reference Example 8, thereby yielding the title compound as a colorless crystal, via ((1S)-1-((((1S)-1-benzyl-3-butylamino-2-hydroxy-3-oxopropyl)amino) carbonyl)-3-methylbutyl)carbamic acid 2-methoxyethyl ester.

Melting point: 94.0-95.2° C. $^1$H-NMR (300 MHz, DMSO-$d_6$) δ0.85 (m, 9H), 1.25 (m, 2H), 1.35 (m, 2H), 1.42 (m, 2H), 1.56 (m, 1H), 2.83 (dd, 1H, J=13.8, 9.0), 3.10 (m, 3H), 3.25 (s, 3H), 3.47 (t, 2H, J=4.5), 4.04 (m, 3H), 5.18 (m, 1H), 7.21-7.29 (m, 6H), 8.23 (d, 1H, J=6.6), 8.67 (t, 1H, J=6.0). MALDI-TOF-MS: $C_{24}H_{37}N_3O_6$ (M+H)+, 464.2760, Actual measurement value, 464.2870.

Production Example 10

((1S)-1-((((1S)-1-Benzyl-2,3-dioxo-3-(2,2,2-trifluoroethylamino) propyl)amino) carbonyl)-3-methylbutyl) carbamic acid 2-methoxyethyl ester (Compound 10)

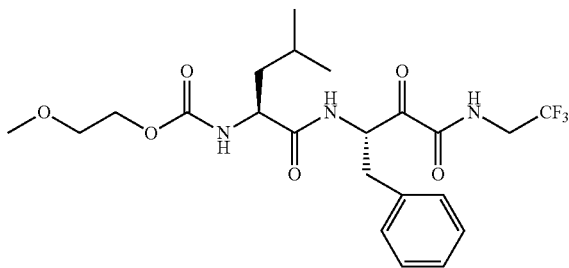 [SMILES: COCCOC(=O)N[C@@H](CC(C)C)C(=O)N[C@@H](Cc1ccccc1)C(=O)C(=O)NCC(F)(F)F]

The reaction was performed as in Production Example 1 by using the compound of Reference Example 13 in place of the compound of Reference Example 8, thereby yielding the title compound as a colorless crystal, via ((1S)-1-((((1S)-1-benzyl-2-hydroxy-3-oxo-3-(2,2,2-trifluoroethylamino)propyl)amino)carbonyl)-3-methylbutyl)carbamic acid 2-methoxyethyl ester.

Melting point: 152.5-153.9° C. $^1$H-NMR (300 MHz, DMSO-$d_6$) δ0.84 (m, 6H), 1.34 (m, 2H), 1.55 (m, 1H), 2.86 (dd, 1H, J=14.0, 8.6), 3.10 (dd, 1H, J=14.1, 4.8), 3.25 (s, 3H), 3.48 (t, 2H, J=4.7), 3.90 (m, 2H), 4.04 (m, 3H), 5.14 (m, 1H), 7.21-7.31 (m, 6H), 8.34 (d, 1H, J=6.9), 9.29 (m, 1H). MALDI-TOF-MS: $C_{22}H_{30}F_3N_3O_6$ (M+H)$^+$, 490.2165, Actual measurement value, 490.2434.

Production Example 11

((1S)-1-((((1S)-1-Benzyl-2,3-dioxo-3-(2-indanylamino)propyl)amino)carbonyl)-3-methylbutyl) carbamic acid 2-methoxyethyl ester (Compound 11)

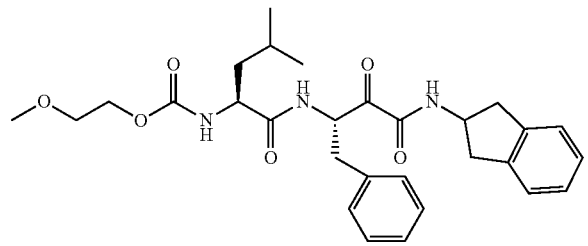 [SMILES: COCCOC(=O)N[C@@H](CC(C)C)C(=O)N[C@@H](Cc1ccccc1)C(=O)C(=O)NC1Cc2ccccc2C1]

The reaction was performed as in Production Example 1 by using the compound of Reference Example 14 in place of the compound of Reference Example 8, thereby yielding the title compound as a colorless crystal, via ((1S)-1-((((1S)-1-benzyl-2-hydroxy-3-(2-indanylamino)-3-oxopropyl)amino) carbonyl)-3-methylbutyl)carbamic acid 2-methoxyethyl ester.

Melting point: 141.9-143.5° C. $^1$H-NMR (300 MHz, DMSO-$d_6$) δ0.83 (d, 3H, J=6.9), 0.86 (d, 3H, J=6.9), 1.36 (m, 2H), 1.57 (m, 1H), 2.80-2.96 (m, 3H), 3.10-3.18 (m, 3H), 3.24 (s, 3H), 3.47 (t, 2H, J=4.7), 4.04 (m, 3H), 4.50 (m, 1H), 5.19 (m, 1H), 7.13-7.30 (m, 10H), 8.29 (d, 1H, J=6.9), 8.97 (d, 1H, J=7.2). MALDI-TOF-MS: $C_{29}H_{37}N_3O_6$ (M+H)$^+$, 524.2760, Actual measurement value, 524.2810.

Production Example 12

((1S)-1-((((1S)-1-Benzyl-2,3-dioxo-3-(2-methoxyethylamino) propyl)amino) carbonyl)-3-methylbutyl) carbamic acid 2-methoxyethyl ester (compound 12)

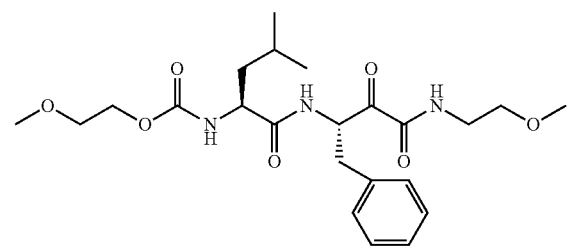

The reaction was performed as in Production Example 1 by using the compound of Reference Example 15 in place of the compound of Reference Example 8, thereby yielding the title compound as a colorless crystal, via ((1S)-1-((((1S)-1-benzyl-2-hydroxy-3-(2-methoxyethylamino)-3-oxopropyl) amino) carbonyl)-3-methylbutyl)carbamic acid 2-methoxyethyl ester.

Melting point: 127.0-127.9° C. $^1$H-NMR (300 MHz, DMSO-$d_6$) 0.83 (d, 3H, J=6.9), 0.86 (d, 3, J=6.9), 1.35 (m, 2H), 1.56 (m, 1H), 2.83 (dd, 1H, J=13.8, 9.0), 3.11 (dd, 1H, J=14.0, 4.4), 3.24 (s, 3H), 3.25 (s, 3H), 3.16-3.34 (m, 2H), 3.39 (m, 2H), 3.48 (t, 2H, J=4.5), 4.04 (m, 3H), 5.20 (m, 1H), 7.18-7.30 (m, 6H), 8.21 (d, 1H, J=6.9), 8.66 (t, 1H, J=5.4). MALDI-TOF-MS: $C_{23}H_{35}N_3O_7$ (M+Na)$^+$, 488.2373, Actual measurement value, 488.2680.

Production Example 13

((1S)-1-((((1S)-2,3-Dioxo-3-ethylamino-1-(phenylethyl)propyl)amino)carbonyl)-3-methylbutyl)carbamic acid 2-methoxyethyl ester (Compound 13)

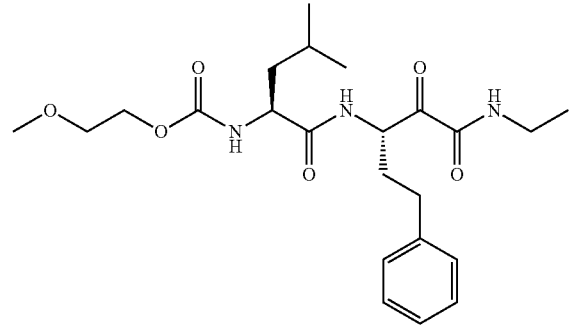 [SMILES: CCNC(=O)C(=O)[C@H](CCc1ccccc1)NC(=O)[C@H](CC(C)C)NC(=O)OCCOC]

The reaction was performed as in Production Example 1 by using the compound of Reference Example 16 in place of the compound of Reference Example 8, thereby yielding the title compound as a colorless crystal, via ((1S)-1-((((1S)-3-ethylamino-2-hydroxy-3-oxo-1-(phenylethyl)propyl)amino)carbonyl)-3-methylbutyl)carbamic acid 2-methoxyethyl ester.

Melting point: 119.1-120.4° C. $^1$H-NMR (300 MHz, DMSO-d$_6$) δ0.89 (t, 6H, J=6.3), 1.03 (t, 3H, J=7.2), 1.43 (t, 2H, J=7.2), 1.61-1.85 (m, 2H), 2.07 (m, 1H), 2.56-2.74 (m, 2H), 3.07-3.17 (m, 2H), 3.25 (s, 3H), 3.49 (t, 2H, J=4.7), 4.05-4.14 (m, 3H), 4.89 (m, 1H), 7.16-7.36 (m, 5H), 7.34 (d, 1H, J=8.4), 8.33 (d, 1H, J=6.9), 8.65 (t, 1H, J=5.9). MALDI-TOF-MS: C$_{23}$H$_{35}$N$_3$O$_6$ (M+H)$^+$, 450.2604, Actual measurement value, 450.2701.

Production Example 14

((1S)-1-((((1S)-2,3-Dioxo-3-ethylamino-1-(phenylethyl)propyl)amino)carbonyl)-3-methylbutyl)carbamic acid (3S)-tetrahydrofuran-3-yl ester (Compound 14)

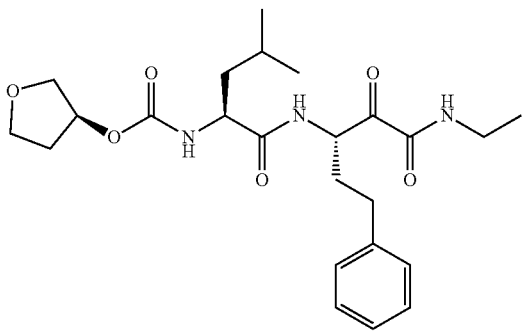 [SMILES: CCNC(=O)C(=O)[C@H](CCc1ccccc1)NC(=O)[C@H](CC(C)C)NC(=O)O[C@H]1CCOC1]

The reaction was performed as in Production Example 1 by using the compound of Reference Example 2 in place of the compound of Reference Example 1, and by using the compound of Reference Example 16 in place of the compound of Reference Example 8, thereby yielding the title compound as a colorless crystal, via ((1S)-1-((((1S)-3-ethylamino-2-hydroxy-3-oxo-1-(phenylethyl)propyl)amino)carbonyl)-3-methylbutyl)carbamic acid (3S)-tetrahydrofuran-3-yl ester.

Melting point: 111.9-114.5° C. $^1$H-NMR (300 MHz, DMSO-d$_6$) δ0.89 (t, 6H, J=6.3), 1.03 (t, 3H, J=7.2), 1.43 (t, 2H, J=7.4), 1.60-1.91 (m, 3H), 2.09 (m, 2H), 2.56-2.76 (m, 2H), 3.07-3.17 (m, 2H), 3.63-3.82 (m, 4H), 4.02-4.13 (m, 1H), 4.88 (m, 1H), 5.09-5.13 (m, 1H), 7.16-7.31 (m, 5H), 7.34 (d, 1H, J=8.4), 8.34 (d, 1H, J=6.9), 8.66 (t, 1H, J=5.7). MALDI-TOF-MS: C$_{24}$H$_{35}$N$_3$O$_6$ (M+H)$^+$, 462.2604, Actual measurement value, 462.2870.

Production Example 15

((1S)-1-((((1S)-2,3-Dioxo-3-cyclopropylamino-1-(phenylethyl)propyl)amino)carbonyl)-3-methylbutyl) carbamic acid 2-methoxyethyl ester (Compound 15)

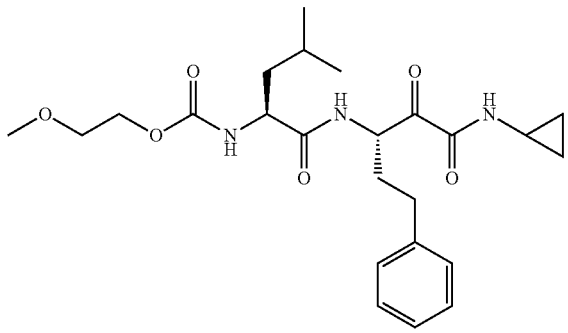 [SMILES: COCCOC(=O)N[C@@H](CC(C)C)C(=O)N[C@@H](CCc1ccccc1)C(=O)C(=O)NC1CC1]

The reaction was performed as in Production Example 1 by using the compound of Reference Example 17 in place of the compound of Reference Example 8, thereby yielding the title compound as a colorless crystal, via ((1S)-1-((((1S)-3-cyclopropylamino-2-hydroxy-3-oxo-1-(phenylethyl) propyl)amino) carbonyl)-3-methylbutyl) carbamic acid 2-methoxyethyl ester.

Melting point: 109.7-111.1° C. $^1$H-NMR (300 MHz, DMSO-d$_6$) δ0.53-0.68 (m, 4H), 0.87-0.91 (m, 6H), 1.43 (t, 3H, J=7.2), 1.59-1.85 (m, 2H), 2.01-2.13 (m, 1H), 2.56-2.74 (m, 3H), 3.25 (s, 3H), 3.48-3.51 (m, 2H), 4.05-4.14 (m, 3H), 4.87 (m, 1H), 7.17-7.36 (m, 6H), 8.34 (d, 1H, J=6.6), 8.69 (d, 1H, J=5.1). MALDI-TOF-MS: C$_{24}$H$_{35}$N$_3$O$_6$ (M+H)+, 462.2604, Actual measurement value, 462.2742.

Production Example 16

((1S)-1-((((1S)-2,3-Dioxo-3-cyclopropylamino))-1-(phenylethyl)propyl)amino)carbonyl)-3-methylbutyl) carbamic acid (3S)-tetrahydrofuran-3-yl ester (Compound 16)

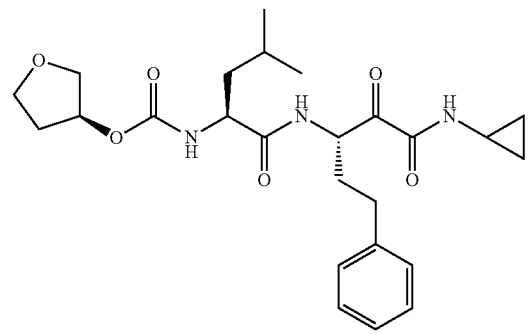 [SMILES: CC(C)C[C@H](NC(=O)O[C@H]1CCOC1)C(=O)N[C@@H](CCc1ccccc1)C(=O)C(=O)NC1CC1]

The reaction was performed as in Production Example 1 by using the compound of Reference Example 2 in place of the compound of Reference Example 1, and by using the compound of Reference Example 17 in place of the compound of Reference Example 8, thereby yielding the title compound as a colorless crystal, via ((1S)-1-((((1S)-3-cyclopropylamino-2-hydroxy-3-oxo-1-(phenylethyl)propyl)amino)carbonyl)-3-methylbutyl) carbamic acid (3S)-tetrahydrofuran-3-yl ester.

Melting point: 115.8-116.2° C. $^1$H-NMR (300 MHz, DMSO-d$_6$) δ0.56-0.59 (m, 4H), 0.88 (t, 6H, J=6.3), 1.42 (t, 2H, J=7.4), 1.60-1.91 (m, 3H), 2.09 (m, 2H), 2.56-2.76 (m, 3H), 3.63-3.81 (m, 4H), 4.05-4.13 (m, 1H), 4.87 (m, 1H), 5.09-5.13 (m, 1H), 7.20-7.35 (m, 6H), 8.34 (d, 1H, J=6.9), 8.69 (d, 1H, J=5.1). MALDI-TOF-MS: C$_{25}$H$_{35}$N$_3$O$_6$ (M+H)$^+$, 474.2604, Actual measurement value, 474.2598.

Production Example 17

((1S)-1-((((1S)-1-Benzyl-2,3-dioxo-3-(cyclopropylamino)propyl)amino)carbonyl)-3-methylbutyl)carbamic acid 5-methoxy-3-oxapentyl ester (compound 17)

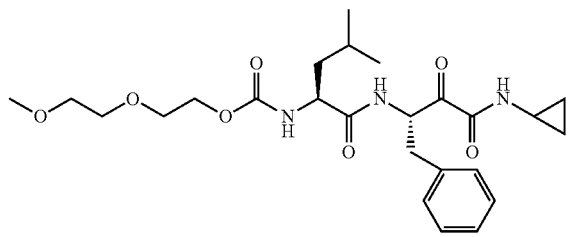 [SMILES: COCCOCCOC(=O)N[C@@H](CC(C)C)C(=O)N[C@@H](Cc1ccccc1)C(=O)C(=O)NC1CC1]

The reaction was performed as in Production Example 1 by using the compound of Reference Example 4 in place of the compound of Reference Example 1, and by using the compound of Reference Example 9 in place of the compound of Reference Example 8, thereby yielding the title compound as a colorless crystal, via ((1S)-1-((((1S)-1-benzyl-3-cyclopropylamino-2-hydroxy-3-oxopropyl)amino)carbonyl)-3-methylbutyl) carbamic acid 5-methoxy-3-oxapentyl ester.

Melting point: 127.9-128.7° C. H-NMR (300 MHz, DMSO-d$_6$) δ0.54-0.66 (m, 4H), 0.81-0.86 (m, 6H), 1.30-1.42 (m, 2H), 1.57 (m, 1H), 2.73 (m, 1H), 2.82 (dd, 1H, J=14.3, 9.2), 3.11 (dd, 1H, J=13.8, 4.2), 3.24 (s, 3H), 3.42-3.44 (m, 2H), 3.50-3.57 (m, 4H), 3.99-4.04 (m, 3H), 5.17 (m, 1H), 7.22-7.30 (m, 6H), 8.22 (d, 1H, J=6.9), 8.71 (d, 1H, J=4.8). MALDI-TOF-MS: C$_{25}$H$_{37}$N$_3$O$_7$ (M+Na)$^+$, 514.2530, Actual measurement value, 514.2944. [α]$_D^{25}$+13.9° (c0.20, DMSO)

Production Example 18

((S)-1-((((S)-1-Benzyl-2,3-dioxo-3-(cyclopropylamino) propyl)amino) carbonyl)-3-methylbutyl) carbamic acid 8-methoxy-3,6-dioxaoctyl ester (Compound 18)

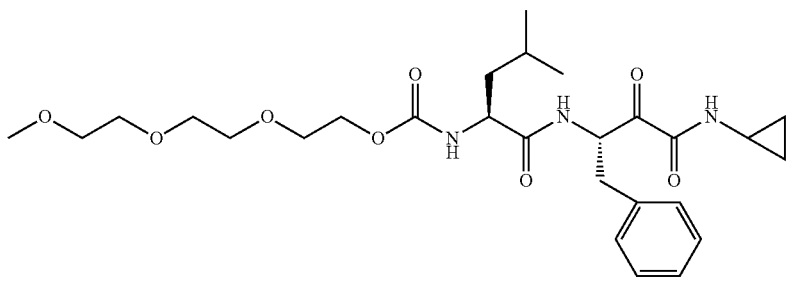 [SMILES: COCCOCCOCCOC(=O)N[C@@H](CC(C)C)C(=O)N[C@@H](Cc1ccccc1)C(=O)C(=O)NC1CC1]

The reaction was performed as in Production Example 1 by using the compound of Reference Example 5 in place of the compound of Reference Example 1, and by using the compound of Reference Example 9 in place of the compound of Reference Example 8, thereby yielding the title compound as a colorless crystal, via ((1S)-1-((((1S)-1-benzyl-3-cyclopropylamino-2-hydroxy-3-oxopropyl)amino) carbonyl)-3-methylbutyl) carbamic acid 8-methoxy-3,6-dioxaoctyl ester.

Melting point: 116.0-117.2° C. $^1$H-NMR (300 MHz, DMSO-d$_6$) δ0.58 (m, 2H), 0.65 (m, 2H), 0.83 (d, 3H, J=7.8), 0.85 (d, 3H, J=6.9), 1.35 (m, 2H), 1.57 (m, 1H), 2.73-2.86 (m, 2H), 3.11 (m, 1H), 3.24 (s, 3H), 3.44 (m, 2H), 3.51 (m, 6H), 3.56 (t, 2H, J=4.7), 4.04 (m, 3H), 5.17 (m, 1H), 7.22-7.31 (m, 6H), 8.25 (d, 1H, J=6.9), 8.73 (d, 1H, J=5.1). MALDI-TOF-MS: C$_{27}$H$_{41}$N$_3$O$_8$ (M+Na)$^+$, 558.2792, Actual measurement value, 558.2717. [α]$_D^{25}$+2.5° (c0.20, DMSO)

Production Example 19

((1S)-1-((((1S)-1-Benzyl-2,3-dioxo-3-(cyclopropylamino)propyl)amino)carbonyl)-3-methylbutyl)carbamic acid 11-methoxy-3,6,9-trioxaundecanyl ester (Compound 19)

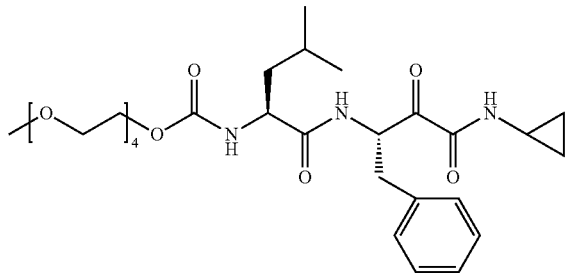

The reaction was performed as in Production Example 1 by using the compound of Reference Example 6 in place of the compound of Reference Example 1, and by using the compound of Reference Example 9 in place of the compound of Reference Example 8, thereby yielding the title compound as a colorless crystal, via ((1S)-1-((((1S)-1-benzyl-3-cyclopropylamino-2-hydroxy-3-oxopropyl)amino) carbonyl)-3-methylbutyl) carbamic acid 11-methoxy-3,6,9-trioxaundecanyl ester.

Melting point: 97.5-98.5° C. $^1$H-NMR (300 MHz, DMSO-d$_6$) δ0.54-0.66 (m, 4H), 0.81-0.86 (m, 6H), 1.32-1.37 (m, 2H), 1.56 (m, 1H), 2.73 (m, 1H), 2.82 (dd, 1H, J=14.0, 9.2), 3.11 (dd, 1H, J=14.1, 4.2), 3.24 (s, 3H), 3.41-3.44 (m, 2H), 3.50-3.51 (m, 10H), 3.54-3.57 (m, 2H), 3.99-4.08 (m, 3H), 5.16 (m, 1H), 7.22-7.31 (m, 6H), 8.25 (d, 1H, J=7.2), 8.73 (d, 1H, J=5.1). MALDI-TOF-MS: $C_{29}H_{45}N_3O_9$ (M+Na)$^+$, 602.3054, Actual measurement value, 602.3427. $[\alpha]_D^{25}$+6.9° (c0.20, DMSO)

Production Example 20

((1S)-1-((((1S)-1-Benzyl-2,3-dioxo-3-(cyclopropylamino)propyl)amino)carbonyl)-3-methylbutyl)carbamic acid 14-methoxy-3,6,9,12-tetraoxatetradecanyl ester (Compound 20)

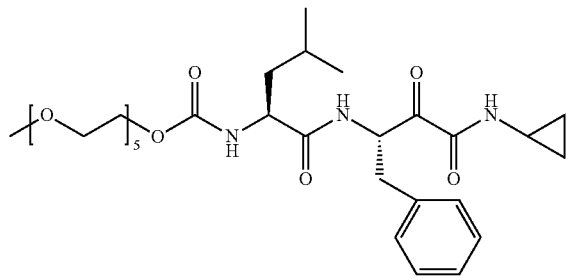

The reaction was performed as in Production Example 1 by using the compound of Reference Example 7 in place of the compound of Reference Example 1, and by using the compound of Reference Example 9 in place of the compound of Reference Example 8, thereby yielding the title compound as a colorless crystal, via ((1S)-1-((((1S)-1-benzyl-3-cyclopropylamino-2-hydroxy-3-oxopropyl)amino) carbonyl)-3-methylbutyl) carbamic acid 14-methoxy-3,6,9,12-tetraoxatetradecanyl ester.

Melting point: 98.5-99.9° C. $^1$H-NMR (300 MHz, DMSO-d$_6$) δ0.58 (m, 2H), 0.65 (m, 2H), 0.83 (d, 3H, J=6.9), 0.85 (d, 3H, J=7.8), 1.35 (m, 2H), 1.57 (m, 1H), 2.73-2.86 (m, 2H), 3.11 (m, 1H), 3.24 (s, 3H), 3.42 (m, 2H), 3.51 (m, 14H), 3.56 (t, 2H, J=3.3), 4.04 (m, 3H), 5.17 (m, 1H), 7.22-7.30 (m, 6H), 8.24 (d, 1H, J=6.9), 8.72 (d, 1H, J=4.5). MALDI-TOF-MS: $C_{31}H_4N_3O_{10}$ (M+Na)$^+$, 646.3316, Actual measurement value, 646.3404.

Production Example 21

((1S)-1-((((1S)-2,3-Dioxo-1-(2-methylpropyl)-3-(2-phenoxyethyl)aminopropyl)amino) carbonyl)-3-methylbutyl) carbamic acid 2-methoxyethyl ester (Compound 21)

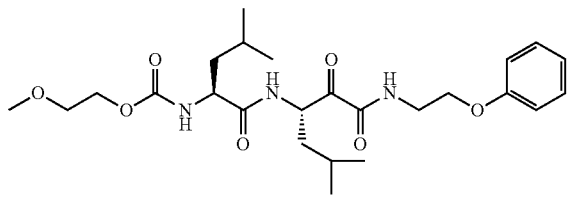 [SMILES: COCCOC(=O)N[C@@H](CC(C)C)C(=O)N[C@@H](CC(C)C)C(=O)C(=O)NCCOc1ccccc1]

The reaction was performed as in Production Example 1 by using the compound of Reference Example 18 in place of the compound of Reference Example 8, thereby yielding the title compound as a colorless crystal, via ((1S)-1-((((1S)-2-hydroxy-1-(2-methylpropyl)-3-oxo-3-(2-phenoxyethyl)aminopropyl)amino)carbonyl)-3-methylbutyl)carbamic acid 2-methoxyethyl ester.

Melting point: 99.7-100.5° C. $^1$H-NMR (300 MHz, DMSO-d$_6$) δ0.88 (dd, 12H, J=12.0, 6.3), 1.35-1.54 (m, 4H), 1.58-1.75 (m, 2H), 3.25 (s, 3H), 3.46-3.53 (m, 4H), 4.03-4.07 (m, 5H), 5.06 (m, 1H), 6.91-6.95 (m, 3H), 7.26-7.31 (m, 3H), 8.15 (d, 1H, J=7.2), 8.81 (t, 1H, J=5.9). MALDI-TOF-MS: $C_{25}H_{39}N_3O_7$ (M+H)$^+$, 494.2866, Actual measurement value, 494.2967.

Production Example 22

((1S)-1-((((1S)-2,3-Dioxo-1-(2-methylpropyl)-3-(2-phenoxyethyl)aminopropyl)amino) carbonyl)-3-methylbutyl) carbamic acid 5-methoxy-3-oxapentyl ester (compound 22)

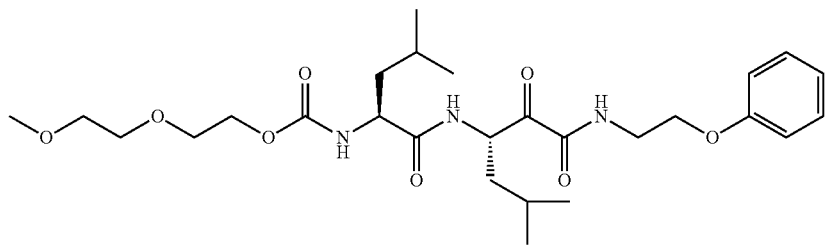 [SMILES: COCCOCCOC(=O)N[C@@H](CC(C)C)C(=O)N[C@@H](CC(C)C)C(=O)C(=O)NCCOc1ccccc1]

The reaction was performed as in Production Example 1 by using the compound of Reference Example 4 in place of the compound of Reference Example 1, and by using the compound of Reference Example 18 in place of the compound of Reference Example 8, thereby yielding the title compound as a colorless crystal, via ((1S)-1-((((1S)-2-hydroxy-1-(2-methylpropyl)-3-oxo-3-(2-phenoxyethyl)aminopropyl)amino)carbonyl)-3-methylbutyl) carbamic acid 5-methoxy-3-oxapentyl ester.

Melting point: 53.3-54.1° C. $^1$H-NMR (300 MHz, DMSO-d$_6$) δ0.87 (dd, 12H, J=12.2, 6.5), 1.35-1.54 (m, 4H), 1.58-1.75 (m, 2H), 3.24 (s, 3H), 3.41-3.45 (m, 2H), 3.47-3.57 (m, 6H), 4.03-4.07 (m, 5H), 5.06 (m, 1H), 6.91-6.96 (m, 3H), 7.26-7.31 (m, 3H), 8.17 (d, 1H, J=6.9), 8.83 (t, 1H, J=5.7). MALDI-TOF-MS: $C_{27}H_{43}N_3O_8$ (M+H)$^+$, 538.3128, Actual measurement value, 538.3140.

Production Example 23

((1S)-1-((((1RS)-3-Amino-1-benzyl-2,3-dioxopropyl)amino)carbonyl)-3-methylbutyl) carbamic acid 5-methoxy-3-oxapentyl ester (Compound 23)

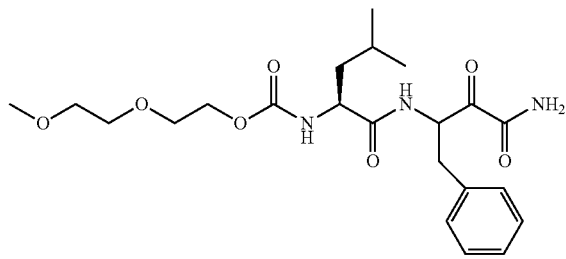 [SMILES: COCCOCCOC(=O)N[C@@H](CC(C)C)C(=O)NC(Cc1ccccc1)C(=O)C(N)=O]

The reaction was performed as in Production Example 1 by using the compound of Reference Example 4 in place of the compound of Reference Example 1, and by using the compound of Reference Example 19 in place of the compound of Reference Example 8, thereby yielding the title compound as a colorless crystal, via ((1S)-1-((((1RS)-β-amino-1-benzyl-2-hydroxy-3-oxopropyl)amino) carbonyl)-3-methylbutyl) carbamic acid 5-methoxy-3-oxapentyl ester.

$^1$H-NMR (300 MHz, DMSO-d$_6$) δ0.77 (d, 3H, J=6.3), 0.83 (d, 1.5H, J=6.6), 0.86 (d, 1.5H, J=6.9), 1.05-1.63 (m, 3H), 2.68-2.85 (m, 1H), 3.12 (m, 1H), 3.23 (s, 3H), 3.42 (m, 2H), 3.51-3.56 (m, 4H), 4.03 (m, 3H), 5.22 (m, 1H), 7.21-7.31 (m, 6H), 7.81 (d, 1H, J=14), 8.06 (d, 1H, J=18), 8.19 (d, 0.5H, J=6.9), 8.26 (d, 0.5H, J=7.5).

Production Example 24

((1S)-1-((((1S)-1-Benzyl-3-(cyclopropylamino)-2,3-dioxopropyl)amino) carbonyl)-3-methylbutyl) carbamic acid 2-(pyridin-2-yl)ethyl ester (Compound 24)

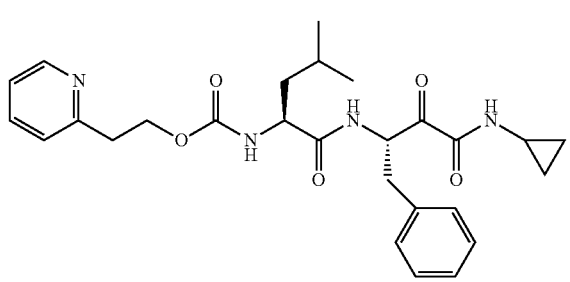 [SMILES: CC(C)C[C@H](NC(=O)OCCc1ccccn1)C(=O)N[C@@H](Cc1ccccc1)C(=O)C(=O)NC1CC1]

The reaction was performed as in Production Example 1 by using the compound of Reference Example 20 in place of the compound of Reference Example 1, and by using the compound of Reference Example 9 in place of the compound of Reference Example 8, thereby yielding the title compound as a colorless crystal, via (((1S)-1-((((1S)-1-benzyl-3-(cyclopropylamino)-2-hydroxy-3-oxopropyl)amino) carbonyl)-3-methylbutyl) carbamic acid 2-(pyridin-2-yl)ethyl ester.

$^1$H-NMR (300 MHz, DMSO-d$_6$) δ0.58-0.66 (m, 4H), 0.83 (t, 6H, J=7.1), 1.31-1.35 (m, 2H), 1.53 (m, 1H), 2.74 (m, 1H), 2.81 (dd, 1H, J=14.1, 9.3), 3.02 (t, 2H, J=6.3), 3.11 (dd, 1H, J=14.0, 4.1), 4.01 (m, 1H), 4.28-4.32 (m, 2H), 5.17 (m, 1H), 7.14-7.34 (m, 8H), 7.75 (t, 1H, J=6.8), 8.23 (d, 1H, J=7.2), 8.51 (d, 1H, J=4.2), 8.71 (d, 1H, J=4.5).

Production Example 25

((1S)-1-((((1S)-1-Benzyl-3-(cyclopropylamino)-2,3-dioxopropyl)amino)carbonyl)-3-methylbutyl)carbamic acid 2-(6-methylpyridin-2-yl)ethyl ester (Compound 25)

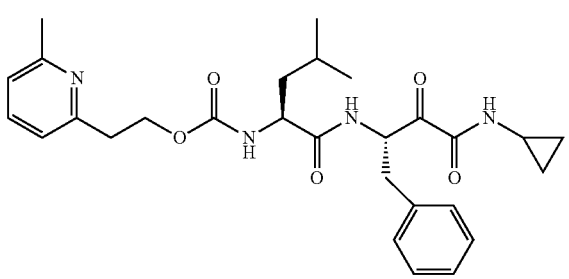 [SMILES: Cc1cccc(CCOC(=O)N[C@@H](CC(C)C)C(=O)N[C@@H](Cc2ccccc2)C(=O)C(=O)NC2CC2)n1]

The reaction was performed as in Production Example 1 by using the compound of Reference Example 21 in place of the compound of Reference Example 1, and by using the compound of Reference Example 9 in place of the compound of Reference Example 8, thereby yielding the title compound as a colorless crystal, via (((1S)-1-((((1S)-1-benzyl-3-(cyclopropylamino)-2-hydroxy-3-oxopropyl)amino) carbonyl)-3-methylbutyl) carbamic acid 2-(6-methylpyridin-2-yl)ethyl ester.

Melting point: 162.0-163.6° C.

$^1$H-NMR (300 MHz, DMSO-d$_6$) δ0.54-0.66 (m, 4H), 0.76-0.86 (m, 6H), 1.54 (m, 1H), 2.43 (s, 3H), 2.73-2.86 (m, 2H), 2.96 (t, 2H, J=6.5), 3.11 (m, 1H), 4.03 (m, 1H), 4.21-4.34 (m, 2H), 5.17 (m, 1H), 7.07-7.30 (m, 8H), 7.58 (t, 1H, J=7.7), 8.23 (d, 1H, J=6.9), 8.72 (d, 1H, J=4.8).

Production Example 26

((1S)-1-((((1S)-1-Benzyl-3-(cyclopropylamino)-2,3-dioxopropyl)amino)carbonyl)-3-methylbutyl) carbamic acid 2-(5-ethylpyridin-2-yl)ethyl ester (compound 26)

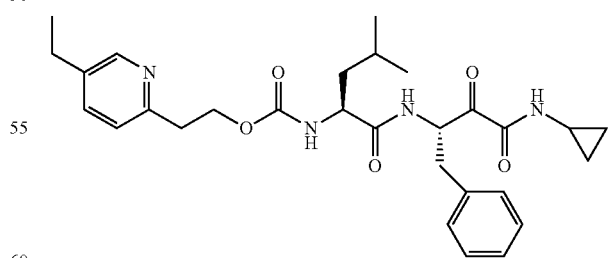

The reaction was performed as in Production Example 1 by using the compound of Reference Example 22 in place of the compound of Reference Example 1, and by using the compound of Reference Example 9 in place of the compound of Reference Example 8, thereby yielding the title compound as a colorless crystal, via (((1S)-1- benzyl-3-(cyclopropylamino)-2-hydroxy-3-oxopropyl) amino) carbonyl)-3-methylbutyl) carbamic acid 2-(5-ethylpyridin-2-yl)ethyl ester.

Melting point: 119.9-121.0° C.

$^1$H-NMR (300 MHz, DMSO-$d_6$) δ0.58-0.66 (m, 4H), 0.75-0.85 (m, 6H), 1.17 (t, 3H, J=7.7), 1.33-1.36 (m, 2H), 1.53 (m, 1H), 2.58 (dd, 2H, J=15.5, 8.3), 2.74-2.85 (m, 2H), 2.94-2.98 (m, 2H), 3.12 (m, 1H), 4.04 (m, 1H), 4.28-4.29 (m, 2H), 5.17 (m, 1H), 7.13-7.26 (m, 7H), 7.55 (d, 1H, J=8.1), 8.22-8.35 (m, 2H), 8.75 (m, 1H).

Production Example 27

((1S)-1-((((S)-1-Benzyl-3-(cyclopropylamino)-2,3-dioxopropyl)amino) carbonyl)-3-methylbutyl) carbamic acid 2-tert-butoxy ethyl ester (Compound 27)

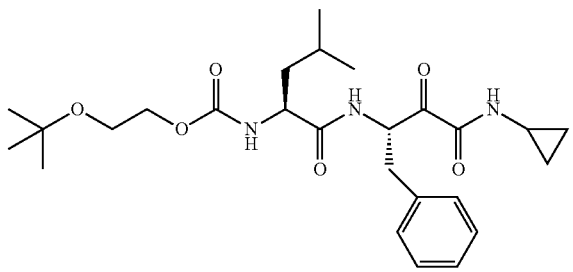 [SMILES: CC(C)C[C@H](NC(=O)OCCOC(C)(C)C)C(=O)N[C@@H](Cc1ccccc1)C(=O)C(=O)NC1CC1]

The reaction was performed as in Production Example 1 by using the compound of Reference Example 23 in place of the compound of Reference Example 1, and by using the compound of Reference Example 9 in place of the compound of Reference Example 8, thereby yielding the title compound as a colorless crystal, via (((1S)-1-((((1S)-1-benzyl-3-(cyclopropylamino)-2-hydroxy-3-oxopropyl) amino) carbonyl)-3-methylbutyl) carbamic acid 2-tert-butoxy ethyl ester.

$^1$H-NMR (300 MHz, DMSO-$d_6$) δ0.58 (m, 2H), 0.65 (m, 2H), 0.83 (d, 3H, J=7.5), 0.85 (d, 3H, J=6.9), 1.12 (s, 9H), 1.35 (m, 2H), 1.57 (m, 1H), 2.74 (m, 1H), 2.82 (m, 1H), 3.11 (m, 1H), 3.45 (m, 2H), 3.98 (m, 3H), 5.17 (m, 1H), 7.24 (m, 6H), 8.23 (d, 1H, J=6.6), 8.71 (d, 1H, J=4.8).

Production Example 28

((1S)-1-((((1S)-1-Benzyl-3-(cyclopropylamino)-2,3-dioxopropyl)amino)carbonyl)-3-methylbutyl) carbamic acid 2-isopropoxyethyl ester (Compound 28)

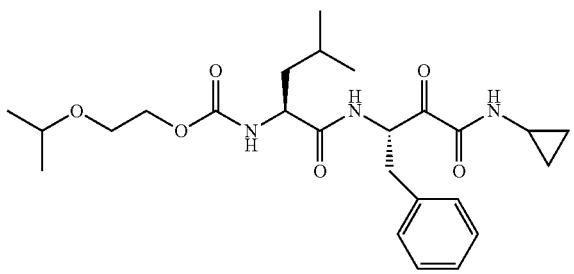 [SMILES: CC(C)C[C@H](NC(=O)OCCOC(C)C)C(=O)N[C@@H](Cc1ccccc1)C(=O)C(=O)NC1CC1]

The reaction was performed as in Production Example 1 by using the compound of Reference Example 24 in place of the compound of Reference Example 1, and by using the compound of Reference Example 9 in place of the compound of Reference Example 8, thereby yielding the title compound as a colorless crystal, via (((1S)-1-((((1S)-1-benzyl-3-(cyclopropylamino)-2-hydroxy-3-oxopropyl) amino) carbonyl)-3-methylbutyl) carbamic acid 2-isopropoxyethyl ester.

$^1$H-NMR (300 MHz, DMSO-$d_6$) δ0.58 (m, 2H), 0.65 (m, 2H), 0.83 (d, 3H, J=7.2), 0.85 (d, 3H, J=6.9), 1.07 (d, 6H, J=5.7), 1.35 (m, 2H), 1.57 (m, 1H), 2.74 (m, 1H), 2.82 (m, 1H), 3.12 (m, 1H), 3.50 (m, 2H), 3.55 (m, 1H), 4.01 (m, 3H), 5.17 (m, 1H), 7.24 (m, 6H), 8.22 (d, 1H, J=6.9), 8.71 (d, 1H, J=3.6).

Measurement of Inhibitory Activity Against μ-Calpain and m-Calpain

The inhibitory activity against μ-calpain and m-calpain was assayed according to a published method (Anal. Biochem. 1993, vol. 208, p. 387-392). More specifically, 200 μL of a reaction solution containing 0.5 mg/mL casein, 50 mM Tris-HCl buffer (pH 7.4), 20 mM dithiothreitol and 1.0 nmol μ-calpain (derived from human red blood cells, Cosmo Bio Co., Ltd.) or m-calpain (derived from porcine kidney, Cosmo Bio Co., Ltd.) was added to individual 2.5 μL portions of DMSO solution containing a varying concentration of a test sample in a 96-well plate. Then, 50 μL of 20 mM aqueous calcium chloride was added thereto, and reaction was performed at 30° C. for 60 minutes. 100 μL of the reaction solution was transferred to another 96-well plate, and purified water (50 μL) and 50% aqueous solution (100 μL) of Protein Assay Dye Reagent (available from Bio-Rad Laboratories, Inc.; catalogue No. 500-600) were added thereto. The reaction mixture was allowed to stand at room temperature for 15 minutes, and its absorbance was measured at 595 nM. The absorbance of a reaction mixture prepared in the same manner as mentioned above, except that a DMSO solution containing no sample was used as a control value; and the absorbance of a reaction mixture prepared in the same manner as mentioned above, except that a 1 mM aqueous EDTA solution (50 μL) was used in place of 20 mM aqueous calcium chloride, was used as a blank value. The inhibition rate was calculated according to the following equation, and the concentration required for 50% inhibition ($IC_{50}$) was determined.

Inhibition rate(%)={1−(measured value−blank test value)/(control value−blank test value)}×100

The concentrations ($IC_{50}$) are shown in Table 1 as enzyme (calpain) inhibitory activities (μM). The compounds inhibited activities of μ-calpain and m-calpain.

TABLE 1

| | Enzyme inhibitory activity (μM) | |
|---|---|---|
| Compound | μ-Calpain | m-Calpain |
| Compound 1 | 0.17 | 0.11 |
| Compound 2 | 0.15 | 0.11 |
| Compound 3 | 0.25 | 0.16 |
| Compound 4 | 0.11 | 0.10 |
| Compound 5 | 0.09 | 0.05 |
| Compound 6 | 0.12 | 0.13 |
| Compound 7 | 0.10 | 0.07 |
| Compound 8 | 0.17 | 0.08 |
| Compound 9 | 0.10 | 0.14 |
| Compound 10 | 0.45 | 0.34 |
| Compound 11 | 0.17 | 0.12 |

TABLE 1-continued

| Compound | Enzyme inhibitory activity (μM) | |
| --- | --- | --- |
| | μ-Calpain | m-Calpain |
| Compound 12 | 0.18 | 0.11 |
| Compound 13 | 0.30 | 0.20 |
| Compound 14 | 0.16 | 0.20 |
| Compound 15 | 0.18 | 0.14 |
| Compound 16 | 0.14 | 0.10 |
| Compound 17 | 0.17 | 0.10 |
| Compound 18 | 0.19 | 0.12 |
| Compound 19 | 0.22 | 0.17 |
| Compound 20 | 0.42 | 0.19 |
| Compound 21 | 0.08 | 0.11 |
| Compound 22 | 0.09 | 0.16 |
| Compound 23 | 0.19 | 0.18 |
| Compound 24 | 0.029 | 0.017 |

Among these compounds, Compound 17 was used for the following analysis. Compound 17 is SNJ-1945. Hereunder, Compound 17 is also referred to as SNJ-1945.

The test animals and test cells used in the analysis below were prepared basically in the same manner as in the aforementioned Non-Patent Document 1 (Masami Yamada et al., Nature Medicine 15, 1202-1207 (2009)). In experiments in which test animals are killed, the test animals were anesthetized using a fatal dose of ether, and euthanized.

Experiment of Axon Regeneration Using Dorsal Root Ganglion Neurons (DRG Neurons)

Axons of nerve cells severed due to external injury may extend towards target cells and reconstruct the neural network. This is called "axon regeneration." Peripheral nerve axons have the potential of being regenerated across a damaged region. However, the regeneration ability declines with increasing age. To analyze the correlation between age and axon regeneration, the following experiment was performed using mouse dorsal root ganglion neurons. Since dorsal root ganglion neurons extend only axons, they are suitable for observation of axon regeneration.

Dorsal root ganglions were aseptically extracted from postnatal mice (3, 10, or 15 days old) under a stereoscopic microscope, and tissue fragments were dispersed by gentle pipetting and then treated with 0.025% trypsin/0.0013% DNaseI (both being final concentrations) at 37° C. for 20 minutes. After centrifugation, a BME culture solution (Gibco) containing 10% equine blood serum was added, and washing was performed. After the enzyme reaction was stopped, a BME culture solution containing 0.0052% DNaseI/10% equine blood serum (both being final concentrations) was added, and pipetting was performed. After the resulting mixture was filtered through a cell mesh (cell strainer, diameter: 70 μm, Becton Dickinson), the filtrate was transferred to a BME culture solution containing a nutritional supplement (N-2 supplement; Gibco), and incubated at 37° C. under 5% $CO_2$ for 24 to 48 hours in a 6-well plate (Nunc) in which cover glass (24×24 mm; Matsunami Glass Ind., Ltd.) treated with poly-L-lysine (Sigma) and laminin (Sigma) had been laid down. After washing with phosphate buffer (PBS), the cells were fixed in 4% paraformaldehyde (at room temperature for 15 minutes) and treated with 0.2% Triton X-100 (at room temperature for 10 minutes). For axon analysis, Tuj1 antibody (a mouse-monoclonal-antibody ab14545: Abcam), which is an anti-neuron-specific 3-III tubulin monoclonal antibody, was added. For nuclear staining, DAPI (4',6-diamino-2-phenylindole) was added to achieve a final concentration of 0.2 μM. After incubation for another 15 minutes at room temperature, the resulting aggregates were washed well and carefully embedded using glycerol for fluorescence microscope observation (Merck) so as not to break up the aggregates. Observation was performed using a confocal laser microscope (TCS-SP5, Leica). Dorsal root ganglion neurons were also isolated from LIS1 hetero mice (3 days old) and analyzed in the same manner.

Figure 1:
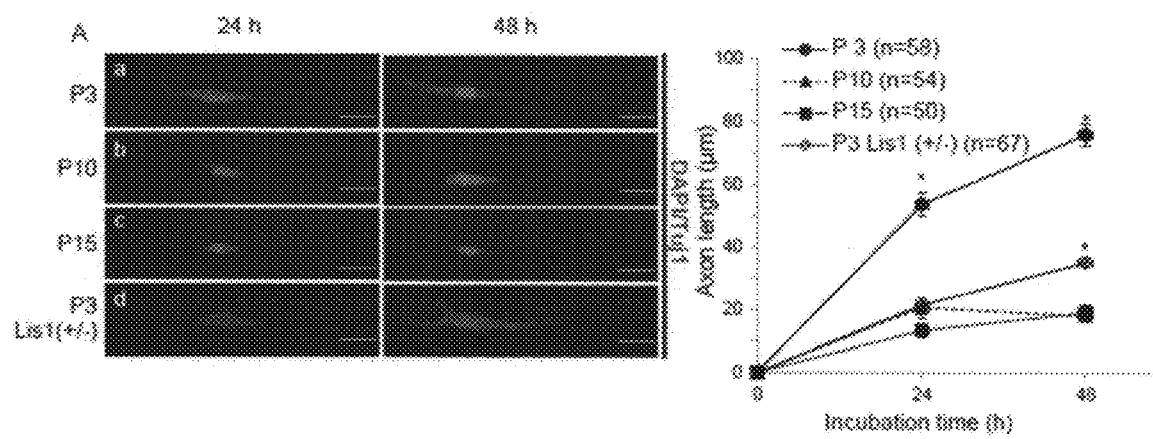

After 24 hours, long axon elongation was observed in the dorsal root ganglion neurons isolated from the 3-day-old mice, whereas significantly reduced axon elongation was observed in the dorsal root ganglion neurons isolated from the 10-day-old mice or 15-day-old mice. Further, poor axon elongation was observed in the dorsal root ganglion neurons isolated from LIS1 hetero mice (3 days old) (FIG. 1).

Analysis of Expression Amount of LIS1 Protein in Dorsal Root Ganglion Neurons

Figure 2:
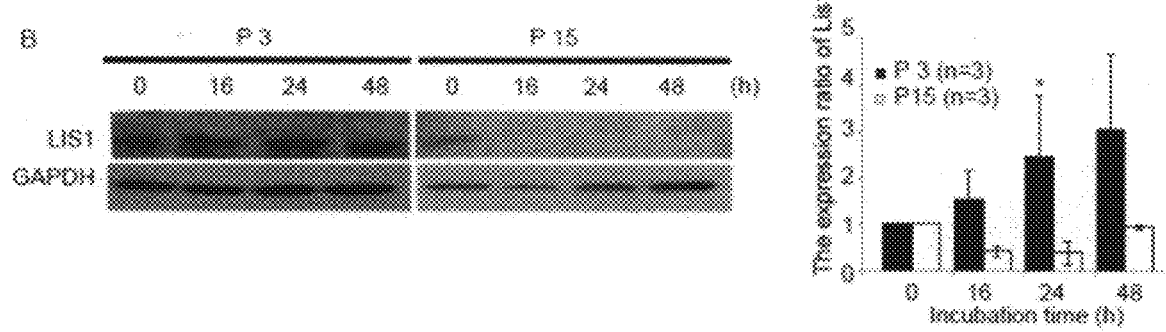

Dorsal root ganglion neurons were isolated from mice (3 days old or 15 days old) and the expression amount of LIS1 protein was analyzed in the order of time sequence from initiation of culture. Protein extraction was performed by adding 100 μl of a protein-dissolving liquid (30 mM Tris-HCl, pH 6.8, 1.5% sodium dodecyl sulfate (SDS), 0.3% bromophenol blue (BPB), 0.3% 2-mercapto-ethanol (2-ME), and 15% glycerol) per $5×10^4$ dorsal root ganglion neurons and further performing ultrasonic treatment to achieve complete solubilization. After the heat treatment at 95° C. for 5 minutes, 1 μl of the obtained protein lysate was separated by 12.5% SDS-acrylamide electrophoresis and subjected to western blotting using anti-LIS1 antibody to detect LIS protein (the left-side figure in FIG. 2). The intensity of the detected band was analyzed (after correction with the intensity of the GAPDH band), and the expression ratio of LIS protein was determined (right-side figure in FIG. 2). The results revealed that LIS1 is strongly induced when dorsal root ganglion neurons extend axons. Further, a high correlation was observed between LIS1 induction and ability to extend axons. The results show that the dorsal root ganglion neurons isolated from the 3-day-old mice had a larger expression amount than the dorsal root ganglion neurons isolated from the 15-day-old mice.

Analysis of Effect of Acceleration of Lis1 Gene Expression on Axon Elongation of Mouse Dorsal Root Ganglion Neurons Because involvement of LIS1 in axon elongation of mouse dorsal root ganglion neurons was suggested, the relationship between axon elongation and SNJ1945, which has an effect of amplifying LIS1 protein, was analyzed. WO2012/074120 discloses that SNJ1945 has an effect of amplifying LIS1 protein based on its excellent calpain inhibitory activity.

Dorsal root ganglions were aseptically isolated from postnatal mice (3 days old or 15 days old) under a stereoscopic microscope and tissue fragments were dispersed by gentle pipetting and then treated with 0.025% trypsin/0.0013% DNaseI (both being final concentrations) at 37° C. for 20 minutes. After centrifugation, a BME culture solution (Gibco) containing 10% equine blood serum was added and washing was performed. After the enzyme reaction was stopped, a BME culture solution containing 0.0052% DNaseI/10% equine blood serum (both being final concentrations) was added, and pipetting was performed. The resulting mixture was filtered through a cell mesh (Cell strainer, diameter: 70 μm; Becton Dickinson) and then centrifuged at 1000 revolutions per minute. The expression vector of LIS1 was prepared by linking cDNA (accession No. Mm. 397111) of mouse LIS1 to the cloning site of pEGFP vector (Clonetech). Using a Neon electroporation device (Invitrogen), 1 μg of a pEGFP vector having LIS1 integrated was introduced into 1×10⁶ dorsal root ganglion neurons, and the resulting neurons were incubated at 37° C. and 5% $CO_2$ for 24 or 48 hours to express LIS1. Dorsal root ganglion neurons having 1 μg of a simple pEGFP vector introduced into them were used as a control. Each neuron was observed under a confocal laser microscope in a similar manner as in the axon regeneration experiment described above.

The dorsal root ganglion neurons isolated from the 3-day-old mice exhibited significant axon elongation as shown in the analysis results above. Although an axon elongation promotion effect by acceleration of Lis1 gene expression was observed, the dorsal root ganglion neurons isolated from the 3-day-old mice originally had high ability to extend axons, and no significant difference was observed. In contrast, the dorsal root ganglion neurons isolated from 15-day-old mice had low ability to extend exons. The results show that axon elongation in the dorsal root ganglion neurons isolated from 15-day-old mice was significantly promoted by acceleration of Lis1 gene expression (FIG. 3).

Analysis of Effect of SNJ1945 on Axon Elongation in Mouse Dorsal Root Ganglion Neurons Dorsal root ganglion neurons were isolated from 3-day-old mice or 15-day-old mice, and the correlation between the presence or absence of SNJ1945 addition and axon length was analyzed. SNJ1945 was added to the isolated dorsal root ganglion neurons to a final concentration of 200 μM, and the neurons were incubated at 37° C. and 5% $CO_2$ for 24 hours or 48 hours. As a control experiment, 1% dimethyl sulfoxide (DMSO) was added in place of SNJ1945, and the neurons were incubated in the same manner. Observation under a confocal laser microscope was performed in the same manner as in the axon regeneration experiment described above.

The dorsal root ganglion neurons isolated from the 3-day-old mice had an ability to extend axons as shown in the analysis results above. Further, an axon elongation promotion effect by addition of SNJ1945 was also observed. The dorsal root ganglion neurons isolated from the 15-day-old mice had low ability to extend axons and also exhibited a low expression amount of LIS1 (c in FIG. 4). The results show that SNJ1945 exhibited a significant axon elongation promotion effect in the dorsal root ganglion neurons isolated from the 15-day-old mice (FIG. 4).

After the incubation, the procedures were performed in the same manner as described above in the "Analysis of Expression Amount of LIS1 Protein in Dorsal Root Ganglion Neurons" section to detect LIS protein by western blotting (the left-side figure in FIG. 5). Further, the intensity of the detected band was analyzed to determine the expression ratio of the LIS protein (the right-side figure in FIG. 5). The results show that the expression amount of LIS protein in dorsal root ganglion neurons isolated from the 3-day-old mice was originally high and addition of SNJ1945 was not able to significantly increase the expression amount, whereas the expression amount of LIS1 in the dorsal root ganglion neurons isolated from the 15-day-old mice was low, and addition of SNJ1945 significantly increased the expression amount of LIS1 (FIG. 5).

Determination of the LIS1 Gene Expression Regulatory Region

To identify the transcriptional regulatory region of LIS1 gene, luciferase reporter assay was performed. A plasmid in which a luciferase gene was joined to the 3' end of a DNA fragment comprising a transcriptional regulatory region (pGV3 reporter-gene vector) was constructed and introduced into root ganglion neurons isolated from mice. More specifically, using a Neon electroporation device (Invitrogen), the plasmid was introduced into 1×10⁶ dorsal root ganglion neurons isolated from 3-day-old mice or 15-day-old mice. *Renilla* luciferase expression vector pRLSV40 was introduced into the neurons in a similar manner and the resulting neurons were used as an internal standard.

More specifically, the plasmid constructed in this experiment has a structure in which an LIS1 reporter gene having luciferase gene linked to exon 2 of LIS1 gene is integrated. Using this plasmid, plasmids having integrated therein a reporter gene comprising an LIS1 gene from which a part of intron1 and upstream were deleted were also prepared for more detailed identification of the LIS1 transcriptional regulatory region (FIG. 6). Luciferase reporter assay using these plasmids was also performed in a similar manner as above.

The results of luciferase reporter assay of LIS1 reporter genes having various defect regions (FIG. 6) show that when 3-kbp to 15-kbp are deleted from exon1, the expression amount of LIS1 was significantly increased (FIG. 6A). This revealed that the region of inhibiting LIS1 gene expression exists in the region of 3-kbp to 15-kbp from exon1. More detailed analysis of the expression regulatory region revealed that a region that inhibits LIS1 gene expression is present in the region of 5-kbp to 9-kbp from exon1 (FIG. 6B). The DNA base sequence of this region suggests that a region to which CTCF (CCCTC binding factor), which is a control factor that inhibits gene expression, is bound is present in this region.

Analysis of Effect of CTCF Expression on Axon Elongation of Mouse Dorsal Root Ganglion Neurons To investigate whether CTCF inhibits LIS1 expression, a CTCF expression experiment and a knockdown experiment using siRNA were performed using mouse dorsal root ganglion neurons. In the CTCF expression experiment, P3 cells were used as mouse dorsal root ganglion neurons. In the knockdown experiment using siRNA, P15 cells were used as mouse dorsal root ganglion neurons.

In the CTCF expression experiment, the CTCF expression vector was prepared by linking mouse CTCF cDNA (Accession No. Mm.269474) to the cloning site of pEGFP vector (Clonetech: CAG-GFP). Using a Neon electroporation device (Invitrogen), 1 μg of a pEGFP vector having CTCF integrated was introduced into 1×10⁶ dorsal root ganglion neurons to express CTCF. Dorsal root ganglion neurons into which a simple pEGFP vector was introduced were used as a control group.

In western blotting, anti-CTCF antibody, anti-eGFP antibody, anti-Lis1 antibody, and anti-GAPDH antibody were used.

The results show that neurite elongation of dorsal root ganglion neurons was significantly inhibited by expression of EGFP-CTCF (FIG. 7A).

In the knockdown experiment using siRNA, 100 pmol of the nucleotide sequence: UUAAGGUGAUUCCUCAG-GAGGGUGA was introduced as siRNA of CTCF into 1×10⁶ dorsal root ganglion neurons using Neon (Invitrogen). Neurons into which siRNA of pGL2 was introduced in place of siRNA of CTCF were used as a control group.

In western blotting, anti-CTCF antibody, anti-eGFP antibody, anti-Lis1 antibody, and anti-GAPDH antibody were used.

The results show that CTCF knockdown has an effect of promoting axon elongation of dorsal root ganglion neurons (FIG. 7B).

Further, the neurons were observed with a confocal laser microscope. CTCF was forcibly expressed in dorsal root ganglion neurons of 3-day-old (P3) and 15-day-old (P15) mice by using an expression vector. The results show that axon elongation was significantly inhibited in dorsal root ganglion neurons of 3-day-old (P3) mice, and a significant exon elongation inhibition effect was observed in dorsal root ganglion neurons of 15-day-old (P15) mice. Further, CTCF and LIS1 were forcibly expressed in dorsal root ganglion neurons of 3-day-old (P3) mice, and ability to extend axons was found to recover. This result clearly shows that CTCF negatively regulates axon elongation by inhibiting LIS1 expression (FIG. 8). td-Tomato is a very bright red fluorescence protein (dimer). The results of connecting this protein gene and Lis1 gene in tandem and expressing the genes in the cells are shown as td-Tomato-Lis1.

Further, using siRNA, CTCF was knocked down in dorsal root ganglion neurons of 3-day-old (P3) and 15-day-old (P15) mice. As a result, no significant effect on axon elongation was observed in dorsal root ganglion neurons of 3-day-old (P3) mice, whereas a significant axon elongation promotion effect was observed in dorsal root ganglion neurons of 15-day-old (P15) mice. This clearly shows that CTCF inhibition is positively effective on axon elongation by increasing LIS1 expression (FIG. 9).

Elucidation of Role of LIS1 in the Process of Neural Network Maturation Process

The expression amount of LIS1 in the mouse central nerve system was analyzed by using western blotting. Specifically, using protein lysates derived from the brain tissues of 3-day-old (P3), 15-day-old (P15), and 60-day-old (P60) mice, the expression amount of LIS1 was analyzed by using western blotting in the same manner as described above in the "Analysis of Expression Amount of LIS1 Protein in Dorsal Root Ganglion Neurons" section. FIG. 1 shows the results. The LIS1 expression amount in the central nervous system was also found to be gradually reduced after birth.

In the brain of animals shortly after birth, excessive neural connections (synapses) exist. During postnatal developmental stages, only the necessary connections are reinforced, while unnecessary connections are removed, thereby completing mature functional neural circuits. This process is called "synaptic pruning" or "synapse elimination" and is considered to be a universal phenomenon that is seen in neural circuits in postnatal development stages. The ability to regenerate dendrites and neurites declines contemporaneously with "synaptic pruning", and this is considered to prevent regeneration of unnecessary neural circuits. Reduction in LIS1 expression begins exactly at this period; therefore, its relation with completion of mature functional neural circuits is suggested. Accordingly, analysis was performed using mouse mammillary bodies, which are generally used as a neural network pruning model.

An expression vector was injected into the mouse ventricle of 12.5-day old mouse fetus and introduced into cells by electroporation. For analysis, pregnant mice 12.5 days after fertilization (E12.5), which had mouse fetuses, were used. After each pregnant mouse was anesthetized, one of the uterine horns was exposed. After a plasmid solution (DNA concentration 2 to 5 μg/μl) colored with Fast Green was drawn into an injection needle and injected into one side of the lateral ventricle through the uterine wall, the uterus was wetted well with PBS, and the head of the mouse fetus was grasped using tweezer electrodes to apply an electric pulse. The pregnant mice were then allowed to deliver, and the baby mice were analyzed. Using a CAG (cytomegarovirus enhancer, chicken beta-actin promoter, rabbit beta-globin polyA) promoter, fluorescent protein td-tomato was expressed for visualization of neural circuits. The results show that elimination of nerve fibers that grew toward the mammillary body progressed until day 18 after birth (p18) and nerve fibers were no longer observed on day 21 after birth (p21) (FIG. 11). FIG. 11 also shows the results of introducing a Fezf2-eGFP expression vector (a vector expressing eGFP gene in place of Fezf2 gene) into cells in a similar manner and composite (merged) photographs of these results.

Using a CAG promoter, LIS1 and fluorescent protein td-tomato were expressed in a similar manner to visualize neural circuits of mouse fetuses (12.5 days). The results show that expression of LIS1 significantly inhibited nerve fiber elimination, and nerve fibers remained on day 21 after birth (p21) (FIG. 12).

Using a CAG promoter, CTCF shRNA and fluorescent protein td-tomato were expressed in a similar manner to visualize neural circuits of mouse fetuses (12.5 days). The results show that knockdown of CTCF significantly inhibited nerve fiber elimination, and nerve fibers remained on day 21 after birth (p21). This indicates that inhibition of CTCF has an effect similar to enhancement of LIS1 (FIG. 13).

Further, using a CAG promoter and a CMV promoter, CTCF and fluorescent protein td-tomato were expressed in the same manner as above to visualize neural circuits of mouse fetuses (12.5 days). The results show that forced expression of CTCF significantly promotes nerve fiber elimination and that the elimination was already completed on day 15 after birth (p15). This result shows that promotion of CTCF expression has an effect similar to inhibition of LIS1 (FIG. 14).

FIG. 15 shows the mammillary body and orientation of nerve fibers in mouse brain. Using the scale disclosed in FIG. 15, the degree of elimination in each analysis result was quantified. More specifically, with the fluorescence intensity of a portion corresponding to 1 according to this scale being defined as 1.0, the fluorescence intensity of portions corresponding to 2 to 30 according to this scale was expressed in terms of relative values. FIG. 16 shows the results.

Analysis of the Relationship Between GSK3β and LIS1

GSKβ is known to be a protein deeply involved in axon elongation. In particular, activation of GSK3β is considered to negatively regulate axon elongation. Normal-type (LIS1 homozygous) and LIS1 heterozygous mutant dorsal root ganglion neurons were stained using anti-GSK3β antibody. As a result, high accumulation of GSK3β at the tip of neurites was observed in the LIS1 heterozygous mutant (FIG. 17).

The displacement of GSK3β in dorsal root ganglion neurons was analyzed using live cell imaging. The results show that GSKβ dynamically migrates through the axon of dorsal root ganglion neurons (FIG. 18). Further, the results show that there is no difference between the normal type and the LIS1 heterozygous mutant in terms of velocity of displacement of GSK3β in axons (FIG. 19).

Displacement of GSK3β in normal-type and LIS1 heterozygous mutant dorsal root ganglion neurons was observed using live cell imaging, and displacement frequency was analyzed. The results show that displacement of GSKβ in LIS1 heterozygous mutant dorsal root ganglion neurons had significantly reduced retrograde displacement, as compared with that in the normal-type dorsal root ganglion neurons (FIG. 20). This indicates that retrograde displacement of GSK3β by cytoplasmic dynein was impaired in the LIS1 heterozygous mutant dorsal root ganglion neurons.

Activation of GSK3β is known to accompany with phosphorylation of tyrosine 216. Activation of GSK3β in normal-type and LIS1 heterozygous mutant dorsal root ganglion neurons was analyzed by using a specific antibody to phosphorylated tyrosine 216. The results show that terminal GSK3β was significantly activated in the LIS1 heterozygous mutant (FIG. 21). The results suggest that this activation is involved in reduction of axon elongation in the LIS1 heterozygous mutant.

Histological Analysis of Sciatic Nerves in Sciatic Nerve Injury Models

To investigate the effect of SNJ1945 on promoting peripheral nerve regeneration, mouse sciatic nerve injury models were prepared and histologically analyzed. The models were used as sciatic nerve injury model mice produced according to the method of Wall et al. (Wall, 1979). More specifically, model mice were produced in the following manner. Four-week-old female mice were subjected to general anesthesia with sevoflurane inhalation anesthesia (Mylan N.V.) and laid down in a prone position. The skin on the femur was incised. The muscle layer was peeled off carefully and quickly so as not to injure the sciatic nerve. The nerve was severed (completely injured) at mid-thigh at one point with an interval of 40 mm from the periphery. The muscle layer and the skin were then sutured and disinfected. The mice were used as complete nerve injury model mice. Administration of SNJ1945 was performed by mixing SNJ-1945 into a diet (CE-2, CLEA Japan, Inc.) and orally administering the mixture continuously to each mouse in an amount of 200 μg of SNJ1945/per gram of body weight/day. Mice that were subjected to the same complete nerve injury and maintained on a diet not containing SNJ1945 (CE-2, CLEA Japan, Inc.) were used as a control group.

For histological analysis, after the mice were sacrificed by cervical dislocation, sciatic nerves were removed and fixed in 4% paraformaldehyde for 24 hours. After the paraformaldehyde was replaced with PBS, the sciatic nerves were embedded in paraffin. The tissue block was cut into 5-μm-thick sections and each tissue section was adhered onto a glass slide. For hematoxylin and eosin staining, each tissue section was 1) deparaffinized, 2) washed with water, 3) stained with Mayer's or Carrazzi's hematoxylin, 4) lightly washed with running water, 5) allowed to develop color, 6) stained with an eosin solution for 1 minute, and 7) subjected to dehydration, clearing, and embedding; and morphologically observed under an optical microscope.

Samples for observation under an electron microscope were prepared in the following manner. Sciatic nerves were removed in the same manner as above and then placed in a fixative (2.5% glutaraldehyde). Ten minutes after being placed in the fixative, the sciatic nerves were removed and placed in several drops of the fixative that had been dropped on a thick plastic sheet beforehand, and cut into thin sections. Post-fixation was performed using an aqueous osmium tetroxide solution. Next, free water contained in the tissue was replaced with ethyl alcohol. In order to make ultrathin sections, the tissue was embedded in an epoxy resin, and tissue sections were produced with an ultramicrotome. Observation was performed using a transmission electron microscope (Hitachi Ltd.: H-7500).

Mice that were treated in the same manner as above but were not subjected to nerve injury were used as a sham-treated group. FIG. 22 shows the results of microscopic analysis of the sham-treated group.

The analysis by hematoxylin and eosin staining shows that a significant recovery of sciatic nerves in the complete nerve injury model was observed 1 week after administration of SNJ1945, as compared with the control group (FIG. 23). The analysis under an electron microscope shows that recovery of myelin in the complete nerve injury models was also observed 1 week after administration of SNJ1945, as compared with the control group (FIG. 23). FIG. 24 shows graphical representation of counting the number of myelin whose recovery was recognized in the image. A significantly high regeneration of myelin in sciatic nerves was observed in the SNJ1945-administered group, as compared with the control group, and promotion of sciatic nerve regeneration was confirmed.

Administration of SNJ1945 to complete nerve injury models was started 1 week after sciatic nerves were severed, and activation of nerve regeneration was analyzed 1 month after the severance. This analysis can provide analysis of the effect of SNJ1945 on nerve regeneration after nerve cell degeneration was completed during this one week. The results show that even after nerve cell degeneration, significantly high myelin regeneration in sciatic nerves was observed in the SNJ1945-administered group, and promotion of sciatic nerve regeneration was confirmed (FIG. 25).

Functional Analysis of Sciatic Nerves in Sciatic Nerve Injury Models

FIG. 26 shows walking footprints of a sham-treated mouse (left) and those of a complete injury model mouse (right). In this analysis, the complete injury model had a left sciatic nerve severed and thus could not stand firmly on its left paw and therefore had big footprints.

FIG. 27 shows the condition of the paw of a complete injury model mice with a severed right sciatic nerve one month after administering SNJ1945 as described above. The results show that the left paw of a control group mouse (left) drooped, whereas the left paw of the SNJ1945-administered mouse had recovered to the extent that the mouse could grasp the cage.

To further investigate the peripheral nerve regeneration promotion effect of SNJ1945, motor function of sciatic nerve injury model mice was evaluated based on the sciatic function index (SFI) and print length factor (PLI) using Footprint (Bain et al., 1989).

The results suggest that administration of SNJ1945 to complete nerve injury models as described above significantly recovered the sciatic nerves (FIG. 28). Continuous administration of SNJ1945 further promoted recovery of the complete nerve injury models.

---

The invention claimed is:

1. A method for promoting peripheral nerve regeneration to treat a peripheral nerve disorder, comprising
    (i) selecting a subject suffering from a peripheral nerve disorder comprising a severed peripheral nerve or a degenerated peripheral nerve that has degenerated over time after damage, and (ii) administrating to the subject in need of treatment for the peripheral nerve disorder a therapeutically effective amount of a compound represented by the formula:

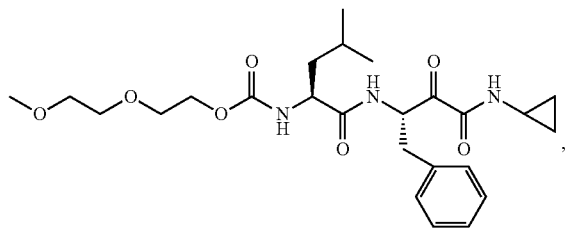 [SMILES: COCCOCCOC(=O)N[C@@H](CC(C)C)C(=O)N[C@@H](Cc1ccccc1)C(=O)C(=O)NC1CC1]

wherein the administering is commenced after the onset of a symptom of the peripheral nerve disorder in the subject, and wherein administering the compound is effective to promote peripheral nerve regeneration.

2. The method according to claim 1, wherein the compound is administered by oral administration, injection, or intravenous drip.

3. The method according to claim 1, wherein the compound is administered at a dose of from 0.1 to 2,000 mg per day.

4. The method according to claim 1, wherein the peripheral nerve disorder is at least one selected from the group consisting of mechanical or entrapment neuropathy, metabolic neuropathy, infectious neuropathy, and drug-induced peripheral nerve disorders.

5. The method according to claim 4, wherein the entrapment neuropathy is at least one member selected from the group consisting of cubital tunnel syndrome, sciatic nerve paralysis, peroneal nerve paralysis, and tarsal tunnel syndrome.

6. The method according to claim 3, wherein the compound is administered in 1, 2, or 3 doses per day.

7. The method according to claim 1, wherein the peripheral nerve disorder comprises a severed peripheral nerve, and administering the compound is effective to promote peripheral nerve regeneration of the severed peripheral nerve.

8. The method according to claim 1, wherein the peripheral nerve disorder comprises a degenerated peripheral nerve that has degenerated over time after damage, and administering the compound is effective to promote peripheral nerve regeneration of the degenerated peripheral nerve.

* * * * *